United States Patent [19]

Seale

[11] Patent Number: 4,646,754

[45] Date of Patent: Mar. 3, 1987

[54] NON-INVASIVE DETERMINATION OF MECHANICAL CHARACTERISTICS IN THE BODY

[76] Inventor: Joseph B. Seale, 44 Puritan Rd., Buzzards Bay, Mass. 02532

[21] Appl. No.: 702,833

[22] Filed: Feb. 19, 1985

[51] Int. Cl.⁴ .................................................. A61B 5/10
[52] U.S. Cl. ...................................... 128/774; 128/649; 128/677; 73/575; 364/508
[58] Field of Search ............... 128/774, 687, 676, 680, 128/694, 739, 649, 745, 677; 73/573–576, 584

[56] References Cited

U.S. PATENT DOCUMENTS

| | | | |
|---|---|---|---|
| 3,030,803 | 4/1962 | Painter | 364/508 X |
| 3,699,808 | 10/1972 | Ford et al. | 73/91 |
| 3,710,082 | 1/1973 | Sloane et al. | 364/508 |
| 3,872,443 | 3/1975 | Ott | 128/774 X |
| 3,878,374 | 4/1975 | Schlatter | 364/508 X |
| 4,352,292 | 10/1982 | Madigosky et al. | 73/575 |
| 4,416,269 | 11/1983 | Enomoto et al. | 128/739 X |
| 4,543,827 | 10/1985 | Tominaga et al. | 73/573 X |

FOREIGN PATENT DOCUMENTS 0721678 3/1980 U.S.S.R. ............................. 364/508

OTHER PUBLICATIONS

Thompson, G. A. et al, "In Vivo Determination of Mechanical Properties of the Human Ulna", MBE, vol. 14, No. 3, pp. 253–262, May 1976.

*Primary Examiner*—Lee S. Cohen
*Assistant Examiner*—Francis J. Jaworski

[57] ABSTRACT

A non-invasive system and method for inducing vibrations in a selected element of the human body and detecting the nature of responses for determining mechanical characteristics of the element are provided. The method comprises the steps of: inducing multiple-frequency vibrations, including below 20 KHz, in a selected element of the body by use of a driver; determining parameters of the vibration exerted on the body by the driver; sensing variations of a dimension of the element of the body over time, including in response to the driver; correlating the variations with frequency components of operation of the driver below 20 KHz to determine corresponding frequency components of the variations; resolving the frequency components into components of vibration mode shape; and determining the mechanical characteristics of the element on the basis of the parameters of vibration exerted by the driver and of the components of vibration mode shape.

39 Claims, 18 Drawing Figures

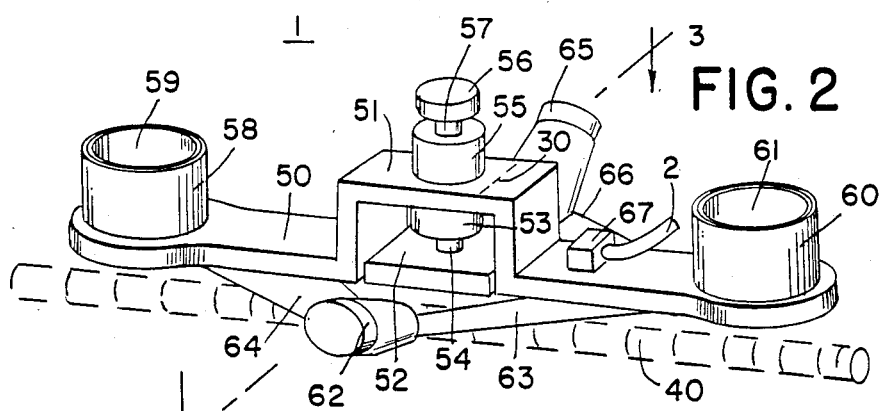
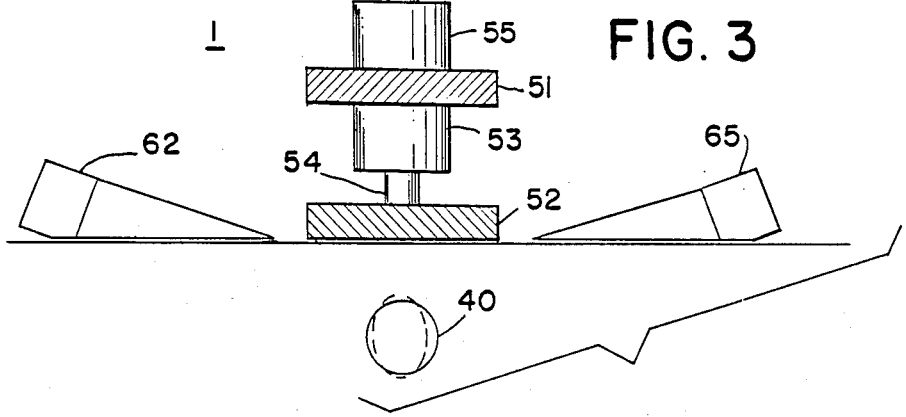
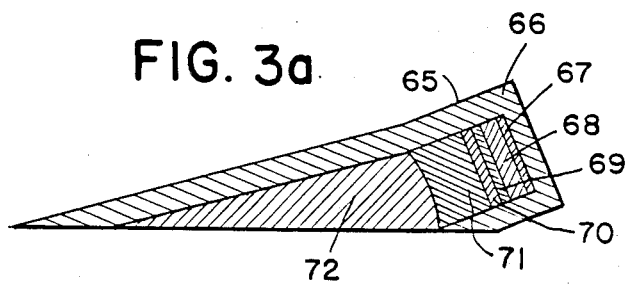

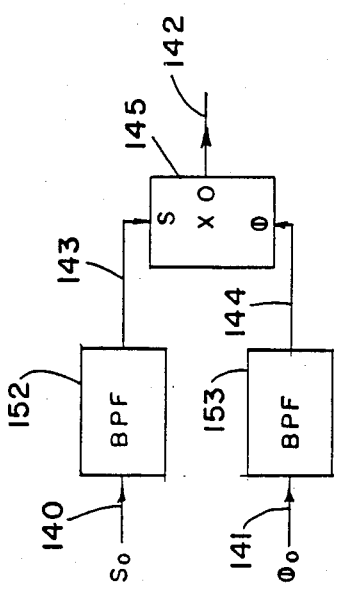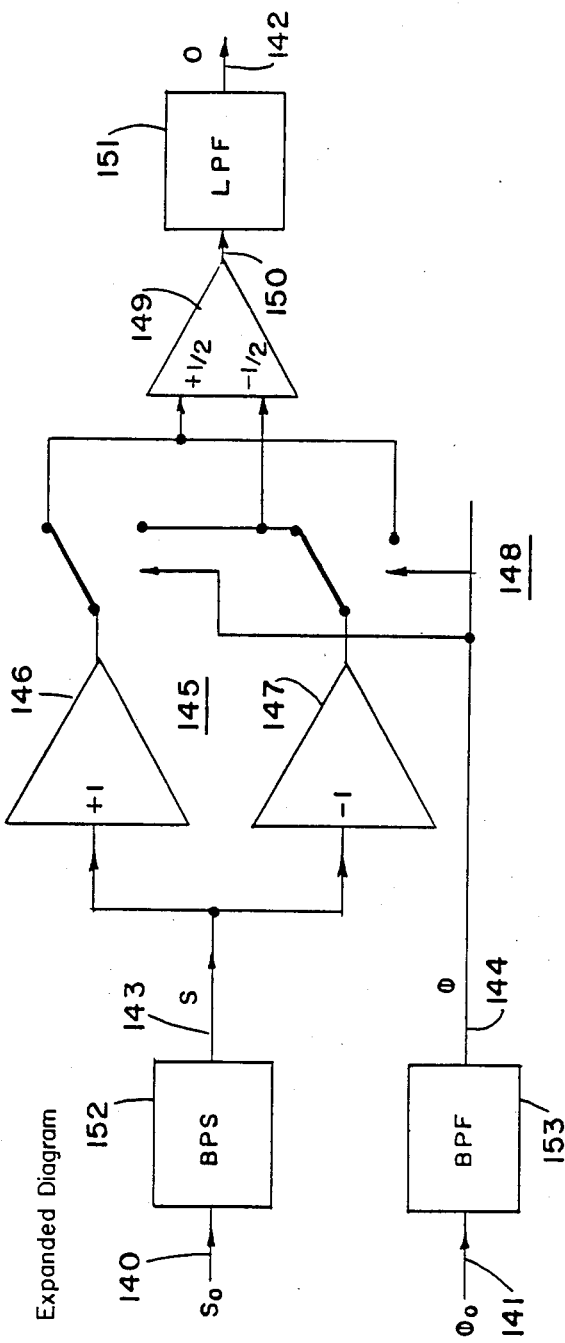
FIG. 6
DEMODULATION FUNCTIONS

COMPUTER INPUT INTERFACE

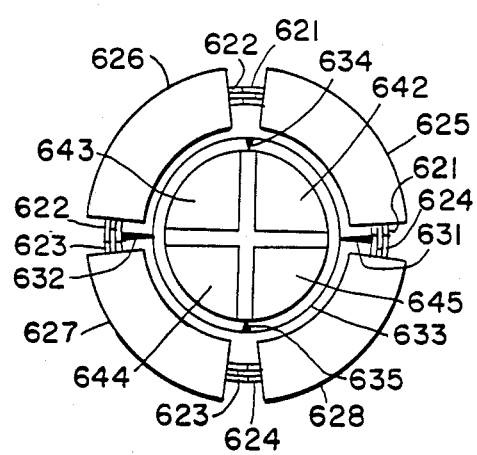
FIG. 11a
FIG. 11b
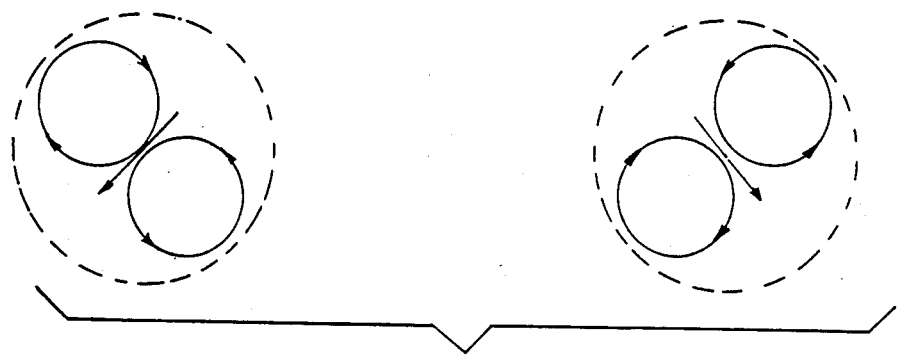
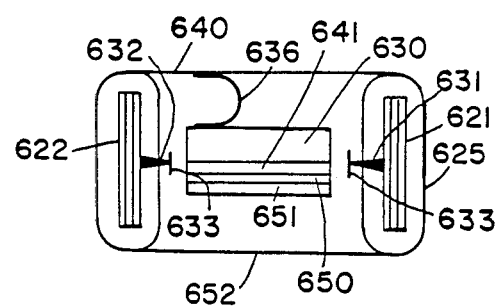
FIG. 11c

NON-INVASIVE DETERMINATION OF MECHANICAL CHARACTERISTICS IN THE BODY

BACKGROUND OF THE INVENTION

This invention relates to non-invasive, small-perturbation measurements of macroscopic mechanical properties of organs and blood vessels to evaluate tissue pathology and body function.

Pathological changes in tissues are often correlated with changes in the mechanical properties of density, elasticity and damping. While microscopic mechanical changes have sometimes been correlated with ultrasound wavelengths and frequencies, many important mechanical changes are manifested most clearly on a large scale at low frequencies down to zero. For these, manual palpation remains almost the sole diagnostic tool. A great deal of effort has been expended in the area of blood pressure measurement, but not by analyzing small-perturbation mechanical properties of the pressurized vessel.

Arterial blood pressure measurement methods are commonly either invasive (catheterization or cannulation) or else disruptive mechanical perturbations, typically causing temporary occlusion of blood flow, e.g. by a sphygmomanometer cuff. Pulmonary arterial pressure is so inaccessible that it is seldom measured. The trauma of entering any artery is an obvious disadvantage. Most occlusive methods are only capable of sampling the systolic and diastolic extremes of the blood pressure waveform. Occlusive methods cannot be used for extended monitoring because of the interruption of circulation.

Recent less occlusive pressure monitoring methods include those described by Aaslid and Brubkak, *Circulation*, Vol. 4, No. 4 (ultrasound doppler monitors brachial artery flow while a servoed cuff maintains fixed, reduced flow) and Yamakoshi et al, "Indirect Measurement of Instantaneous Arterial Blood Pressure in the Human Finger by the Vascular Unloading Technique", *IEEE Trans. on Biomedical Eng.*, Vol. BME-27, No. 3, March 1980 (a similar system optically monitors capillary blood volume in the finger while a servoed cuff maintains a constant optical reading).

Non-invasive blood pressure monitoring approaches suggested in prior art are described by Jeff Raines, *Diagnosis and Analysis of Arteriosclerosis in the Lower Limbs*, Ph.D. Thesis, M.I.T., Sept. 1972 (using a low-pressure cuff surrounding a limb to monitor the changing cross-section as enclosed arteries pulsate in diameter) and by D. K. Shelton and R. M. Olson, "A Nondestructive Technique To Measure Pulmonary Artery Diameter And Its Pulsatile Variations", *J. Appl. Physiol.*, Vol. 33, No. 4, Oct. 1972 (using an ultrasound transducer in the esophagus to track canine pulmonary artery diameter). The latter investigators reported approximate short-term pressure/diameter correlation, while Itzchak et al, "Relationship of Pressure and Flow to Arterial Diameter", *Investigative Radiology*, May-June, 1982, using ultrasound to track canine arterial diameter, found no useful longterm pressure/diameter correlation.

In other areas of the human body, Kahn, U.S. Pat. No. 3,598,111, describes a mechanically and acoustically tuned pneumatic system, useful at a single frequency, for measuring the impedance of the air passages and tissues of human lungs to obtain a two-component trace (representing resistive and reactive impedance) as a function of time.

SUMMARY OF THE INVENTION

The system uses a driver to induce vibrations below 20 KHz into underlying body structures, including organs, fluid-filled organs and segments of blood vessels. The driver includes apparatus for determining parameters of the vibrational excitation applied to the patient, e.g. applied forces or velocities, usually both. Means are provided for sensing structure vibrational motions, e.g. ultrasound, or visual impressions of a stroboscopic display for an ocular approach. Structure dimensions may also be sensed. A computer-controller includes signal-processing equipment and signal interfaces with the sensors. The system obtains sufficient response data related to differing frequencies and, in some cases, to differing pressures, to infer data about the mechanical impedance of the body structure in its local surroundings, and utilizing that impedance data, to infer mechanical parameters of the structure. These parameters may include such intensive tissue or fluid parameters as density, shear modulus, rate of decay of shear modulus due to creep, shear viscosity, and internal pressure; and may also include such extensive or whole-structure parameters as effective vibrating mass or the stiffness of an artery wall.

The computer-controller includes algorithms to infer physical parameters of the structure from the performance and data of the driver and sensing apparatus. These algorithms include at least one of the following:

(1) Network Algorithm, derived from linear network theorems, particularly the Theorem of Reciprocity, which proves there is a useful symmetry for vibration transfer from driver to structure and structure to driver. This algorithm can be applied where time-variation in internal pressure generates at least two distinguishable vibration response patterns at a single frequency.

(2) Simulation Algorithm, including a mathematical simulation model of a structure and its surrounding environment, and sometimes also of the coupling between the driver/sensor assembly and the structure. Parameters of the model are adjusted to optimize the fit between simulated and measured responses. The spectrum of data used for a simultation algorithm is derived at least in part from differing frequencies of driver excitation.

(3) Analytic Function Fit Algorithm, an abstracted simulation approach ignoring structural detail, uses frequency variation data to deduce mass per-unit-length and pressure in a cylindrical vessel, or total mass and the product of pressure times radius in a spherical organ.

Where a network algorithm can be applied, simulation is simplified. Network analysis provides an accurate model for the transfer of vibration energy between driver and structure, substantially independent of the detailed structure of the organ, the driver and intervening tissues. The network analysis reveals the mechanical vibrational impedance of the structure in its local surroundings. Impedance determinations at several frequencies are then incorporated into a simulation analysis without need to model the complicated coupling between the driver and structure. Network results are frequently applied to the analytic function fit algorithm, avoiding the more difficult generalized simulation algorithm.

Where vessel wall stiffness mimics internal pressure, analysis of two different vibration modes distinguishes the separate effects of stiffness and fluid pressure.

Four embodiments of the system illustrate combinations of measurements that determine the mechanical impedance of an organ or vessel in its local surroundings, permitting determinations of pressure and/or tissue properties. Simplified systems taking fewer measurements sometimes yield useful data, while added measurement capabilities often yield better data.

In one aspect of the invention for measuring systemic arterial blood pressure, an elongated vibration driver is disposed in contact with the skin, the long axis parallel to the artery. The vibrational velocity of the driver surface is measured, as is the applied vibrational force over a central segment of the driver. A pulsed ultrasound system measures the time-varying depths of the near and far walls of the artery segment under test, along three cross-arterial axes in the same plane. Circuits correlate ultrasound depth variations with the audio driver vibration signals, to determine the amplitudes and phases of vibrational velocities associated with the three changing diameters and center-depths. These multi-axis vibration correlations are resolved into components of vibration mode shapes. Blood pressure variation over time alters the response phases and amplitudes of these modes. These vibration response alterations in turn affect the surface vibration force and velocity measurements. This blood-pressure-induced change data enables the computer, via a network algorithm, to deduce arterial impedance for one or more mode shapes. The network algorithm is applied repeatedly at different frequencies, to determine the frequency-dependence of an arterial mode impedance at a single pressure. The impedance versus frequency data enter the analytic function fit algorithm, which infers absolute pressure. For an individual patient, the system establishes a table of pressures and vibration parameters, all expressed as functions of arterial radius. For rapid computation of a pressure waveform point, the system interpolates from the table the reference pressure and vibration parameters for the currently-measured radius. The difference between tabulated and current vibration parameters reveal, via the network algorithm, the difference between tabulated pressure and actual current pressure. In this way, a graph of pressure is plotted as a function of time.

If the artery can be excited at close range, it is possible to resolve both two- and three-lobed arterial vibration mode amplitudes and phases from the ultrasound data. The dual-mode data are analyzed to yield two pressure values, one for the two-lobe mode and one for the three-lobe mode. The three-lobe pressure is more sensitive than the two-lobe pressure to wall stiffness artifacts. The difference between the two computed pressures is therefore used to discern true fluid pressure and a wall stiffness parameter.

In another aspect, the invention is configured primarily to determine the impedance of whole vibrating organs. (In the artery-pressure aspect just described, only a segment of a cylindrical vessel was excited. Analysis was based on force at the driver center and a substantially two-dimensional cross-sectional response.) According to this aspect, the driver induces vibrations while its velocity and total applied force are inferred from driver electrical responses. An ultrasound system whose beam is aimed in two dimensions measures vibrational velocities of the near and far walls of an organ.

For fluid-filled organs, e.g. a urinary bladder, the system determines internal pressure. The system also discerns pressure gradients in organ tissues, e.g. from edema. If pressure changes significantly over time, e.g. from urine accumulation or changing tonus of the muscular wall of the bladder, the system uses a network algorithm to compute an especially accurate organ vibrational impedance, leading to a correspondingly accurate internal pressure.

In the absence of pressure-change data, the system infers organ vibrational impedance through detailed simulations. Parameters of the simulated structure are adjusted until mathematical performance substantially matches actual measured data at several frequencies. Adjusted simulation parameters indicate corresponding properties of the underlying organ. Where internal pressure is present, it can be inferred from simulation results. For organs that are not hollow, some simulation parameters correspond to average intensive tissue parameters of the organ: density, shear modulus, viscosity, and sometimes even frequency-variations of modulus and viscosity. Where changes of clinical interest affect these tissue parameters, this aspect has applications as a diagnostic tool, e.g. in instances of cirrhosis of the liver or cystic kidney disease.

Still another aspect of the invention, useful for measuring intraocular pressure, is similar to the last-described aspect of the invention, except that visual impressions and user feedback replace ultrasound as a means of sensing vibrational motions in the eye. In one preferred embodiment, vibrations are induced from the driver through the lower eyelid, avoiding uncomfortable direct contact with the eye surface. Eyelid surface forces and velocities are inferred from driver electrical responses over a wide frequency range. Resonance of the eyeball is measured by a combination of eyelid surface responses and user feedback. The user watches a time-varying display, e.g. on which a horizontal line on a black background strobes, alternately, red and blue-green, at points 180° out-of-phase on the vibrator applied-force sinusoid. For a computer-determined phase setting, the user adjusts frequency until the strobing lines appear to converge into a single white line, indicating synchronization of the strobe with eyeball vibrations. If the lines pulsate perceptably in and out of convergence with each heartbeat, the user is instructed to adjust the frequency to the two outer limits where convergence is just barely achieved at the maximum fluctuations. These settings tell the system the frequency at which a specified vibrational phase is achieved, and how much that frequency varies with intraocular pressure pulsations. The system also strobes a dot whose perceived image is split maximally when the lines are converged. The user adjusts driver amplitude to match the perceived dot spacing to a pair of reference dots, strobed at the zero-displacement times of the line flashes. This amplitude adjustment tells the system the excitation level needed to achieve a reference response. A final spacing adjustment of the reference dot pair gives convergence of these dots at the moment of maximum pulsatile separation from convergence of the strobed lines, telling the system the change in amplitude response due to pulsations in intraopthalmic pressure.

Analysis of these data follows similar lines to the last described aspect, the content of the visual data being comparable to the content of the ultrasound data. The system infers the product of pressure times average ocular radius. For more accuracy and if a separate pressure determination is desired, the user measures eyeball radius, e.g. by looking into a mirror, observing reflections of two lights on the sclera (white of the eye), and matching two cursors to the reflections. It is noted that the radius-pressure product is perhaps a better indicator of glaucoma danger than pressure alone.

Another aspect of the invention is suited for measuring pressure in the pulmonary artery. In preferred embodiments, the patient swallows a cylindrical probe, which is held by a cable partway down the esophagus to rest behind the the right pulmonary artery.

The ends of the probe vibrate axially, driven by transducers that move against a gas volume inside the probe, like acoustic-suspension speaker drivers. Driver expansion/contraction and output pressure vibrations are inferred from changes in driver electrical response. Acceleration sensors detect lateral vibrations at the center and ends of the probe. The lateral movement is caused by asymmetry of the probe surroundings, which include the spinal column just behind the probe. Driver response motion, pressure and lateral movement data are combined to simulate the excitatory field geometry. Ultrasound transducers just above and below the artery-crossing level measure three angularly-displaced diameters. Time variations in the diameter data are analyzed to determine the amplitudes and phases of arterial vibration modes next to the probe. A pressure sensor facing the artery samples the local vibrational pressure field, as well as low-frequency pressure pulsations caused by the artery. This pressure sensing permits refinement of the excitatory vibration field model, which is used to extrapolate mode-excitation strength over the strongly-affected length of artery. Vibration-energy integrals over that length lead to a total energy model, permitting network algorithm solution and subsequent analytic function fit algorithm solution for pressure. By interpreting the decay ot he diastolic pressure curve, the system infers pulmonary capillary pressure.

According to another aspect of the invention, a method for inducing vibrations in a selected element of the human body and detecting the nature of responses for determining mechanical characteristics of the element non-invasively, comprises the steps of: inducing multiple-frequency vibrations, including below 20 KHz, in a selected element of the body by use of a driver means, determining parameters of the vibration exerted on the body by the driver means, sensing variations of a dimension of the element of the body over time, including in response to the driver means, correlating the variations with frequency components of operation of the driver means below 20 KHz to determine corresponding frequency components of the variations, resolving the frequency components into components of vibration mode shape, and interpreting the parameters of vibration exerted by the driver means and the components of vibration mode shape in a manner to determine the mechanical characteristics of the element.

In preferred embodiments determination of parameters of vibration exerted by the driver means includes determining force, or determining velocity; a mechanical characteristic determined is pressure; the method further comprises the step of detecting change in components of vibration mode shape due to pressure change of the element, change being included in determination of the mechanical characteristics of the element; the multiple-frequency vibrations are generated by changing the operation frequency of the driver means over time; the multiple-frequency vibrations are generated by operation of the driver means at multiple frequencies simultaneously; the body element includes a wall, and the method further comprises the steps of: resolving the components of vibration mode shape for at least two modes, and comparing the determined mechanical characteristics of the elements respectively determined on the basis of the components of vibration mode shape for at least two modes in a manner to provide an indication of element wall stiffness; the method comprises sensing the variations of a dimension of the element of the body by means of ultrasound echo signals; a mechanical characteristic determined is systemic arterial blood pressure and the body element is a segment of the arterial system; a mechanical characteristic determined is the mechanical impedance of a body element and the body element is an entire organ; a mechanical characteristic determined is intraocular pressure and the body element is an eyeball, preferably the step of sensing variations of dimension comprises sensing variations of a dimension of the eyeball wherein the method comprises incorporating user feedback in response to visual impressions of a time-varying display, the visual impressions being representative of the response of the eyeball induced by the driver means; a mechanical characteristic determined is pulmonary blood pressure and the body element is a segment of the pulmonary arterial system; in addition to the step of sensing variations of a dimension of the element, the method further comprises sensing a dimension of the element, the sensed dimension being included in determination of the mechanical characteristics of the element, preferably the dimension of the element is sensed by interpreting ultrasound echo signals, and preferably the dimension of the element is sensed optically; and the method further comprises applying a known pressure to the element in a manner to permit calibration, preferably the method further comprises applying the known pressure by means of a pressure cuff.

Other features and advantages of the invention will be understood from the following description of the presently preferred embodiments, and from the claims.

PREFERRED EMBODIMENTS

FIG. 2 is an enlarged perspective view of the vibration driver and sensors of FIG. 1;

FIG. 3 is a sectional view of the vibration driver and sensor assembly of FIG. 2 taken along the line 3—3, while FIG. 3a is an enlarged side section view of one of the ultrasound transducer assemblies shown in FIG. 3;

FIG. 6 is a block flow diagram of the demodulation function;

FIG. 10a is a representation of the vibration drivers and sensors in a whole-organ measurement aspect of the invention viewed from above, while

FIG. 11a is an enlarged view of the ultrasound-transducer aiming system of FIG. 10 from above, while FIG. 11b represents magnetic fields of FIG. 11a and FIG. 11c is a side section view;

HARDWARE AND OPERATION OF THE INVENTION

Essential Hardware

Figure 1:
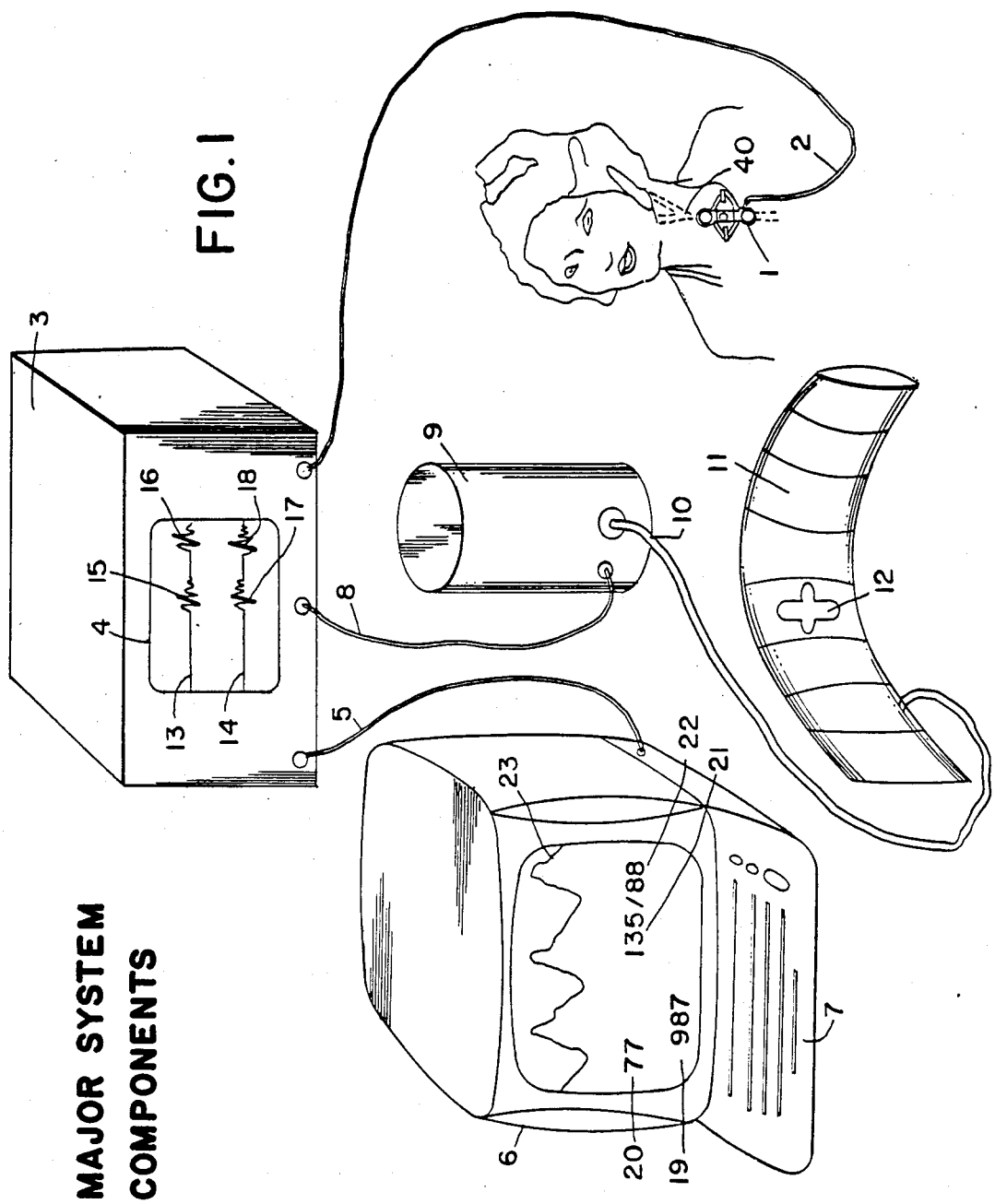
FIG. 1 is a diagrammatic perspective view of the system according to a preferred embodiment of the invention for measuring systemic arterial pressure.

The principal subassemblies of the invention in an aspect for measuring systemic arterial pressure are illustrated in FIG. 1. Vibration driver and sensor assembly 1 is adapted to be affixed to the skin of the patient, e.g. above left common carotid artery 40 shown in dashed outline. Cable 2 connects assembly 1 to computer-controller 3, which includes oscilloscope display 4 for observing ultrasound depth signals. Cable 5 couples computer-controller 3 to video display terminal 6, including keyboard 7. Cable 8 couples computer-controller 3 to pressure-regulating air pump 9, which is coupled in turn by tube 10 to inflatable pressure cuff 11. This cuff includes inset 12 on its inner surface, allowing it to fit over assembly 1, around the neck. The cuff is for optional calibration, to verify or improve system accuracy by applying a known time-varying pressure perturbation, typically much less than diastolic pressure. The correlation slope relating cuff pressure change and vibration-determined pressure change indicates scaling accuracy. Oscilloscope traces 13 and 14 show ultrasound echoes taken from two angles across artery 40. Intensified segments 15 and 16 show echo regions being tracked, corresponding to near- and far-wall artery depths, for one ultrasound angle. Segments 17 and 18 show the corresponding tracked depths for the other ultrasound angle. On the display of terminal 6, the decimal number indicated by 19, e.g. the value 0.987 as shown, is an indication of the average of the squares of the signal trace slopes for echo segments 15, 16, 17 and 18. This signal strength indication is referenced to unity for the strongest signal previously encountered, so that it can be used to compare current alignment of assembly 1 with the "best" previous ultrasound alignment. The number indicated by 20, e.g. the value 77 as shown, is heart rate per minute, derived from blood pressure pulsations and averaged e.g. over the ten most recent pulses. The numbers indicated by 21 and 22 and separated by a slash mark, e.g. 135/88 as shown, indicate systolic and diastolic blood pressure in mm Hg, averaged e.g. over the ten most cardiac cycles. Optionally, the system can display arrhythmia count over a specified time period ending at the present time, again derived from blood pressure data. Finally, trace 23, which moves from right to left as the trace is extended on the right, displays the blood pressure waveform determined by the system.

Assembly 1 is illustrated in greater detail in FIG. 2. Vibrator plate 50 extends the full length of the assembly and includes a central elevated bridge section 51. Plate 50 is configured to contact the skin surface except over the elevated central section. Plate segment 52 fills the gap under segment 51, except for small decoupling gaps at the left and right ends, to contact the skin and provide continuity to the contact area of plate 50. Segment 52 is held substantially rigidly with respect to bridge section 51 of plate 50 by axial post 54 from load cell 53. Using a fairly stiff semiconductor strain gauge bridge, e.g. as sold by Entran Devices, Inc., 10 Washington Ave., Fairfield, NJ 07006, load cell 53 measures the axial force along post 54. Load cell 55 is similar to cell 53 and measures axial force exerted by electronic assembly 56 on post 57. Assembly 56 serves as a countermass, so that the combination of parts 55, 56 and 57 acts as a transducer for accelerations along the vertical axis common to posts 54 and 57.

Positive and negative DC supply voltages arriving through cable 2 into junction box 67 drive the strain gauge bridge circuits in load cells 53 and 55. The two differential signals developed in the bridge circuits of cells 53 and 55 are coupled to two balanced twisted wire pairs in cable 2, via junction box 67. These signals are received and amplified by differential amplifiers in computer/controller 3, resulting in signals representing axial acceleration and force. A small fraction of the acceleration signal is summed with the force signal, to compensate for the acceleration of the inertial mass of plate segment 52 and post 54. This compensation is set so that the force reading from the vibrating assembly is negligible when plate 52 is in air, not contacting a load. Thus, the corrected reading represents force actually delivered to tissue in the patient over the left-to-right length of segment 52. The acceleration signal in computer/controller 3 is integrated over the frequency band of vibration driver excitation, resulting in a signal that closely approximates velocity over that frequency band. Highpass filtering to cut off frequencies below about 20 Hz results in a zero-average velocity signal.

The vibration driver consists of open-ended cylindrical housings 58 and 60, containing respective internal driver and reaction mass assemblies 59 and 61, the housings being affixed to the ends of plate 50. A twisted lead pair in cable 2 provides balanced AC excitation for parallel-wired assemblies 59 and 61. The excitation signal originates from a digitally-controlled sine-wave oscillator in computer/controller 3. In response to this excitation, assemblies 59 and 61 vibrate up and down together, exerting a reaction force via housings 58 and 60 on plate 50. Plate 50 and instrumented segment 52 vibrate together, substantially as a rigid body, transmitting force through the contacting skin area and inducing vibrations in the shape of underlying artery 40, as illustrated in the cross-section of FIG. 3.

Matched ultrasound transducer assemblies 62 and 65 lie on either side of segment 52. They are partially decoupled, vibrationally, from the remaining assembly by flexible flat attachments, e.g. thin spring-metal strips. For transducer 62 these attachments are numbered 63 and 64. For transducer 65, attachment 66 is opposite 63, while the remaining attachment opposite 64 is obscured. Cable 2, via junction box 67, provides coupling of ultrasound electrical signals to and from assembly 1. Assembly 56, besides serving as an accelerometer countermass, contains two small torroidal ultrasound impedance-matching transformers (not shown), whose higher-impedance windings (typically) are coupled to transducers 62 and 65. Assembly 56 also contains a field effect transistor switching circuit (not shown) that selects one of the two transformer lower-impedance windings (typically) for coupling to a coaxial cable in cable 2. A binary select signal to control the switching circuit arrives via an independent coaxial cable included in cable 2. The received ultrasound voltage signal from the selected disk is thus transformed to match the coaxial cable impedance for transmission to computer/controller 3. Conversely, electrical drive pulses from computer/controller 3 are transformed in the other direction for efficient energy coupling to the selected disk.

The DC power supply voltages used for strain gauge bridge excitation are also used to power the selector switching circuit. High frequency decoupling capacitors and resistors (not shown) are included in assembly 56, to avoid cross-coupling interference. Finally, Cable 2 provides grounding and shielding between wire groups, as needed to prevent signal interference.

Vibration plate 50 is oriented with its long axis parallel to artery 40. Ultrasound assemblies 62 and 65 detect arterial diameter at two angles, as shown in FIG. 2 and in the cross-sectional perspective of FIG. 3, top. The sectional plane is parallel to the ultrasound plane defined by the axes of transducers 62 and 65, which includes the vertical axis common to load cells 53 and 55. The section in FIG. 3 is taken just to the right of load cells 53 and 55, along line 3—3 and dashed line 30 of FIG. 2, so that it cuts through segment 52 and bridge section 51 of plate 50. In FIG. 3, an ellipse-mode vibration in artery 40 is indicated by the solid and dashed elliptical coutours. FIG. 3a shows a cross-section of ultrasound transducer assembly 65. The internal details of transducers 62 and 65, discussed later, are the same, since the two assemblies are matched.

Basic Operation

A preliminary description of system operation follows. In a typical application, the patient's neck is lubricated with an ultrasound transmission gel and assembly 1 applied above a common carotid artery. Oscilloscope display 4 initially shows the operator two ultrasound echo traces, displayed one above the other, corresponding to the alternating transmit-receive cycles of assemblies 62 and 65. Horizontal displacement across screen 4 represents echo delay time or, equivalently, depth, while the vertical deflections represent reflected acoustic pressure. The ultrasound signal has been subjected to phase and amplitude correction to maximize depth resolution, by achieving a phase-linear response pulse with smooth band limiting of amplitude.

The transducer assembly is manually centered over the artery by matching the depths of the two echo traces. The operator adjusts rotational alignment so that the artery axis lies, as nearly as possible, perpendicular to the ultrasound plane defined by the two ultrasound beam axes. (If the artery axis does not lie parallel to the skin surface, this causes an irreducible angle error.) This alignment is achieved by maximizing the amplitudes of the two pairs of wall echo traces while maintaining matched depths.

As the operator approaches correct transducer position and alignment, pattern recognition programs in the computer/controller identify the echo complexes of the near and far artery walls for the two displayed ultrasound signals. The machine-recognizable artery echo identification patterns are: (1) approximate depth matching of the two pairs of well echoes, assured by operator adjustments; (2) expected ranges of average depth and spacing for each near-far wall echo pair, based on typical human anatomy; and (3) pulsating echo spacing, resulting from pulsating artery diameter. When the wall echo complexes are machine-identified, the vibration driver is activated and the computer fine-tunes the depths sampled. Specifically, the controller includes phase-lock loop circuitry capable of tracking the depth (i.e., the ultrasound signal delay) of a rapidly-repeated echo signal zero-crossing in a wall echo complex. The computer intervenes in the phase-lock circuit operation to select the zero-crossing to be tracked. A zero-crossing is sought that has a relatively steep slope and whose vibrational motion is large, such that the product of slope times vibration response amplitude is maximized. More specifically, the vibration amplitude to maximize is amplitude relative to the opposite artery wall, so that ultimately the zero-crossing selection is for a pair of zero crossings with large relative motion. The vicinities of the selected zero-crossings are highlighted by oscilloscope beam intensity modulation, as illustrated at 15, 16, 17 and 18.

A digital readout of average wall echo signal strength appears on the screen of terminal 6, to assist the operator in fine-tuning the alignment. The decimal fraction displayed (at 19) becomes 1.000 whenever response amplitude matches or exceeds all previous values. As amplitude declines, the reading indicates response strength as a fraction of the largest achieved. The operator thus learns the best alignment by crossing it, and then returns to the position of maximum signal strength.

Ultimately, the system locks onto three pairs of wall-depth signals, representing three angles across the artery: one for assembly 62, one for assembly 65, and the final pair for a transverse signal where assembly 62 sends the pulse and assembly 65 receives the echo (or vice versa). Trigonometric computer operations give a scaling correction factor for the transverse echo, so that the depth sensitivities of the three depth pairs are computationally matched.

If extended monitoring is contemplated, assembly 1 is now affixed more permanently to the skin. The position is marked with ink dots on the skin, the assembly is removed, and the ultrasound gel is wiped off. A specially cut and marked piece of double-stick surgical adhesive tape is placed on the skin, aligned to the marks. Assembly 1 is applied to the upper adhesive surface of the tape, in the original position and alignment. The tape makes an efficient ultrasound and audio vibration interface.

If extended monitoring is not contemplated, the transducer assembly may be held in place manually.

Once in place and operating, assembly 1 induces vibrations through the skin into the underlying artery. The surface vibration velocity is derived, over the driver frequency band, from the acceleration signal of load cell 55, as described above, while the corresponding force, sampled over the known length of segment 52, is derived from the output of load cell 53, with the acceleration correction described. Plate 50, including the gap-filling segment 52, is of constant width in the middle and widens at both ends to minimize vibrational "end effects", so that the vibration field under segment 52 extending down through the artery depth shows minimal axial variation. Thus, all vibrational motions below segment 52 lie nearly parallel to the ultrasound plane (defined by the axes of transducers 62 and 65). The ultrasound plane should lie substantially perpendicular to the artery axis. Hence, for an arterial segment directly below driver segment 52, and whose length equals the length of segment 52, the vibrational energy coupled to and from that artery segment should correspond closely to the energy coupled to and from driver segment 52. This symmetry permits a proper scaling of sensed parameters to infer blood pressure. The measured force and velocity for driver segment 52 define the instant-by-instant energy flow through the segment. The ultrasound measurements through the three angularly-displaced diameters of artery 40 suffice to define the significant vibration mode responses induced in the artery. Blood pressure variations alter the vibrational properties of the artery. The resulting changes in the signal measurements reveal coupling coefficients characterizing the dissipative and reactive components of force and energy transfer between driver segment 52 and the corresponding artery segment. Further analysis reveals the mechanical impedance of the artery and nearby coupled tissues. Frequency analysis of this arterial mechanical impedance reveals blood pressure, as perturbed by artery wall stiffness. Analysis of two separate vibration modes for apparent pressure reveals separated wall stiffness pressure artifacts and true fluid pressure.

Ultrasound Transducer Details

Referring to FIG. 3a, housing 66 includes air space 67 behind piezoelectric ceramic transducer disk 68, fabricated e.g. of lead titanate zirconate, metallized on the flat surfaces and axially poled, e.g. as manufactured by Edo Corp., Western Division, 2645 South 300 West, Salt Lake City, Utah 84115. The metallizations on the front and back of the disk are typically coupled to the higher-impedance winding of one of the torroidal transformers in assembly 56. Bonded to the front surface of disk 68 are two acoustic interface layers, 69 and 70, which present a graduated change in acoustic impedance from the high impedance of the disk to the low impedance human tissues. The thickness of each layer is approximately ¼ wavelength at the design center frequency of the transducer. Layer 69 may consist of quartz, and layer 70 of acrylic plastic. The ultrasound transducer acoustic interface layers and electrical matching circuitry are constructed in a manner familiar to engineers in the medical ultrasound field, e.g. as in "The Design of Broad-Band Fluid-Loaded Ultrasonic Transducers", *IEEE Trans. on Sonics and Ultrasonics,* Vol. SU-26, No. 6, November 1979.

Adjoining the front surface of interface layer 70 is an astigmatic, divergent acoustic lens. It consists of material layers 71 and 72, with an interface between them that curves relatively strongly in the "ultrasound plane" mentioned above, i.e. the plane of the cross-sectional diagram being examined, and curves weakly in the other direction. Both layers have approximately the acoustic impedance of human tissue (close to the impedance of water), and are made of a polymer of lower acoustic impedance than water, e.g. room temperature vulcanizing (RTV) silicone rubber, loaded with a fine powder of high acoustic impedance. The powder concentration is chosen to raise the low impedance of the polymer up to the desired tissue impedance value. Layer 71 is loaded with high-density powder, e.g. tungsten carbide, while layer 72 is loaded with low-density powder, e.g. graphite. The light powder raises the acoustic impedance of the polymer largely by raising the modulus, while a lesser volume concentration of the heavy powder achieves the same impedance largely by raising the density. As a result of the differing ratios of modulus to density, the speed of sound is higher in the relatively high-modulus, low density layer 72 than in the relatively low-modulus, high density layer 71. The curvature of the interface between the layers, convex away from layer 72 towards layer 71, creates the desired divergent acoustic lens. While the modulus/density ratios are caused to differ, giving differing sound speeds, the modulus-density products of the layers are matched, resulting in matched acoustic impedances and minimal interface reflections. The matched impedances are made close to that of human tissue, to minimize reflections at the lower sloping interface of layer 72 to the patient.

Powder loading of uncured silicon in layers 71 and 72 is achieved without introducing bubbles by mixing powder and uncured silicone and molding in a vacuum. Brief centrifuging settles the mixture into the mold and collapses large voids, but is not extended long enough to settle the fine particles. Upon restoration of atmospheric pressure, remaining vacuum-filled voids collapse, leaving a bubble-free mixture. Housing 66 is part of the mold, and is porous to allow air curing of the contents. After layers 71 and 72 are fabricated and cured, the surface of housing 66 is sealed by impregnation with a polymer resin.

The divergent lenses in the transducers allow the ultrasound system to tolerate differing depths of arteries in various patients. Due to the astigmatic design and low divergence outside the ultrasound plane, the system is relatively sensitive to misalignment whereby the ultrasound plane fails to cut perpandicular to the artery axis.

The ultrasound system is not intended for point-by-point imaging. Instead, the system primarily "sees" surfaces of discontinuity in acoustic impedance in the regions where those surfaces lies approximately tangent to the spreading wavefronts from the ultrasound assembly. Thus, the ultrasound system "sees" near and far artery wall depths, averaged over a significant wall surface area. This spatial averaging minimizes sensitivity to roughness and irregularity of the artery walls. The design also avoids ultrasound "hot spots" where the beam might otherwise expose a small area of tissue for prolonged periods at relatively high intensity. Apparent ultrasound-measured diameters are slightly distorted by arterial wall curvature, since effective echo averaging extends over a finite angle of curvature. Computer algorithms correct for this distortion as necessary.

Vibration Driver Details

Figure 4:
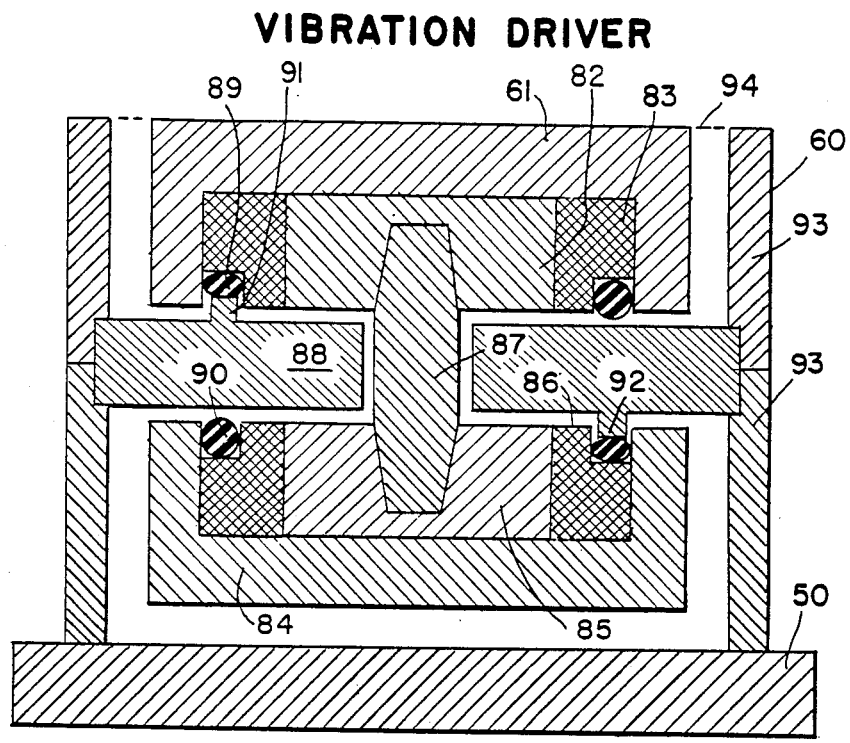
FIG. 4 is a sectional view of a vibration driver assembly.

FIG. 4 illustrates the internal construction of housing 60 and driver/mass assembly 61. Housing 58 and driver/mass assembly 59 are the same. The circular surface 61, visible in FIG. 2, in FIG. 4 is seen as the top surface of an inverted cup-shaped magnetic pole piece, viewed now in cross-section. This cup consists of annealed transformer-grade silicon steel. Inside cup 61 is permanent magnet 82, which may be a rare-earth cobalt magnet consisting, e.g. of material Crucore 18 from Colt Industries, Crucible Magnetics Division, Route #2, Elizabethtown, KY 42701. The polarization of magnet 82 is axial. An electric current in winding 83 will either reinforce or oppose the permanent field, depending on polarities. A similar electrically-variable magnetic field source is set up by silicon steel cup 84, permanent magnet 85 and winding 86. These two magnetic sources are spaced by rigid post 87, of non-ferromagnetic material. Silicon steel washer 88 sits in the gap between the two magnetic field sources. The north-south polarizations of magnets 82 and 85 are parallel and matched, so that the magnetic flux primarily follows a donut-shaped path.

The dominant flux path can be traced from magnet 82 down, through an air gap, into the inner area of washer 88, through a second air gap into magnet 85, down into cup 84, up from the "rim" of cup 84, across an air gap to the outer area of washer 88, up through an air gap to the "rim" of cup 61, and finally full circuit back into the top of magnet 82.

When washer 88 is centered and no current flows through the windings, the magnetic forces on washer 88 substantially balance. Coils 83 and 86 are wound and connected so that an electrical signal that strengthens the fields crossing the upper air gap will correspondingly weaken the fields crossing the lower air gap. This will unbalance the attractive forces, creating a net axial force between washer 88 and the driver/mass assembly.

The axial position of washer 88 relative to the driver/mass assembly is restored by silicone rubber o-rings 89 and 90. The o-rings rest in grooves in windings 83 and 86, with the outer walls of the grooves being the inner surfaces of cups 61 and 84. The windings are resin-impregnated and cured for dimensional stability. The o-rings contact washer 88 only at a circularly-arrayed set of teeth or ridges, illustrated landing in the cross-section of the diagram at 91 and 92. The contact areas of the teeth are curved to follow the round surface of the o-ring, to provide a radial centering force for the washer. The tooth area is chosen to provide the desired restoring force on the washer, enough to overcome the destabilizing influence of the magnetic field and achieve resonance with the inertial load at a desired frequency. When shocked, the washer can contact the entire circumference of an o-ring, which cushions impact force.

Open cylindrical housing 60, as seen in this detailed drawing, is split and includes separable lower and upper sections 93 and 93'. The sections are bonded together to capture washer 88, and the lower end of section 93 is bonded to plate 50. Housing sections 93 and 93' are non-ferromagnetic to avoid diverting flux from the axial gaps. The dashed line at 94 indicates an optional flexible diaphragm to bridge the top of the gap between 60 and 61 and keep dust and especially ferrous particles away from the magnetic gaps.

The leakage flux from the driver/mass assembly will be a steady dipole field and, primarily, a quadrupole AC signal field. The AC component of the field travels radially in the washer and splits roughly symmetrically to travel up and down to cups 61 and 84. Since quadrupole fields lose strength rapidly with distance, unwanted AC magnetic signal couplings are minimized. Washer 88 can be made relatively thin, within minimum stiffness constraints, without causing magnetic saturation, since only signal fields and not the large permanent polarizing field pass radially through the flat plane of the washer disk. For small motions, electro-mechanical efficiency is very high, with a high ratio of response force to input wattage determined by the relatively large available winding volume and the strong polarizing fields in the gaps. The symmetry of the structure minimizes second-order distortion responses. Most of the mass of the assembly is concentrated in the moving element, which includes the permanent magnet, most of the silicon steel and the windings. This transducer is useful for driving high mechanical impedances and for minimizing the mass of one moving part by concentrating the mass in the oppositely-moving part.

OPERATING PRINCIPLES OF A SYSTEMIC ARTERIAL PRESSURE EMBODIMENT

The Fundamental Pressure-Determining Steps

Briefly, a preferred set of procedural steps for determining time-varying absolute systemic arterial blood pressure follows:

(1) Vibrate the skin surface to excite the underlying artery.

(2) Assure, by design and operational adjustment, that vibrational symmetry is maintained for a length of the arterial axis, so that energy relations along a given surface length correlate with energy relations along a corresponding parallel length of underlying artery.

(3) Measure the phase and amplitude of the vibrational force applied along that given surface length paralleling the artery.

(4) Measure the velocity whose product with the force measured in step (3) equals the instant-by-instant power transfer into the given surface length paralleling the artery.

(5) By correlating ultrasound wall echo phase variations with the surface vibrational velocity signal, determine the amplitudes and phases of all significantly-excited arterial vibration modes that are pressure-sensitive.

(6) For each pressure-sensitive vibration mode, by measuring the observable effects of undetermined pressure change at constant frequency, determine the vibrational force/velocity transfer factor that symmetrically relates surface velocity to artery-mode force, and artery-mode velocity to surface force.

(7) Using the result from (6), compute the arterial vibrational impedance for each pressure-sensitive mode. For a given mode, impedance variation is a strong indicator of blood pressure variation.

(8) Through repetitions of the above steps for different frequencies, establish arterial vibrational impedance as a function of frequency for a reference value of blood pressure. Each time that pulsating blood pressure crosses this reference, the crossing is recognized by a vibration signature.

(9) Using known general characteristics of arterial impedance as a function of frequency, use a function-fit to the above impedance-versus-frequency data at constant pressure to establish the dominant low-frequency limit term of the impedance function. This limit term establishes an absolute blood pressure, with possible additive wall-stiffness artifacts.

(10) (Optional) Repeat step (9) for the same reference pressure and a different vibration mode, establishing a second value for absolute blood pressure. This value will differ from the value of step (9) in direct proportion to wall stiffness. A proportion of the difference between these two results is substracted from the reference pressure of step (9) to give baseline fluid pressure, now independent of wall stiffness.

(11) Repeating steps (1) through (9), establish a table of pressures and associated vibration parameters as functions of radius, for a fixed frequency. With this table calibrated to the sensor/patient linkage, real-time pressure tracking is accomplished by table lookup and network algorithm correction to current pressure, using current vibration parameters. The network algorithm correction is needed because pressure is typically not a repeatable function of artery radius.

In deriving detailed operating algorithms, we first concentrate on a common situation in which only one pressure-sensitive vibration mode is measurably excited, specifically the ellipse-mode vibration illustrated in FIG. 3. Where modes of higher order than the ellipse-mode cannot be resolved, it is impossible to complete step 10, and consequently there is no direct way to measure wall stiffness artifacts. Real-time pressure may then be computed with an undetermined additive wall-stiffness error. Except in patients with advanced arteriosclerosis, this wall-stiffness error is small.

Pressure and Frequency Baselines

By analogy to vision, the system gains "parallax" on the measured quatities, to gain "perspective" into the underlying mechanics, through "movement" along either of two separate baselines.

The first baseline movement is change in blood pressure. Internal pressure tends to force the artery towards a circular cross-section. When pressure changes, this alters the effective restoration of the artery towards circularity, which changes the amplitude and phase of the vibrational velocity detected in the artery. The effect of this vibrational change is detected, in turn, by the surface sensors.

Since the change in vibrational motion of the artery arises from internal pressure variation, this change of motion may be treated as if it were a new vibration signal, generated within the artery and propagating outward to the surface sensors. We might call this incremental signal the "parallax" signal, since it is revealed by a movement along the pressure baseline. By combining data about this parallax signal with the original data about driver excitation and arterial response, the system can compute a force/velocity transfer factor that describes the symmetric coupling of force from the driver to the artery and from the artery to the driver. The symmetry of this transfer factor in both directions is proved by the Theorem of Reciprocity. The system can measure both vibrator and artery-mode velocities, plus vibrator force. That leaves only artery-mode force as an unknown in the force-coupling problem. When blood pressure changes, the resulting parallax signal, combined with the original signal, provides enough data to solve for the unknown force. The force/velocity transfer factor falls out, followed by the actual vibrational impedance of the artery in its local environment. Thus, the combined measurements of the invention constitute a powerful remote impedance-measuring probe. Blood pressure and vibrational impedance are related by a simple equation. The impedance and pressure-change data gathered by this pressure-baseline probe are used in the next, frequency-baseline step, to solve for absolute blood pressure.

The second baseline "movement" is change in frequency of the vibrator output. Frequency change strongly alters the relative influences of inertia and stiffness, making it possible to discriminate between the two. Inertial impedance is attributed to the effect of vibrating tissue and blood mass, while stiffness, or restoring impedance, is attributed primarily to blood pressure restoring the arterial cross-section to circularity.

A baseline not needed for pressure determination is organ radius. The dynamics of arterial radius-change with blood pressure-change reveal artery-wall elastic and creep properties, as well as changing tonus of arterial sphincter muscles. For pressure determination alone, however, radius variation tends to complicate matters. All vibration-parameter data need accompanying radius values. Ideally, a time-varying relationship between radius and pressure makes it possible to scan the data and extract both pressure and frequency baseline variations at a constant radius. In cases where radius varies substantially repeatably as a function of pressure, without creep or muscle-tone effects, self-calibrating vibrational determinations of pressure are actually more difficult.

One may define inertial velocity impedance as having a phase angle of $+90°$, which leads approximately, but not exactly, to a linear frequency dependence. Because of the frequency-dependent influence of viscous shear forces on vibration field geometry, the effective moving mass of a vibration mode is frequency-dependent. Extra mass is entrained by shear forces at low frequencies. Hence, inertial velocity impedance does not decline as fast as the first power of frequency at low frequencies.

Restoring velocity impedance has a phase angle of $-90°$ and varies almost exactly as the reciprocal of frequency. The reciprocal relationship is substantially exact for blood pressure and less exact for stiffness pressure, which may decline slightly at low frequencies due to visco-elastic creep. Since stiffness pressure is usually a small correction term, its gradual frequency dependence can usually be ignored. Because of its reciprocal-frequency dependence, restoring impedance dominates overall impedance in the low-frequency limit. Determination of a mode-shape restoring force coefficient (per unit length) to match arterial impedance in a low-frequency limit constitutes determination of blood pressure plus a possible additive wall-stiffness term. Since inertial and restoring impedances together determine net $90°$ impedance, determination of blood pressure amounts to determining and subtracting out the inertial impedance term from the $90°$ impedance data, revealing the pressure term.

We define damping velocity impedance as zero-phase impedance. Because of the phase, this impedance is measured independent of inertial and stiffness impedances. This does not make damping impedance irrelevant to separating inertial and stiffness impedances. Rather, changes in damping impedance are correlated with changes in inertial impedance, since both relate to common underlying changes in vibration-mode geometry with changing frequency. Damping impedance tends to increase weakly with frequency as shear boundary layers become thinner and shear-gradients correspondingly steeper, leveling off at high audio frequencies as boundary layer thicknesses approach the pressure-containing arterial wall thickness. For the purposes of this analysis, mode-shape coefficients for restoring-constant, velocity-damping and mass (all per-unit-length) may be approximated to approach definite high- and low-frequency limits. Though this is not rigorously true (e.g. compressibility effects invalidate this model above the audio frequency range), the approximation leads to an analytic model that is useful over a wide frequency range and reveals parameters of effective moving mass and total elastic restoration (from blood pressure plus tissue elasticity).

The connection between damping and inertial impedances transcends particular models of vibration geometry and can be described in terms of the fundamental properties of complex analytic functions. (A complex function is defined to be analytic if it has a unique complex derivative.) The $0°$ component of a real-world impedance function correlates with the real part of an analytic function. The 90° component similarly correlates with the imaginary part. Frequency corresponds to an imaginary argument of the analytic function. The real and imaginary parts of analytic transfer functions are interdependent, and the same interdependence is observed between the 0° and 90° components of real-world impedances. Consequently, in attempting to extrapolate real impedance data to discover the limiting behavior of the 90° component, it is effective to fit both phase components of impedance to a complex analytic function. Such a function fit utilizes more good data than a real-valued function fitted solely to the 90° component of arterial impedance.

Inertial and restoring impedances cancel at a resonant frequency, leaving a pure damping impedance. Artery vibration mode measurements are typically only accurate in the broad vicinity of this resonant frequency. Very far from resonance, excitation of an arterial vibration mode becomes vanishingly small. It is not feasible to measure arterial impedance so far below resonance that the measurement is totally dominated by the pressure-revealing restoring impedance term. Hence, the goal of the frequency-baseline determination is to observe the behavior of arterial impedance at a fixed pressure, over the usable range of measurement frequencies, and to establish a rational analytic function fit to these data. The correct general form of the transfer function has already been defined, to a great extent, by the physical arguments given above concerning the high- and low-frequency limits of effective restoring constant, damping and inertia terms. Using an approximate fit based on a finite number of measurements and a finite number of analytic function coefficients, the low-frequency limit of the curve is established. The accuracy of this fit depends not so much on the numbers of measurements and function-fit terms as on the linearity of the measurements, on the signal-to-noise ratio of measurements (which can be improved by averaging of many measurements), and on the accurate fulfillment of the symmetry conditions demanded in step (2) and described earlier, in relation to the shape and alignment of assembly 1 in FIGS. 1, 2 and 3. It is noted here that substantial parallelism of tissues along the arterial symmetry axis is needed for high accuracy. If arterial vibrations are monitored where a bone or tendon crosses very near the artery at a sharp angle, symmetry will be compromised. Even with total tissue parallelism along the arterial axis, a sharp departure from radial symmetry very near the artery wall (e.g., from a tendon lying very close alongside the artery) will couple significant energy into high-order vibration modes, causing errors in a system of measurements and analysis based on insignificant energy beyond three-lobed mode shapes.

We now examine how to collect data in a way that permits us to distinguish pressure and frequency dependencies. We designate the two perspective baselines for analysis as:

(1) pressure-change effects at constant frequency, and
(2) frequency-change effects at constant presssure.

The two effects are distinguished in this embodiment by monitoring at a fixed frequency through two or three cardiac cycles (for pressure change effects), shifting to a new frequency for subsequent cycles, then returning to the original frequency, and so on. Although pressure waveforms do not repeat exactly, similar pressure cycles measured at different vibration frequencies are paired as follows: two waveform data segments, sampled and stored close together in time and monitored at different vibration frequencies, are paired if the non-vibratory diameter traces match closely over at least two consecutive cardiac cycles. This ongoing match is a strong indication of matched pressure waveforms, unaffected by progressive trends in arterial sphincter-muscle tone or inelastic creep of the wall tissue. Starting with a frequency analysis based on pairs of matched-pressure cardiac cycles monitored at different fixed frequencies, improved results are obtained by repeating the pair analysis for many matched pairs and averaging the inferred pressure calibration parameters, i.e. those numbers that are subsequently used for determining an absolute baseline pressure. By this averaging, effects of imprecisely-matched pressure cycles tend to cancel, revealing accurately the fixed parameters of the coupled sensor-artery system.

(It is possible to analyze responses while the driver emits more than one frequency essentially simultaneously, for example, by rapid frequency modulation, by frequency splitting using amplitude modulation, by emitting superimposed sinusoids at different frequencies, or pulses with multiple-frequency harmonic content, or a random signal. In some instances, transform analysis is needed to unscramble the data. In the embodiments presented here, excitation and vibration decoding at only one frequency at a time is chosen for economy.)

Arterial Vibration Modes

Figure 5:
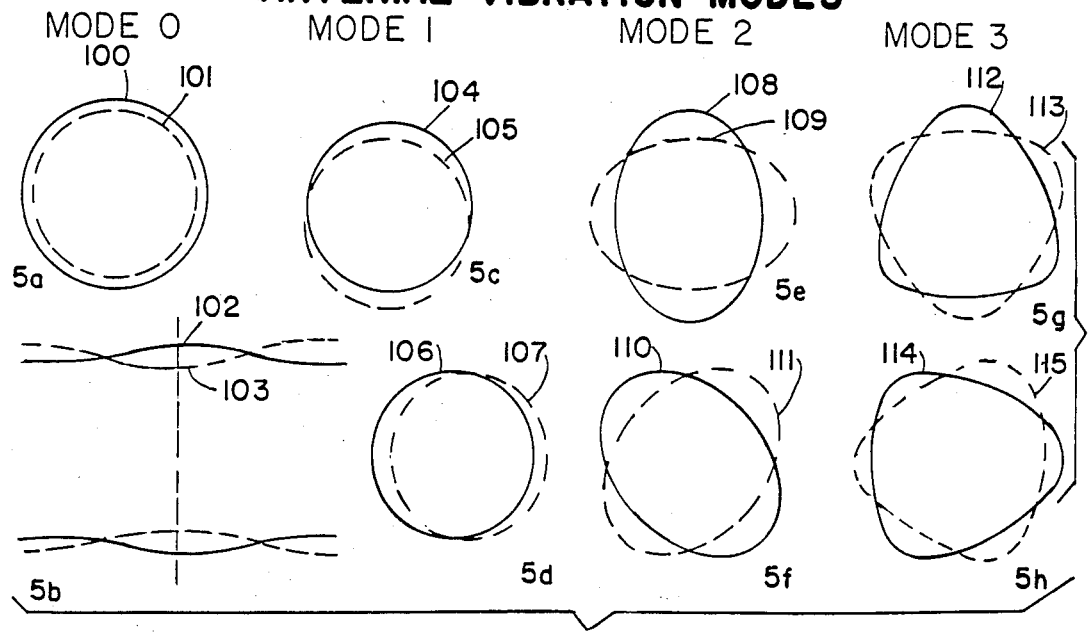
FIG. 5 is a diagrammatic representation of arterial vibration modes.

The vibration mode shapes illustrated in FIG. 5 are the lowest terms in an infinite series of shapes that can be used to analyze any arbitrary vibrational perturbation in a medium that is radially symmetric and unchanging along the third axis, i.e. the axis perpendicular to the cross-sectional plane of the diagram. Mode shape analysis can be applied, with added complexity, where radial symmetry is broken severly, e.g. where a tendon parallels an artery in close proximity. Since the analysis is two-dimensional, it is valid only where the vibrational perturbation is unchanging along the third axis. In the absence of severe violations of radial symmetry, these vibration modes are substantially orthogonal, meaning that there are amplitude-squared terms for power-dissipation and energy of individual modes, but negligible power or energy associated with products of amplitudes of differing modes. Thus the different modes do not interact significantly, but simply coexist superimposed on each other. Modes can therefore be analyzed separately.

The terms in the cylinder mode shape analysis correspond directly to the terms in a Fourier series for a periodic function. The lowest term in a Fourier series is the zero-frequency term, a constant, corresponding to Mode 0 of FIG. 5. We see that radius is changed by a constant amount, independent of angle, from solid contour 100 to dashed contour 101 (FIG. 5a). Since we are discussing vibrations whose acoustic wavelengths typically exceed arterial dimensions by a factor greater than 100, compressibility effects are negligible. Since Mode 0 represents a net change in cross-section, it can only be observed in the present context of incompressible motions if there is axial vibrational movement, so that cross-section areas change differently at other axial locations. This property is reflected by contours 102 and 103 (FIG. 5b), corresponding to contours 100 and 101 and illustrating the same cylinder viewed from the side. The dotted line indicates where the upper cross-sections are taken. To the extent that the desired vibrational symmetry is maintained, Mode 0 excitation should be negligible. Thus, Mode 0 is not a significant vibration mode in the context of the measurements and computations of the systemic arterial pressure-measuring embodiment of this invention.

Mode 1 is a rigid-body vibration of the cylinder between coutours 104 and 105 (FIG. 5c). An energetically orthogonal component of Mode 1 is illustrated in contours 106 and 107 (FIG. 5d), where the motion is at right angles to the upper illustration. Mode 1 vibrations are not sensitive to blood pressure. The vibrations can be affected by pulsating arterial cross-sectional area, but the effect is very weak since it depends primarily on the small difference between blood density and artery-surround density.

Mode 2 and all higher modes are "shape" modes, sensitive both to blood pressure and arterial wall stiffness. They may be influenced to a lesser extent by stiffness in tissues outside the arterial wall, although this effect is very small. Contours 108 and 109 (FIG. 5e) illustrate one axis of excitation of Mode 2, while contours 110 and 111 (FIG. 5f) illustrate a second axis, displaced by a 45° angle. The modes for the two axes are energetically orthogonal.

Mode 3 has a three-lobed symmetry, with one excitation axis illustrated by contours 112 and 113 (FIG. 5g) and a second axis illustrated by contours 114 and 115 (FIG. 5h). This second, energetically orthogonal vibration axis is displaced from the first axis by 30°.

If the vibration driver is directly above the artery and if tissues are symmetric on the left and right sides of the artery, then the excited vibration axes will be vertical, as in the top-row figures for Modes 1, 2 and 3. This left-right symmetry will be violated, for example, if a vein or tendon parallels the artery nearby and to the left or right of the central vertical axis down from driver/sensor assembly 1 (recalling FIGS. 1-3). The differing axis excitations may not be in the same vibration phase, since the symmetry-perturbing object will have its own vibrational phase response to the applied excitation. Circularly-polarized vibrations are possible, in which the shape perturbation appears to rotate rather than vibrate. This arises from the superposition of excitations along energy-orthogonal mode axes and differing in phase by 90°.

High-order vibration mode shapes are excited only by high-order geometric derivatives of pressure and stress in the medium. If the medium is relatively homogeneous, high-order derivatives attenuate very rapidly with depth below the vibration driver. Hence, for deep arteries in relatively homogeneous surroundings, vibration mode excitations above Mode 2 are negligible. Measurable Mode 3 excitation is achieved in shallow arteries or arteries lying next to an impedance discontinuity. Excitation of Mode 3 in shallow arteries can be reduced by using a relatively wide vibration driver, which generates a "smoother" vibration field. Even with a wide driver, however, Mode 3 excitation in the common carotids arises from the proximity of stiff tendons and larynx cartilage and the soft jugular vein. Carotid vibration mode axes may not line up with the vibration driver, and excitation phases may depend significantly on local surroundings.

Significant excitation of arterial vibrations above Mode 3 is difficult to achieve without direct contact between the vibration driver and the artery. For blood pressure determination, high-order mode excitation is undesirable, since it complicates the analysis and since more than three ultrasound angles across the artery are required to separately distinguish higher modes.

Vibrations as Complex Numbers

Throughout, we discuss vibrational quantities characterized by both amplitude and phase relative to a specified reference sinusoid. It is convenient to represent such two-dimensional phase-vector, or "phaser" quantities as complex numbers. In complex notation, the real part of a complex number represents the component of the amplitude-phase vector that is in-phase with a reference sinusoid, while the imaginary part represents the component leading the reference phase by 90°.

Since vibrations induced by the driver are related consistently to the driver velocity phase and proportioned to driver velocity amplitude, the vibrational components are often expressed as complex-valued ratios, with driver velocity in the denominator. In such complex ratios, the phase angle of the quotient is the phase angle of the numerator minus the phase angle of the denominator, and the amplitude of the quotient is the amplitude of the numerator divided by the amplitude of the denominator. Thus, even though the mechanical phase and amplitude response of the driver may change relative to the electrical excitation signal e.g. in response to changing mechanical loading, responses are expressed in a way that is unaffected by "absolute" driver amplitude and phase. The measured vibrator force, when expressed as a complex ratio with velocity in the denominator, is called "surface mechanical impedance". Likewise, velocity measured in an artery by ultrasound is expressed as a transfer ratio, relative to the driver velocity. (Had admittance notation been chosen instead of impedance notation to express mechanical relationships, it would have been more convenient to express all vibrational quantities as ratios to vibrator force, rather than vibrator velocity. The choice of a reference is arbitrary.)

AC Signal Demodulation

Figure 7:
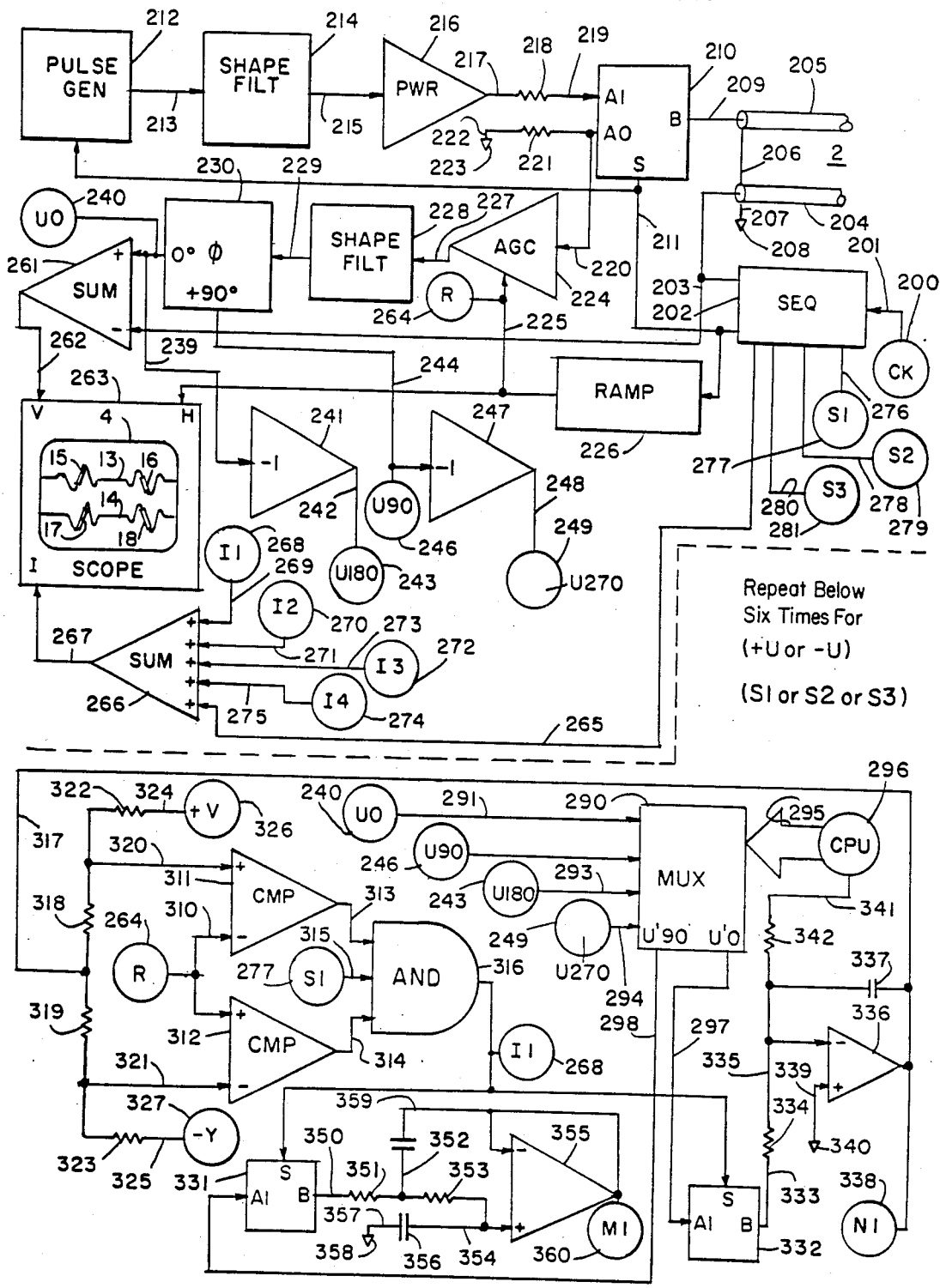
FIG. 7 is a block flow diagram of ultrasound data acquisition.

The functions of a demodulator circuit module are illustrated in FIG. 6. Each repetition of this circuit module in FIG. 7 is designated by the abbreviated schematic symbol box 145, shown at the top of FIG. 6, a box with an "X" for multiplication, the process central to demodulation. The terminals of box 145 are designated "S" for analog Signal input, "$\phi$" for PHase reference input (after the Greek "PHI"), and "O" for Output.

The original, or unconditioned input signals S and $\phi$ are designated by a subscript-o and enter the circuit via wires 140 and 141. These signals are conditioned by matched bandpass filters, shown at 152 and 153. Only one bandpass filter is required per original signal, since a filter output may drive many demodulators. The conditioned signals are designated by unsubscripted "S" and "$\phi$", shown at 143 and 144 and in the input labels of box 145. Since the demodulated output is sensitive only to the relative phases of S and $\phi$, matched bandpass filtering causes no phase-related errors. Demodulated output amplitude is insensitive to the magnitude of the $\phi$ input, but varies linearly with the magnitude of the S input. The effect of bandpass filtering on S magnitude is canceled by using the magnitude of the filtered $\phi$ signal as a reference magnitude, as was discussed above. Specifically, when the reference vibration driver velocity signal is demodulated against itself, i.e., when this signal is bandpass-filtered and applied to both the S and $\phi$ inputs of a demodulator, the amplitude-versus-frequency dependence of the bandpass filter appears in the resulting reference amplitude, just as it appears in other demodulated amplitudes. When the computer divides demodulated signals by the demodulated reference velocity amplitude, the amplitude error caused by the bandpass filters cancels.

Conditioned analog signal S, at 143 in the expanded diagram, enters a differential-output amplifier shown generally at 145. This amplifier is represented schematically as a pair of amplifiers, non-inverting and inverting, at 146 and 147, respectively. Above 148, a transistor current-switching network is represented symbolically as a simple double-pole, double-throw switch. The switch typically involves two switching transistor pairs. Differential-output amplifer 145 and switch 148 are found embodied functionally in a widely-manufactured integrated circuit, designated by a manufacturer prefix followed by "1496", e.g. LM1496 for the National Semiconductor version. The differential output of switch 148 (or the 1496 integrated circuit) is applied to a differential-input amplifier 149, and the single-ended output 150 is applied to lowpass filter 151 to give output "O" at 142. In the actual circuit, part of the filtering function of 151 is incorporated directly into the inputs of amplifier 149, to avoid generating large high-frequency amplitudes.

The polarity of phase reference $\phi$ determines whether the switch poles are up or down. They are up when $\phi$ is positive and down when $\phi$ is negative, with a very fast transition between states. It is easy to see that the signal at 150 represents $+S$ or $-S$, where the sign is $+$ if $\phi$ is positive and $-$ if $\phi$ is negative. Hence, the central portion of the demodulator is a four-quadrant multiplier circuit which is linear only with respect to the S input. Such a multiplier is simpler, faster and less prone to noise and drift than a comparable fully-linearized multiplier.

A demodulator circuit correlates its signal input with the phase of the reference input. In this invention, each vibration signal to be decoded into complex real and imaginary parts is applied to the analog inputs of two identical demodulator circuits. The phase reference input for one of the demodulators typically represents the driver velocity signal, while the phase reference input for the other is phase-locked 90° ahead of the first phase reference. The outputs from the pair of demodulators thus represent the desired real and imaginary vibration components of the analog input, with respect to the reference phase. The phase reference signal (e.g. driver velocity) is expressed by a single demodulator output voltage representing a single real component, since this reference signal is in-phase with itself and thus has no out-of-phase imaginary component.

The filtered output from each demodulator represents a correlation averaged over many vibration cycles. The averaging time-constant is set to the longest value that does not interfere with the needed time resolution of the system. Almost all time-varying blood-pressure data can be encompassed by a bandwidth of 20 Hz, while vibrator frequencies for carotid measurements are typically above 150 Hz. Hence, a margin for signal averaging by the demodulator filters yields good output data from noisy input data. The filtered demodulator output is finally sampled and digitized for computer input. Without preconditioning by demodulation and filtering, the digital input data rate and processing load would typically be increased tenfold, though digital signal processing incorporating the analog demodulation function described here is a feasible design alternative.

The demodulator outputs are typically sampled and digitized at 40 samples/second, sufficient to capture the roughly 20 Hz bandwidth of blood pressure events. Quantities typically sampled at this rate are: 0° driver vibrational velocity (the phase reference); 0° and 90° driver vibrational force; three near-wall and three far-wall arterial ultrasound depths (for the three ultrasound axes, filtered to represent non-vibrational averaged position); and 0° plus 90° phase components, for each of the three ultrasound axes, of differential-mode and common-mode vibrational velocity of the artery walls. That gives a total of 21 parameters at 40 samples/second each, or 840 samples/second, peak. In addition, six ultrasound signal-strength values are typically sampled infrequently, primarily to establish initial phase-lock to the desired ultrasound echoes. Sampling at the peak rate occurs only during short bursts. Data from these bursts is stored and analyzed to define the vibrational characteristics of the measured system. After selection of data for pairing of matched cardiac pressure cycles, a large fraction of the gathered data is discarded. Once baseline reference pressure calculations are complete, subsequent real-time blood pressure computation involves less data sampling and much less data processing.

The Single-Mode Network Algorithm

The network algorithm for pure Mode 2 vibration relates pressure-induced changes in vibration measurements at constant frequency to the coupling between vibrator and artery and to mechanical impedance of the artery itself. The algorithm is based on generalized linear network theorems, particularly the Theorem of Reciprocity, which states in effect that energy must be able to pass through a passive linear network or medium between two objects with equal efficiency in either direction. Here, the medium is the tissue between the vibration driver surface and the artery. Because the energy flow takes the form of vibrations of very small amplitude, non-linear fluid and elastic behaviors of the medium are not elicited. In effect, any smooth function (in this case a mechanical stress as a function of the excitatory vibrational velocity field) appears to be linear if only a very short segment of the function is viewed, e.g. here, a very small vibrational velocity and amplitude.

We have seen how vibration-mode analysis is simplified where there is two-dimensional field symmetry in the arterial cross-section plane over the axial length under study, here the length of driver/sensor segment 52 (FIGS. 2 and 3). Symmetry should cause the measured force for segment 52 to correspond to the transmitted force driving an equal length of the artery below. For a constant-width vibration driver, end-effects cause the artery-driving vibration field to weaken moving off-center. To offset this, the ends of the driver are broadened.

We seek to define a two-dimensional force, i.e. force per unit of axial length, exerted on the artery, simplifying the effects of distributed pressure and shear stress into a single number. We use the approach of generalized coordinate analysis, e.g. as explained in Symon, *Mechanics*, ch.9, Addison Wesley, 1960. The sought-after definition is possible only for a specified vibration mode undergoing a specified motion when force is evaluated. With a defined mode shape, we can use a single length-coordinate to describe motion. For mode shapes like those illustrated in FIG. 5, we describe mode shape changes in terms of changes in length of the radius vector to the cylinder surface along an axis of maximum length-change. If during the vibration cycle we perturb this radius by a very small increment, this perturbation (and the simultaneous radius perturbations at other angles to preserve the mode shape) requires a net increment in work on the vibrating cylinder. The resulting ratio of work increment to length increment defines an effective force for the specified mode shape, according to Eq. 1:

FOR A SPECIFIED MODE SHAPE: $F$=(work increment)/(length increment)     [1]

We understand that "F" and "work increment" in Eq. 1 are both quantities per-unit-length in the direction perpendicular to the cross-section of analysis. We can use an analogous force definition in three-dimensional contexts by omitting the implicit "per-unit-length" qualification. Given a principal vibrational axis for a single mode, we use the term "semi-axis length" to describe the radius along that axis, i.e., the length used to define force. For a Mode 2 vibration, assuming that the ultrasound depth measurements are parallel to the principal vibrational axis, the increment in semi-axis length amounts to half the change in ultrasound-measured diameter. For a Mode 1 or a Mode 3 vibration, ultrasound measurements resolved parallel to a principal vibration axis show a constant diameter but a changing average depth of the near and far artery walls (correcting for ultrasound transducer motion). This changing average depth, or common-mode depth signal, is the change in semi-axis length used in the force definition.

If we consider an entire vibrational cycle, we find that the "work-slope" force defined by Eq. 1 describes a sinusoid having an amplitude and phase. Extending from the definition of incremental, instantaneous force, we define vibrational force Fn, for Mode n at a specified angular frequency f, as a complex phaser quantity having the amplitude and phase of the instantaneous force signal just defined:

Fn=Complex Fourier Component of F, Mode n     [2]

For a multi-mode vibration, we describe force as a multi-dimensional quantity extending along as many complex axes as there are excited modes.

Mechanical vibrational impedance (per-unit-length) is defined according to normal engineering practice, as complex vibrational force divided by complex vibrational velocity. This definition is readily extended to mode shapes using definitions 1 and 2, above. (Recall that the amplitude of a complex quotient is the numerator amplitude divided by the denominator amplitude, and the quotient phase is the numerator phase minus the denominator phase. Similarly, the amplitude of a complex product is the product of the amplitudes of the terms, and the product phase is the sum of the phases of the terms.)

These definitions can be used to apply results of discrete network theory to the continuum measurements of this system. With the symmetries, measurements and definitions outlined here, the passive tissue "network" in question can be modeled in the same fashion as a two-port electrical network, such as is described in electrical engineering and physics texts, e.g. Scott, *The Physics of Electricity and Magnetism*, 2nd ed., 1966, John Wiley & Sons, Inc., New York, p. 500. We consider a black box with two connection terminals, 1 and 2. We know only that the box is passive, containing no internal energy sources, and that its responses are linear. Though this box is usually described as an electrical network, the physical principles apply equally to mechanical systems. The electrical-to-mechanical analogy is as follows. There is a known input electrical current analog, here a vibrational velocity V1 (terminal 1, Mode not applicable); a known input voltage analog, here a vibrational force F1 (terminal 1, Mode not applicable); a known output current analog, here velocity-of-change of the arterial semi-axis length, V22 (terminal 2, Mode 2); and an unknown output voltage analog, here the force F22 (terminal 2, Mode 2) driving the vibration mode. These forces and velocities are related by simultaneous equations 3 and 4, with four velocity-impedance coefficients. (In electrical networks, these are usually stated as admittance coefficients, although the equations are easily rewritten in equivalent form using impedance coefficients.)

$V1 \cdot Z1 + V22 \cdot Zt2 = F1$     [3]

$V1 \cdot Zt2 + V22 \cdot Z22 = F22$     [4]

The Theorem of Reciprocity proves that two of these Z-coefficients are equal. They are both designated Zt2, for transfer impedance, Mode 2. Zt2 and the input and output impedances Z1 and Z22 are unknowns to be determined. Observe that the total "surface mechanical impedance" experienced by the vibration driver is the complex ratio F1/V1, not to be confused with Z1 of Eq. 3. The measured surface mechanical impedance is influenced by arterial velocity V22 via transfer impedance Zt2.

We designate a further arterial impedance, Za2, attributed to the vibrating pressurized blood inside the artery. The force F22 is exerted entirely to overcome impedance Za2 and excite velocity V22 in the cylinder of blood. There is no active source of vibration in the artery to affect the measurements. (Noise from blood flow is present, but is uncorrelated with the vibration driver sinusoid, and thus causes no average error in the demodulated vibration signals.) Hence, we may represent F22 as $-V22 \cdot Za2$. The minus sign arises from the defined direction of F22 relative to V22. We may thus rewrite Eq. 4 as Eq. 5, in terms of the combined tissue-plus-artery impedance, (Z22+Za2), reducing by one the number of complex unknowns.

$V1 \cdot Zt2 + V22 \cdot (Z22 + Za2) = 0$     [5]

If blood pressure changes, this alters the sum (Z22+Za2). Designating the altered values at the new blood pressure with an apostrophe ('), for prime, then we obtain a second set of measurements represented in Eqs. 6 and 7, were V1', F1', and V22' are measured and the Z-coefficients are presumed to be unchanged.

$V1' \cdot Z1 + V22' \cdot Zt2 = F1'$     [6]

$V1' \cdot Zt2 + V22' \cdot (Z22 + Za2)' = 0$     [7]

Eqs. 3 and 6 can now be solved simultaneously, yielding Z1 and Zt2. Substitution into Eq. 5 yields (Z22+Za2), and into Eq. 7 yields (Z22+Za2)'. In Eq.

4, the force F22, representing $-V22 \cdot Za2$, is still unknown, as is Z22.

This solution relies on a change in pressure that alters the vibration measurements to an extent resolvable to useful accuracy. The pressure change need not be known. The system reveals its properties when blood pressure varies, because the phase and amplitude of arterial vibrational motion are altered, and because the effect of this alteration on driver velocity and on driver force is measured, revealing the precise effects of the coupling between the vibration driver and the artery.

To illustrate the parallax increment argument given above, subtraction of Eq. 3 from Eq. 6 yields an equation with the increment terms $V1'-V1$, $V22'-V22$, and $F1'-F1$. Solving simultaneously with Eq. 3 yields the same result as solution of Eqs. 3 and 6 directly. The vibrational change induced by blood pressure can be regarded as an independent vibration signal, generated within the artery, measured by the ultrasound system, and felt as the effects propagate to the surface sensors. Combining the data on this parallax signal with the Eq. 3 data on the baseline signal yields the critical transfer-impedance coefficient, Zt2, permitting subsequent solution for the inaccessible impedances $(Z22+Za2)$ and $(Z22+Za2)'$.

For simplicity, the geometry of the system has been implicitly presumed constant through the change in blood pressure. Arterial radius is different at different pressures most of the time, but not at every instant. The most accurate analysis relies on extracting data sets for which equal radii are observed at differing pressures, as evidenced by differing vibration measurements. Pulmonary artery radius waveforms have been observed to lag behind corresponding internal pressure waveforms, apparently because of visco-elastic behavior of the arterial wall. In peripheral arteries, averaging over several heartbeats, radius has been observed to correlate better with average flow rate than with average pressure, apparently because of active regulation of the smooth sphincter muscles in the artery walls. Whatever the cause of poor pressure/radius correlation, the phenomenon is useful for the current invention because it allows the system to obtain matched-radius data pairs with pressure separation. The network algorithm can then be applied without correction for differing geometry.

In situations where the data fail to yield useful pressure separation for equal-radius data points, the network algorithm becomes more complicated. The single-mode solution just illustrated is based on unchanging values for driver self-impedance, Z1, and driver-artery transfer-impedance, Zt2. The combined artery-plus-surround self-impedance, $Z22+Za2$, is affected by changes in both pressure and radius, but for the moment, the two sources of change need not be distinguished. Z1 is substantially unaffected by arterial radius change. This leaves Zt2, which is significantly altered by radius change. Where the data for Eqs. 6 and 7 are for a different radius than for Eqs. 3 and 5, it is necessary to rewrite Zt2 to analyze radius-change sensitivity.

An expression is derived for the complex ratio $Zt2'/Zt2$, where Zt2 applies to Eqs. 3 and 5, and Zt2' applies to radius-altered Eqs. 6 and 7. This expression permits solution of the network algorithm where there is radius change. This ratio is determined iteratively, proceeding from an estimated $Zt2'/Zt2$ ratio to solve the network algorithm, then using the approximate network results to improve the estimate of $Zt2'/Zt2$, then using this ratio to re-solve the network algorithm, etc. $Zt2 = 2 \cdot Vt2 \cdot Z22$, approximately. Here, "Vt2" represents the velocity transfer coefficient for Mode 2. To understand the physical significance of Vt2, imagine that the artery has been removed and replaced by a uniform tissue whose mechanical properties match the average properties of tissues immediately surrounding the artery. Under these conditions, $Za2=Z22$, and $Vt2=V22/V1$. In the section "Simulation Algorithms", it is argued that the vibration field in the vicinity of an organ or artery can usually be approximated as a potential field under this hypothetical condition of tissue uniformity. For a two-dimensional potential field, it is easily shown that Vt2 varies linearly with radius, r (or more generally, Vtn varies as $r^{n-1}$). Assuming that the effects of tissue elastic modulus are small (a good approximation at the frequencies used to probe a systemic artery), the phase angle of Vt2 is a simple function of the phase angle of Z1, and the magnitude of Vt2 equals radius multiplied by a function of artery center-depth. The specifics of the approach are the effective vibrator method described (in the context of a circular driver) under "Regions Dominated by Potential Flow" in the "Simulation Algorithms" section. The real part of Z22 varies in proportion to $r^2$, while the imaginary part varies as a power law of r that is a function of the phase angle of Z22. A Z22 phase angle approaching zero implies a zero-power law, $r^0$, while a phase angle approaching $+90°$ implies a first-power law, $r^1$. The two functions of phase angle just described are derivable using simulation algorithm techniques. With the information given here and in the "Simulation Algorithms" section, it is possible to solve the network algorithm for measurements at different radii. Solution at a number of frequencies reveals the frequency dependence of Z1, Zt2 and (Z22'Za2). This information can be used in more sophisticated corrections for arterial radius, in a procedure where network solutions are improved iteratively, based on simulation algorithm evaluation of the frequency dependences of network parameters.

It can be shown that the mechanical impedance associated with blood pressure as it restores an artery to roundness in a particular vibration mode shape is directly proportional to blood pressure, inversely proportional to frequency, and indepenent of arterial diameter, tissue properties, etc. As shown in Eq. 8, pressure impedance Zpn for vibration Mode n is imaginary, containing the imaginary unit "j" in the denominator, multiplied by angular frequency "f" in radians/second.

$$Zpn = (n^2-1) \cdot pi \cdot P/j \cdot f \text{ for } n>0 \qquad [8]$$

The Mode $n=2$ and $n=3$ cases are especially important:

$$Zp2 = 3 \cdot pi \cdot P/j \cdot f \qquad [9]$$

$$Zp3 = 8 \cdot pi \cdot P/j \cdot f \qquad [10]$$

Where a relatively pure Mode $n=2$ vibration is obtained and analyzed by the network algorithm for constant radius r and frequency f, then changes in impedance $(Z22+Za2)$ are simply the changes in Zp2. Hence, we can solve for changes in pressure P.

If artery radius differs for different pressures, then it is more difficult to determine pressure change. The change in radius alters the entire geometry of the vibration field, changing effective vibrating mass and damping. It becomes necessary to obtain a complete solution for absolute pressure. Two rapid methods for real-time pressure tracking are described briefly. Subsequent sections provide details to implement these methods.

As an extension of the network algorithm with simulation-algorithm corrections for radius change as described above, we have seen how to estimate the transfer ratio Vt2, and how to use the phase angle and radius-dependence of Vt2 to determine Zt2. Once this is accomplished, we can determine artery-surround impedance Z22. The network algorithm gives the sum, Z22+Za2. Hence, we can subtract Z22 and solve for Za2. Using methods to be described under "Absolute Pressure from a Simplified Simulation", we learn how to estimate the component of Za2 attributed to inertial impedance—half of Zm of Eq. 15. This estimate can be refined, based on the real-valued damping component of Za2. Subtracting the imaginary inertial impedance term from the imaginary part of Za2 yields pressure-impedance Zp2. Solution of Eq. 9 subsequently yields absolute pressure, P.

The second method is to take measurements and compute values for a patient-calibration function, tabulating reference pressures and corresponding vibration parameters as functions of radius. When vibration parameters are subsequently sampled, they are inserted into Eqs. 6 and 7 while radius-interpolated tabular reference parameters are inserted into Eqs. 3 and 5. Network algorithm solution yields a change in the arterial impedance (Z22+Za2), which is related to a change in blood pressure via Eq. 9. The resulting pressure increment is added to the interpolated reference pressure for current radius, yielding current blood pressure.

Of the two rapid methods for pressure determination, the latter requires more lead time to develop a calibration table, but the subsequent computations are probably both quicker and more accurate.

Wall Stiffness Impedance

Arterial wall stiffness causes a velocity impedance having a similar form to Eq. 8, but independent of pressure and having a fourth-power dependence on Mode number n. If arterial wall thickness is approximated as constant during the course of a vibration cycle, then Eq. 11 describes the mechanical impedance Zwn due to wall stiffness.

$$Zwn = \text{const.} \cdot (n^4/j \cdot f) \quad [11]$$

For the important Mode n=2 and n=3 cases, we write:

$$Zw2 = \text{const.} \cdot (16/j \cdot f) \quad [12]$$

$$Zw3 = \text{const.} \cdot (81/j \cdot f) \quad [13]$$

$$(Zw3/Zw2)/(Zp3/Zp2) = (81/16)/(8/3) = 1.8984 \quad [14]$$

Eq. 14 expresses the important difference in proportions between wall stiffness impedance and pressure impedance for Modes 2 and 3. When net effective pressure is computed, separately, for the two modes, the difference in results will represent 0.8984 times the Mode 2 wall stiffness pressure.

The approximation that artery wall thickness does not vary at the vibration frequency, as needed for Eqs. 11-14, is valid if the thickness of the arterial wall is not too large a fraction of radius and if the wall material is much stiffer than adjacent tissue. Under these conditions, the "thin" wall can be bent significantly, but the relatively weak tangential shear forces from adjacent tissues will not cause significant tangential stretch displacements. If the wall is healthy and compliant, there may be significant tangential stretch displacements, but in that case, stiffness impedance Zw is small and unimportant.

Where geometry corrections for changing radius must be incorporated, the dependence of Zwn on radius must specified. A stiffness correction is based on the principle that arterial wall thickness varies roughly as the reciprocal of mean radius, to maintain constant tissue volume under incompressible deformation. Stiffness of a beam or sheet is known to vary as the cube of thickness and inversely as the cube of length. Since the circumferential length of the arterial wall sheet varies in proportion to radius, it follows that arterial stiffness impedance varies roughly as the inverse sixth power of radius. Actually, non-linear changes of tissue elastic modulus with radius-change cause stiffness impedance to vary somewhat more gradually than the inverse sixth-power law.

Absolute Pressure From A Simplified Simulation

To solve mathematically for absolute blood pressure, we must determine the detailed makeup of the term (Z22+Za2). To a first approximation, the imaginary part of (Z22+Za2) is composed partly of the restoring impedance (Zp2+Zw2), and partly of an inertial impedance dependent on the mode shape, the arterial diameter and the average density of blood and surrounding tissues.

There are several ways to evaluate the inertial impedance and extract approximations of blood pressure. The most precise way, as previewed earlier, is to fit a rational analytic function to the measured data and extract the coefficient corresponding to pressure. This approach is quite abstract. What is needed are simple models that indicate the kind of signal to expect and how to design equipment to receive such a signal. This and more sophisticated models tied to the details of arterial structure become valuable in the broadened context where we wish not only to find blood pressure, but to interpret measured impedance data and gain information on the behavior or the artery itself. This kind of question becomes central in the whole-organ embodiment, where evaluation of tissue responses is a primary goal.

From potential flow theory, applying the force definitions of Eqs. 1 and 2, it can be shown that Eq. 15 gives non-viscous inertial mass impedance Zm, as a function of frequency f (multiplied by the imaginary unit j), average density $\rho$, artery radius a, and Mode number n:

$$Zm = j \cdot f \cdot \rho \cdot 2 \cdot \text{pi} \cdot a^2/n \quad [15]$$

Zm is an impedance per-unit-length. Half of Zm is attributed to exterior moving mass (e.g. a part of Z22 in the Mode 2 case), and the remaining half is attributed to interior moving mass (e.g. a part of Za2 in the Mode 2 case). Notice the special n=1 case of rigid cylinder motion. In this case, halving Zm, we recognize the formula for mass per-unit-length of a cylinder, multiplied by the ratio of acceleration to velocity, j·f. The other half of Zm is attributed to surrounding fluid. For higher n, the inertia decreases as the field of motion becomes increasingly localized to the immediate vicinity of the vibrating cylinder surface.

Combining Eq. 15 with Eq. 8 gives the Mode n resonant frequency, frn, where pressure and inertial impedances cancel, leaving only a damping impedance. We can expect the imaginary part of the network impedance term (Z2n+Zan) to pass through zero in the vicinity of frn:

$$frn = (SQRT(n(n^2-1)P/2\rho))/r \text{ for } n>1 \quad [16]$$

The Mode n=2 and n=3 cases are the most useful:

$$fr2 = (SQRT(3P/\rho))/r \quad [17]$$

$$fr3 = 2(SQRT(3P/\rho))/r \quad [18]$$

To correlate these formulas with a real artery, set r to the estimated radius in the artery wall where pressure has fallen halfway from internal blood pressure to ambient pressure. To obtain an effective weighted-average density, $\rho$, weight estimated arterial wall density by n multiplied by (wall-thickness/radius), and for the remainder of the average give equal weightings to estimated blood density and surrounding tissue density. Thus, if wall thickness is 9% of r, then effective average density for n=2 is 2×9%=18% of wall tissue density, plus 41%, each, of blood density and surrounding tissue density, to give a 100% total weighting. For n=3, the weighting factors become 27%, 36.5% and 36.5%. Note that the three densities entering the weighted average will not differ greatly unless calcification has increased wall density, or unless the material around the artery is very fatty and therefore less dense. A better corrected-density estimate, still based on the simplifying assumption of non-viscous fluid flow, takes into account the effective thickness over which blood pressure drop takes place.

The vicinity of fr2 provides the greatest sensitivity of vibration measurements to pressure change. For normal blood pressure and typical carotid artery dimensions, the radian-frequency fr2 translates to about 300 Hz. Because the resonant quality factor, or Q-factor, of arterial vibrations is typically less than 1.0, the usable Mode 2 measurement frequency region typically extends from 150 to 600 Hz. Since resonant frequency varies only as the square root of blood pressure, good signals can be obtained continuously at around 300 Hz without varying frequency over time to track changing frequency fr2.

The most sensitive data on Mode 3 vibrations are obtained at fr3, which is twice as high as fr2 in Eq. 17, and possibly more than twice as high when the large Mode 3 contribution to P from wall stiffness is considered. Consequently, the system uses a higher-frequency measurement range for correlating Mode 2 and Mode 3.

Analytic Function Fit Algorithm

The most recent analysis provides a sense of the nature and magnitudes of the significant terms in arterial vibration dynamics. A general equation for the impedance associated with vibration Mode n expresses this understanding:

$$Zn = (n^2-1)\cdot pi \cdot P/j \cdot f + D(f) + j \cdot f \cdot M(f) \quad [19]$$

For n=2, Z2 corresponds to (Z22+Za2) of network algorithm Eq. 5, or to the corresponding primed quantity of Eq. 7. Where an artery is shallow enough to obtain good Mode 3 excitation, and where the three-angle ultrasound system resolves the modes, Z3 may also be determined by a network algorithm. Hence, we analyze the frequency-dependence of Zn, normally for n=2 or 3, deriving data on Zn from multiple applications of a network algorithm using both pressure-baseline and frequency-baseline data. From this analysis, we distinguish the effect of pressure from other overlapping effects.

It is realized that a wall stiffness error may reside in the term, P. The damping and mass terms, D and M, are functions of frequency f. From Eq. 15, we know that M(f) approaches ($\rho \cdot 2 \cdot pi \cdot a^2/n$) in the high-frequency limit, where viscous shear ceases to entrain extra mass. M is greater than this high-frequency value as f approaches 0. D(f) goes in the opposite direction, from a low-frequency minimum where viscous and shear forces control the flow pattern and prevent steep shear velocity gradients, up to a high-frequency maximum where shear gradients are quite steep, being confined to the arterial wall thickness over which pressure drops from blood pressure to ambient pressure. Define Mode n resonant frequency, frn, as the frequency where complex impedance Zn is real-valued. The relationship of frn to P is shown in Eq. 20:

$$(n^2-1)\cdot pi \cdot P = frn^2 \cdot IM(dZn/df) \cdot (2 + d(\ln(M))/d(\ln(f))) \quad [20]$$

Pressure P is nearly computable from known data, given the tools of network analysis. Where Mode n=2 is dominant, we can easily measure zero-phase frequency frn, here fr2. In the vicinity of fr2, we can evaluate the imaginary part, IM, of the frequency slope of impedance Zn. Relatively simple simulation models tell us how the log-log slope, d(ln(M))/d(ln(f)), typically varies as a function of the non-dimensional quality factor, Q, defined by Eq. 21:

$$Q = fr2 \cdot IM(dZ2/df)/Z2 \quad [21]$$

At resonant frequency fr2, denominator Z2 is real by definition. If D and M were constants, defining a simple second-order system, then Eq. 21 would give the actual resonant quality factor Q, and the log-log slope of Eq. 20 would be zero. For the more complex viscous flow problem being considered here, absolute pressure can be computed from Eqs. 20 and 21 plus an empirical expression for the log-log slope of Eq. 20 as a function of Q. This empirical function is derivable from computer simulation studies, with possible refinement based on animal studies and clinical studies of patients who require arterial catheterization.

Eqs. 22-24 provide a basis for a function-fit approach to determine pressure P, using more computation time but achieving better accuracy:

$$Zn = \frac{A0 + A1 \cdot S + A2 \cdot S^2 + \ldots + Am \cdot S^m + Am + 1 \cdot S^{m+1}}{S + B2 \cdot S^2 + \ldots + Bm \cdot S^m} \quad [22]$$

$$A0 = (n^2-1)\cdot pi \cdot P \quad [23]$$

$$s = j \cdot f \quad [24]$$

As Eq. 24 suggests, the measured complex function Zn of the imaginary argument j·f can be expressed as a part of the encompassing complex function Zn of the arbitrary complex variable s, i.e., as part of Zn(s). As long as Zn arises from a causal linear network ("causal"

networks are mathematically defined as responsive only to past and present input, and not to inputs that have not yet arrived), this extension to a complex function is valid and, for most applications of importance to this invention, uniquely defined. Furthermore, $Zn(s)$ is an analytic function, i.e. it has a unique complex derivative and desirable extrapolation properties. Both the real and imaginary parts of the measured responses bear on the extrapolation of the imaginary part of the function towards zero frequency, to determine pressure-dominated response in a frequency range where measurement accuracy deteriorates. For insight into the connection between imaginary parts and real parts of measured, causal response functions, both in the time and frequency domains, see "The Hilbert Transform", by N. Thrane, Ph.D., in *Technical Review* No. 3—1984 by Bruel and Kjaer Instruments, Inc., 185 Forest Street, Marlborough, Mass. 01752.

A useful form for an analytic function that can be fitted to a finite number of empirical data points is the ratio of two complex polynomials. The polynomial coefficients must be real numbers, since non-zero imaginary parts of the coefficients would lead to assymetry of Zn for positive and negative frequencies, unlike real-world impedances. Finally, the expression should fit the behavior of Eq. 19, where the real-valued functions $D(f)$ and $M(f)$ approach finite limits as frequency f goes to zero and to infinity. This is accomplished by starting the denominator polynomial with a first-order term in s and terminating it at order m, while extending the order of the numerator by one at either end, from a zero order starting term to an $m+1$ order final term. These criteria are all incorporated into Eq. 22. The first-order denominator coefficient "B1" can always be simplified to "1" by dividing the value of B1 through both the numerator and denominator coefficients.

Clearly, coefficients A0, A1 and A2 of Eq. 22 correspond to the low-frequency limit values $(n^2-1)\cdot pi\cdot P$, $D(0)$ and $F(0)$. In the high-frequency limit, where the highest-order terms dominate, the pressure-related, damping and mass terms of Eq. 19 correspond to $Am-1/Bm$, $Am/Bm$ and $Am+1/Bm$, respectively. The $Am-1/Bm$ ratio is not reliably correlated with real pressure or stiffness, however, since pressure and stiffness effects are swamped in the high-frequency data by damping and inertial effects. Physical significance may be attributed to the high-frequency damping and mass terms of the polynomial expression. By comparing the empirical mass term, $Am+1/Bm$, with the value derived for Eq. 15 using the effective radius and density procedures described, it is possible to seek density anomalies due, for example, to artery wall calcification. Recall that Eq. 15 is valid in a high-frequency limit, where damping forces cease to perturb vibrational geometry. The high-frequency damping coefficient, $Am/Bm$, may carry physical significance, although it may not accurately reflect the infinite-frequency limit behavior of the artery, depending on the quality and frequency range of the data.

The Ai and Bi coefficients are real values to be determined from data. Multiplying through by the denominator of Eq. 22 and collecting terms gives:

$$\sum_{i=0}^{m+1} (Ai \cdot s^i) - \sum_{i=2}^{m} (Bi \cdot s^i \cdot Zn) = s \cdot Zn \quad [25]$$

Eq. 25 splits into two real-number equations if the real and imaginary parts are equated separately. Both equations are linear in Ai and Bi and are defined completely by one impedance Zn at one frequency, i.e., one s. Determinations of Zn at $m+1$ separate frequencies and a fixed pressure give $2m+2$ equations to solve for the combined total of $2m+1$ Ai and Bi coefficients. One excess equation may be dropped. The separate impedance determinations are obtained using pressure-matched pairs of cardiac cycles, one monitored at a reference frequency to recognize the reference pressure point in the cycle, and the second cycle monitored at a new frequency for each pair, as described above.

Additional frequency determinations of Zn permit a least-squares regression to obtain a statistically better fit for a given order, m. Once we have solved for coefficient A0, we can solve for pressure P using Eq. 23.

Setting m too high in Eqs. 22 and 25 is likely to cause increased function-fit errors, because the fitted function follows noise in the data. Using a given set of Zn versus s data and least-squares regressions, we start with a small m and determine pressure for successively higher m. Computed pressure will first settle with decreasing steps toward an apparent limit, but will then show increasing fluctuations as m becomes too high. A value of m is found for routine machine computations such that computed pressure is minimally sensitive to m.

Pressure could also be determined from a data fit by using a generalized simulation model for an artery, with undetermined physical parameters for stiffnesses, viscosities, densities, radii and even possible coupling terms for nearby disturbing influences, e.g. tendons. The more abstract approach just shown is computationally simpler and probably at least as good in its final result. A detailed simulation model would provide information besides blood pressure, and may be needed in more complex situations, for example, to probe the mechanical properties of organ tissues. More extensive uses of detailed simulation algorithms are described below.

A Simplified Version of the Systemic Arterial Pressure Embodiment

The concepts so far discussed are easily applied to a simplified version of the systemic arterial pressure embodiment, using only a single ultrasound beam. Referring to FIGS. 2 and 3, we see that the reference segment 52 of assembly 2 could be thickened and an ultrasound transducer set in its center, beamed straight down. The ultrasound assembly is then similar to assembly 65 of FIG. 3, except that the long, slightly tapered conical section of housing originally cut obliquely for angling skin contact is cut short and straight across in the simplified version. The divergent acoustic lens remains, but with reduced defocusing in the plane that cuts across the artery. The operator centers the transducer assembly over an artery by maximizing ultrasound echo signal strength, and aligns the assembly based on anatomical knowledge of the artery below.

When an artery receives negligible Mode 3 excitation and when Mode 2 excitation aligns with the transducer symmetry axis and the ultrasound beam, the single-mode network algorithm and analytic function fit algorithm suffice to solve for blood pressure. Left-right tissue asymmetries can cause misalignment between the ultrasound and vibration mode axes, leading to pressure errors. For many anatomical sites, such asymmertries are negligible. This single-mode determination does not resolve ambiguities of wall stiffness.

In the next section, we consider a single-axis ultrasound vibration measurement that includes resolvable Mode 3 excitation. Assuming left-right tissue symmetry, we show that the measured data is not quite sufficient to allow a "pure" two-mode network solution. One can complete the solution using a few fairly reliable simulation assumptions. Hence, with an artery segment in the right depth range and in fairly symmetric tissue surroundings, the simplified version of the systemic arterial pressure embodiment can provide an estimate of blood pressure corrected for arterial wall stiffness. Undetectable errors may arise due to assymmetric tissue surroundings, however, giving the two-transducers, three-axis ultrasound approach an advantage in accuracy and confidence, mitigated by increased hardware cost.

The Two-Mode Network Algorithm

If the ultrasound system measures depths of near and far walls of an artery along a single axis, and if that axis is presumed to be a major vibration axis for Modes 1, 2 and 3, then the equivalent of one real parameter of the network solution remains undetermined. The ambiguity is approximately resolved by a simple correction based on the relative sensitivities of different modes to arterial radius change. More sophisticated simulation analysis can improve the approximation. We call this overall approach the two-mode network algorithm, since there are two pressure-sensitive modes involved, 2 and 3. The presence of pressure-insensitive Mode 1 adds some difficulty.

For convenience, vibrator velocity V1 is defined as a constant reference quantity, and all other variables are expressed relative to this reference, as was discussed under "Vibrations as Complex Numbers". Arterial wall velocity V2 splits into measured common-mode and differential velocity components, V2c and V2d. The measured common-mode velocity, V2c, has two superimposed Mode contributions: $V2c=V21+V23$, for Mode 1 and Mode 3. We avoid subsequent use of the unknown amplitude V23 by substituting $V23=V2c-V21$. Since only Mode 2 contributes significantly to the measured differential velocity, we set $V2d=V22$. The measured driver force, F1, consists of Mode 2 and Mode 3 transfer impedance contributions, plus a pressure-insensitive contribution, Fpi. The force driving Modes 2 and 3 is then the total driver force minus the pressure-insensitive contribution: F1−Fpi. Mode 2 and Mode 3 transfer impedances, Zt2 and Zt3, complete the variable list. With these, we may write Eqs. 26-28:

$$V2d \cdot Zt2 + (V2c - V21) \cdot Zt3 = F1 - Fpi \quad [26]$$

$$V1 \cdot Zt2 + V2d \cdot Z2 = 0 \quad [27]$$

$$V1 \cdot Zt3 + (V2c - V21) \cdot Z3 = 0 \quad [28]$$

Eq. 26 states that the pressure-sensitive component of the driver force, obtained by subtracting the unknown Fpi from measured F1, arises from the two pressure-sensitive transfer impedances Zt2 and Zt3, multiplied by the corresponding mode velocities V22 (=V2d) and V23 (=V2c−V21). Eq. 27 states that there is zero internal active force driving V22 (=V2d), so 0 is equated to the sum of the transfer-force V1·Zt2, plus the passive internal impedance force V2d·Z2. Eq. 28 expresses the same thing as Eq. 27, except for Mode 3.

If there is a delta-pressure, Pd, altering vibration conditions at constant diameter, we obtain a second set of of equations. Scaled V1 is held constant at its reference value, which is simply $(1+0j)$ if all other measurements are scaled using complex division by the unscaled V1. Changed quantities are designated by an apostrophe ('), for "primed" values in Eqs. 29, 30 and 31:

$$V2d' \cdot Zt2 + (V2c' - V21) \cdot Zt3 = F1' - Fpi \quad [29]$$

$$V1 \cdot Zt2 + V2d' \cdot (Z2 + 3 \cdot K \cdot Pd) = 0 \quad [30]$$

$$V1 \cdot Zt3 + (V2c' - V21) \cdot (Z3 + 8 \cdot K \cdot Pd) = 0 \quad [31]$$

$$K = pi/j \cdot f \quad [32]$$

V1 is not primed since by adjusting other variables to this reference, V1 remains unchanged. V21 is not primed, since this Mode 1 excitation is unaffected by the pressure change at constant arterial diameter, and so remains constant relative to V1. The factors 3K and 8K come from Eqs. 9 and 10, with K defined by Eq. 32, expressing the sensitivity of Z2 and Z3 to delta-pressure Pd. For the six equations 26-31, there are six complex unknowns plus one real unknown: Z2, Zt2, Z3, Zt3, V21, Fpi, and the real variable, Pd. All other quantities are defined by measurements. For solution, it is convenient to rewrite Eqs. 29-31 as differences with corresponding Eqs. 26-28 subtracted out (i.e., as "parallax equations" for pressure baseline "movement", recalling the earlier heuristic explanation of the meaning of these measurements):

$$(V2d' - V2d) \cdot Zt2 + (V2c' - V2c) \cdot Zt3 = F1' - F1 \quad [33]$$

$$(V2d' - V2d) \cdot Z2 + V2d' \cdot 3 \cdot K \cdot Pd = 0 \quad [34]$$

$$(V2c' - V2c) \cdot Z3 + (V2c' - V21) \cdot 8 \cdot K \cdot Pd = 0 \quad [35]$$

Beginning with a tentative value for Pd, to be subject to iteration, the remaining equations can be solved, recalling that most of the varibles are measured knowns. Beginning with Pd and Eq. 34, we solve for Z2; then with Eq. 27 for Zt2; then with Eq. 33 for Zt3. We must then solve Eqs. 28 and 35 simultaneously for Z3 and V21. The solution is quadratic in V21, leading to two values for V21 and, upon substitution, two values for Z3. The extraneous quadratic root for V21, and the corresponding Z3, must be recognized and discarded. The correct quadratic root is used to solve Eq. 26 for Fpi. In most situations, the extraneous quadratic root can be recognized as "unreasonable" in terms of anatomy and physics.

The above analysis presumes no corrections for changing arterial radius at different pressures. In situations where differing-pressure data can be resolved only at differing radii, it is necessary to account for radius-sensitive changes in transfer impedances. The basic approach to this has been described for the single-mode network algorithm. The same principles apply here.

To determine Pd, more information is needed than the network algorithm can provide directly. The analytic function fit algorithm is therefore applied. To obtain equal-pressure data extended along a frequency baseline, using matched pressure-cycle pairs, data quadruples (f, F1, V2c, V2d) are required, each referenced to a fixed V1. The quadruples are required for a set of frequencies, f=f1, f2, f3, etc., with enough frequencies to obtain analytic function fit solutions. At each frequency, the data quadruples must be measured at two distinct pressures, P1 and P2, to be determined, but recognized as differing pressures by differences in vibration data. The same two pressures are required for each frequency. This is accomplished by the pressure-cycle matching process (described previously). If a pressure differential $Pd = P2 - P1$ is assumed, then the network algorithm can be solved for arterial impedances at P1 and P2 for each of the measured frequencies. This impedance data plugs into the analytic function fit algorithm, which yields values for P1 and P2. The difference, $P2 - P1$, is used to establish a revised estimate of Pd, which feeds back into the network and analytic function fit solutions in an iterative manner, to convergence. The network and analytic function fit algorithms are thus solved simultaneously.

Given dual-mode pressure solutions, detectable arterial wall stiffness will cause a positive apparent pressure difference, $(P3 - P2)$, for Mode 3 and Mode 2 pressures. Recalling Eq. 14, this pressure difference represents the Mode 2 wall stiffness "pressure" multiplied by 0.8984. The value $P2 - ((P3 - P2)/0.8984)$ therefore represents absolute fluid pressure, corrected for wall stiffness.

Three-Axis Ultrasound Interpretation

The analysis shown so far is valid only to the extent that vibration-mode principal axes all lie parallel to an ultrasound axis, as with the single-axis variation of this systemic arterial pressure embodiment. If this symmetry criterion is met, then three-axis ultrasound measurements suffice to determine the separate Mode 1, Mode 2 and Mode 3 vibrational excitations. With these data, the two-mode network algorithm can be solved separately. Then, the analytic function fit algorithm need only be solved once for an absolute pressure.

If single-axis vibration symmetry is not assumed (the assumption is often inaccurate), then the network and analytic function fit algorithms must be solved simultaneously, iteratively, even with three-axis ultrasound data.

To understand the data requirements for resolving simultaneously-excited vibration modes, consider Mode 1 for single-frequency excitation. Mode 1 is a simple translational motion in two dimensions. Whenever single-frequency sinusoidal motions along different axes in a plane are superimposed, the resulting trace is an ellipse (including the special cases of a circle and a line segment, which is a degenerate ellipse). To specify all the parameters of the trace, begin by specifying the two components of the major axis vector. Resolving the component of sinusoidal trace motion along this major axis, the third parameter is the phase of this major-axis sinusoid relative to a specified reference phase (e.g., vibration driver velocity V1). Rotating in space $+90°$ from the major-axis vector, the minor-axis amplitude is described as the fourth parameter. This amplitude is positive for counter-clockwise rotation, or otherwise negative. By choosing to measure along the major and minor axes, the phase of trace motion resolved along the minor axis is constrained to differ from the major-axis phase by 90°. Hence, four parameters completely specify the vibrational motion.

For single-frequency excitation of a higher-order shape mode, four parameters are again sufficient. Recalling the descriptions of Modes 2 and 3 in conjunction with FIG. 5, it is seen that two energetically-orthogonal shapes are separated by principal axis rotations of 45° for Mode 2 and 30° for Mode 3.

The three-axis ultrasound system resolves three common-mode and three differential-mode vibrational velocities. Each resolved velocity has 0° and 90° phase components. The resulting six differential-mode components are more than sufficient to determine the four parameters of the differential Mode 2 vibration. The six common-mode components are insufficient to determine the eight parameters needed to determine both Modes 1 and 3. To help resolve the uncertainty, Mode 1 excitation is not significantly affected by either pressure or radius changes in the artery, while pressure and radius sensitivities of higher modes have been described. This is useful for determining the Mode 3 velocity transfer ratio parameter, Vt3, which in this context is a four-parameter quantity, like the vibration modes, involving two energetically-orthogonal versions of the Mode 3 shape. Common-mode vibration changes directly reveal the major-axis direction and major/minor axis amplitude ratio for Vt3. Final resolution of the network algorithm uncertainty uses simultaneous solution of the network algorithm with the analytic function fit algorithm. The detailed solution process follows directly from the principles and procedures already described.

Electronic Signal Acquisition

The functions of vibration driver and sensor assembly 1 (FIGS. 1–3) have been described. We now described what happens to the electronic signals that pass via cable 2 (FIGS. 1, 2) between assembly 1 and computer/controller 3.

Figure 8:
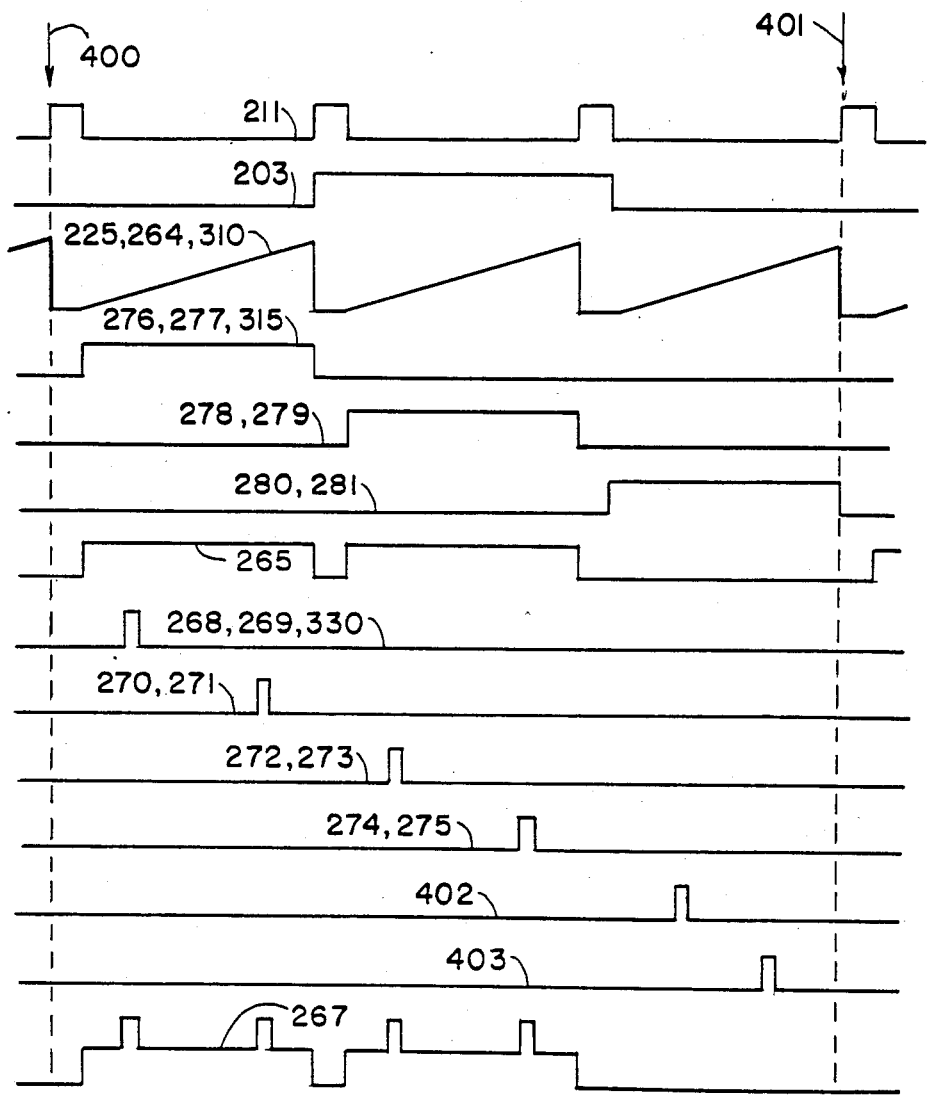
FIG. 8 is a representation of electronic waveform traces of FIG. 7.
Figure 9:
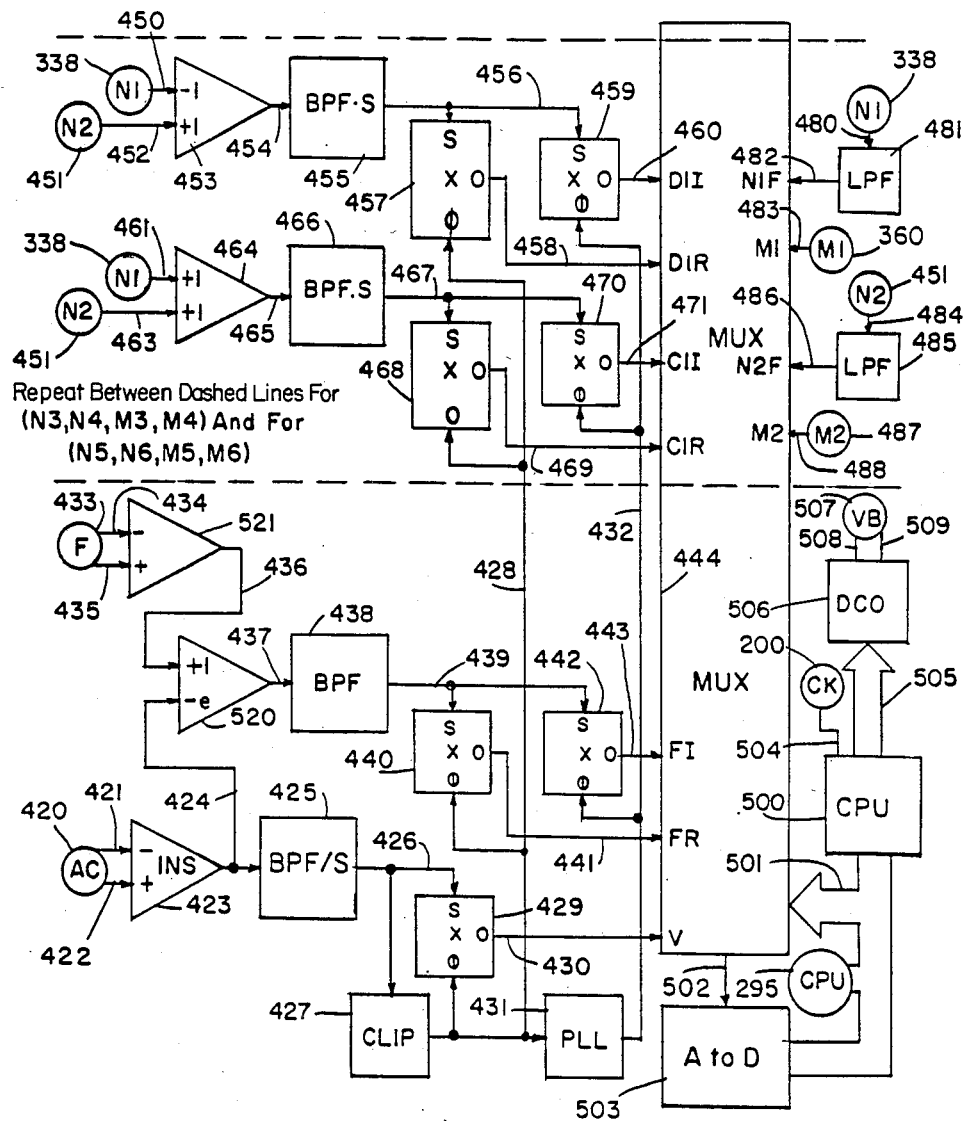
FIG. 9 is a block flow diagram of interfacing of computer input and output data.

The signal processing is illustrated in FIGS. 7, 8 and 9. The "Ultrasound Data Acquisition" assemblies of FIG. 7 generate and receive broadband ultrasound signals (typically exceeding 500 KHz bandwidth) and process them into low audio-band (typically below 1 KHz) analog voltages representing arterial wall depths and echo signal strengths. FIG. 8, "Ultrasound Sequencing", illustrates timing waveforms from FIG. 7. FIG. 9, "Computer Input Interface", illustrates how all low audio-band data is demodulated and/or filtered to yield depth and vibration phaser signals with typical bandwidths of 20 Hz. These narrow-band signals are predigested vibration data that is sampled and digitized for computer input.

In FIG. 7, modules across the top perform pulse-generating, shaping, amplification and switching. Modules across the middle of the figure perform gain controlled amplification, further pulse-shaping, 90° phase-shift filtering, and digital sequencing, including the control of oscilloscope display functions. Modules across the bottom of FIG. 7 cause the time window of highlighted segment 15 on the oscilloscope trace to track a positive-sloping waveform zero-crossing. In the 90° phase-shifted counterpart of the tracked signal, a peak amplitude appears in the tracking time window. A lowpass filter circuit averages this 90° signal over select-time windows, yielding a narrow-band output representing signal strength in the vicinity of the tracked zero-crossing. Computer selection of the phase signal to be tracked allows the tracking circuitry to move forward and backward in delay time through 90° phase increments. Thus, the computer can access and track almost any peak or zero-crossing in the ultrasound waveform. This tracking circuitry in the lower portion of the diagram is repeated six times (including the one repetition drawn), to track near- and far-wall depths for the three ultrasound angles generated by transmissions and receptions of the two ultrasound assemblies, 62 and 65 (FIGS. 2 and 3).

The echo depth signals generated by repetitions of the lower circuitry in FIG. 7 are designated N1 through N6. The signal strength voltages are designated M1 through M6. These signals all enter the "Computer Input Interface" assemblies illustrated in FIG. 9. Here, the "N" signal voltages are filtered, and these plus the already-filtered "M" signals are sampled and digitized for input to the computer as non-vibrational ultrasound dimension and signal strength data. In addition, the "N" signals are processed for audio-band vibration content, yielding narrow-band demodulated phaser signals representing 0°-phase and 90°-phase components of common-mode and differential-mode depth vibrations.

In the circuit diagrams, all input-only connections are marked by arrows pointing into circuit modules. The absence of an arrow means that a connection is an output or is bi-directional. All contiguous branches of a wire within a diagram are designated by a single number. Interconnection points for jumps between regions within a diagram or between diagrams are designated by labeled circles, whose numbering is kept the same at all repetitions of the circle symbol. Wire numbers change for non-contiguous regions joined by circles. In FIG. 8, waveform traces are labeled with the number or numbers of all wires or interconnects of FIG. 7 that carry the illustrated signal voltage. The horizontal axis in FIG. 8 is time.

Examining FIG. 7 in detail, we begin with clock input 200, designated CK, from the computer. This input travels via wire 201 into sequencing circuit 202, labeled SEQ. This digital circuit contains a counter that starts at zero and counts upward on clock pulses, timing all the processes of a complete ultrasound data acquisition cycle. Upon reaching a full count, the counter resets to zero and starts a new cycle. To generate the output waveforms, multiple-input gating circuits monitor the counter and recognize specific counts where waveform transitions are to take place. The outputs of these count-recognition gates trip appropriate flip-flop circuits, whose outputs are the timing waveforms. Sequencer circuit details, not shown, are easily provided by digital circuit designers.

In FIG. 8, the beginning of a full acquisition cycle is marked by arrow 400 and the associated dashed line extending below, while the termination of that cycle and the beginning of the subsequent cycle is indicated by arrow 401 and the associated dashed line below. The FIG. 8 waveforms include: sequencer outputs 211, 203, 276-277-315, 278-279, 280-281, and 265; timing ramp 225-264-310 triggered by the sequencer; pulses 268-269-330, 270-271, 272-273, 274-275, 402, and 403, associated with the times of ultrasound waveform zero-crossings being tracked; and display intensity control waveform 267. The sequencer cycle consists of three sub-cycles, corresponding to ultrasound pulse generation and reception for the three ultrasound paths. A binary select signal on wire 203 (FIG. 7) and trace 203 (FIG. 8) enters coaxial cable 204, which is part of cable assembly 2. This signal controls the switching circuits in sub-assembly 56 of assembly 1 (FIGS. 2 and 3, only the physical location of the sub-assembly shown) that select one of two impedance-matching transformer secondary windings (as designated) for coupling via coaxial cable 205 (FIG. 7) of cable assembly 2, thus determining which of ultrasound transducer assemblies 62 and 65 (FIGS. 2 and 3) is accessed. A low logic level on wire 203 selects transducer assembly 62 and its matching transformer for coupling to cable 205 and wire 209. A high logic level selects assembly 65 and its matching transformer instead. The high logic levels on trace 211 (FIG. 8) mark pulse transmit times, while the low logic levels mark echo receive times.

Following traces 203 and 211 together from arrow and dashed line 400, ultrasound assembly 62 is initially selected (203 low) to transmit a pulse (211 high), and remains selected (203 low) to receive the echo (211 low). At the end of the first sub-cycle, transducer assembly 65 is selected (203 high) to transmit a pulse (211 high) and receive the return echo (211 low). This time, assembly 65 remains selected (203 high) to transmit another pulse (211 high), but assembly 62 is immediately coupled (203 low) to receive the echo (211 low). Thus, the third timing sub-cycle is for a transverse echo signal from assembly 65 down to the artery and back to assembly 62. The cycle concludes at dashed line 401, and a repetition begins.

Wires 206 and 207 connect the shields of cables 204 and 205 together and to ground 208, completing the FIG. 7 connections associated with cable assembly 2. Wire 209 carries bi-directional ultrasound signals to terminal B of solid state switch 210. Drive pulses traveling toward the transducer assembly are channeled from switch terminal A1 to terminal B, while echo signal voltages are channeled from terminal B to terminal A0. Only one of the two signal paths is activated at a given time, depending on a binary switch-control input designated S, whose signal arrives via wire 211 from sequencer 202. When the logic signal on wire 211 (see also FIG. 8) is driven high by sequencer 202, terminal A1 of switch 210 is to be connected to terminal B. The positive transition of the signal on wire 211 initiates the generation of a pulse from "PULSE GEN" 212, which travels via wire 213 to "SHAPE FILT" 214, which modifies the shape of the pulse. This modification pre-compensates for linear phase and amplitude "distortions" (commonly so-called, although rigorously they are linear transformation phenomena) of the ultrasound transducer assembly, resulting in a substantially phase-linear ultrasound pressure waveform with smooth band-limiting. This substantially minimizes acoustic output pulse duration within the constraints of transducer bandwidth and amplifier power bandwidth. The pre-compensated electronic waveform is somewhat spread out in time, largely because of phase and amplitude distortions that anticipate offsetting transducer effects. Thus the acoustic pulse duration from the transducer is effectively shorter than the pre-compensated pulse duration emerging from filter 214 via wire 215. The shaped pulse travels via wire 215 to the input of amplifier 216, labeled "PWR" for power amplification. The output signal of amplifier 216 passes via wire 217, through termination resistor 218, and from the far side of the resistor via wire 219 into terminal A1 of switch 210. The termination resistor provides impedance matching to cable 205 to minimize signal reflections. (To save amplifier power, output series resistor 218 can be reduced, while feedback modifications result in an unchanged effective output impedance at wire 219. The voltage differential across the reduced series resistor is applied as negative feedback to the amplifier input. The detailed circuit involves a differential-input amplifier plus several input and feedback components. Triangle symbol 216, like other labeled triangle symbols in FIG. 7, designates both a voltage amplifier and associated input and feedback components. By contrast, triangles 336 and 355, labeled only with "+" and "−" signs to designate inverting and non-inverting inputs, are simple operational amplifiers whose input and feedback components are shown explicitly.)

When a pulse output period is complete, the sequencer output on wire 211 goes to a low logic level, causing terminal B of switch 210 to connect to terminal A0, thereby connecting wire 209 through the switch to wire 220. Wire 220 connects to termination resistor 221, whose far side is connected via wire 222 to ground 223. The reflection-minimizing function of resistor 221 during signal reception is analogous to the function of resistor 218 during pulse transmission. Wire 220 also couples the received signal to the signal input terminal of amplifier 224, labeled "AGC" for Automatic Gain Control. Typically, amplifier 224 will include more than one gain stage, to amplify very low-level input signals. (To minimize signal power loss and improve signal-to-noise ratio, it is possible to increase the value of resistor 221 and re-establish the original effective termination resistance using negative feedback. After increasing resistor 221, wire 222 is disconnected from ground 223 and reconnected to the output of an inverting, fixed-gain input amplifier stage in 224. A small capacitor paralleling reconnected resistor 221 may be provided to compensate for the effect of first-stage amplifier frequency response rolloff, to maintain a resistive termination impedance to wire 220. Gain control and frequency response compensation must be performed in one or more separate amplification stages following this impedance-synthesizing, low-noise input stage. The details will be apparent to those skilled in the art.)

The signal amplification to the output of amplifier 224 varies as a function of the voltage signal arriving at its gain control input via wire 225. A linear voltage ramp on 225 (see trace, FIG. 8) causes amplifier gain to increase progressively during an echo reception period. This ramp, generated by module 226, labeled "RAMP", is reset and held at zero by high logic levels arriving at the input to 226 via wire 211, from sequencer 202. The downward transistion of signal 211 initiates the ramp. The gain control response in 224 to ramp voltage 225 is tailored to minimize the signal-strength sensitivity at output on wire 227 to ultrasound depth. The signal on wire 227 is applied to the input of filter 228, labeled "SHAPE FILT". This filter functions like filter 214, to compensate for the linear phase and amplitude distortions of the ultrasound transducer assembly operating in receive mode. Since these "linear distortions" (i.e. amplitude-independent alterations of amplitude and phase as a function of frequency) of signal reception are substantially identical to the distortions of signal transmission (because of the transmit-receive symmetry of transducer characteristics), complete shape compensation requires two repetitions of essentially the same compensating filter. Both filters could be placed in series (or functionally combined) on either the input or output side of the circuit, but splitting the filter function between input and output circuits maintains a more uniform signal energy spectrum in the transmit and receive paths. (The functions of the shape filters could be time-shared using only filter 214, coupled as shown only during output pulses, with filter 214 output connected to both wires 215 and 229. The input is switched from wire 213 to wire 227 during echo reception periods, using a switch e.g. of the type of switch 210, controlled by the logic level on 211. This variation on the design shown in FIG. 7 functionally replaces precision filter 228 by a low-cost transistor switch.)

The ultrasound echo signal, now fully compensated for optimum depth resolution, travels via wire 229 into linear network 230, labeled "$\phi$", the Greek "PHI", symbolizing phase angle. The network produces two complementary output signals whose labeling, "0°" and "90°", indicates the relative phase-angle responses approximated over the ultrasound passband. Over the passband, the amplitude-versus-frequency responses of the two outputs are approximately flat. To generate such complementary phases with flat amplitude response requires a network having some effective time delay from input to output. This time delay, technically called group delay and defined as the derivative of input-output phase shift with respect to frequency, is kept substantially constant over the frequency passband, while amplitude and relative-phase errors are simultaneously minimized.

There are several possible approaches to implementing network 230. For example, an uncomplicated prototyping approach, effective at frequencies where active filter circuits present problems, is implemented using passive allpass filter stages consisting of capacitors and tapped inductor coils. These stages are decoupled by broadband amplifiers for tuning and adjustment with minimal interactions. Amplifiers are also used to compensate for coil resistances, allowing more precise allpass filter realizations. Using this approach, with computer transfer function analysis and optimization routines to specify filter design parameters, a pair of matched delay filters is implemented, each giving flat amplitude and matched, constant group delay response in the passband, but with a fixed 90° phase differential between the two outputs. This approach is "traditional" and familiar to many designers.

Several alternative approaches show promise of reducing costs, compared to the approach just described. They typically involve electronic means for delaying the signal and achieving a weighted average of the recent time-history of the signal—more technically, a convolution integral. The 0° output is derived from a single delay line tap, at the midpoint. The 90° output uses a weighting function resembling a truncated rectangular hyperbola, with the weighting becoming large near the center-tap delay. (The weighting process is an approximation of the Hilbert Transform.) The weighting can be positive for delays less than the center tap delay, and symmetrically negative for delays exceeding the center tap delay. This weighted average description sheds light on how the filters behave. The 90° signal output shows a positive peak at about the time when the 0° signal output shows a positive-sloping zero crossing. This property is used to track a zero crossing of one signal and use the simultaneous peak of the quadrature signal as a measure of signal strength at that point. This property also permits computer-controlled phase switching to alter the waveform point being tracked.

Three examples of suitable implementations of a tapped signal delay are given. One approach is a center-tapped electromagnetic delay line, consisting of a long solenoid wound on a grounded cylinder, creating a distributed inductance with a distributed capacitative shunt to ground. The ground can be a foil, etched into two complementary regions whose relative circumferential widths differ as a function of length along the solenoid. The foil pattern shape thus becomes a weighting function of the displaced charge. Differential amplification and integration of the current from the two foils results in a time-history-weighted average, or convolution integral. A second approach uses a charge-coupled analog delay device, or "bucket brigade" delay, with multiple taps. Weighting resistors and summing amplifiers achieve the desired weighted time history. Hardware for this purpose may perform poorly above 1 to 3 MHz, limiting its usefulness for high ultrasound frequencies. A third approach, the "crystal filter" approach, uses piezoelectric transducers and acoustic delay through a solid or along the surface of a solid. Once developed for a given application, crystal filters can be inexpensive to manufacture.

The 0° signal from filter 230 is interconnected to remote diagram points via wire 239 and through interconnect circle 240, labeled "U0" (for Ultrasound, 0°-phase). The signal on wire 239 is inverted by amplifier 241, resulting in the signal carried via wire 242 to interconnect circle 243, labeled "U180" for "Ulrasound, 180°-phase". The 90° signal travels via wire 244 to interconnect circle 246, labeled "U90⇌", designating the 90° ultrasound signal. Wire 244 also provides input to inverting amplifier 247, whose output travels via wire 248 to interconnect circle 249, labeled "U270", designating the 270° ultrasound signal. Both inverting amplifiers 241 and 247 are labeled "−1", indicating a configuration to achieve a gain of −1 over the ultrasound bandwidth. The circuitry described results in a symmetric group of four ultrasound signals, equally spaced around a 360° phase circle. Cyclic permutations of these four signals can be used to move phase-lock circuitry in controlled increments over the bumps, zero-crossings and dips of the ultrasound signal, accessing virtually all resolvable ultrasound data for computer pattern recognition and analysis, and then tracking the most significant depth signals for continuous vibration analysis.

For display purposes, the ultrasound signal on wire 239 is applied to a positive-gain input, marked "+", of amplifier 261, labeled "SUM". The select signal of wire 203 (see FIG. 8 for the waveform) enters the negative-gain input, marked "−", of amplifier 261. The resultant "sum" signal (actually a voltage difference), travels via wire 262 to the vertical deflection input, "V", of oscilloscope display assembly 263, labeled "SCOPE". The sequencing voltage on wire 203 provides vertical separation of alternating traces 13 and 14 (shown also in FIG. 1), producing upper trace 13 when the voltage on 203 is low, and lower trace 14 when the voltage on 203 is high. Ultrasound echoes on wire 239 appear as small sinusoidal wave packets, typically resembling a sinusoid modulated on and off by a Gaussian envelope whose standard deviation half-width is less than one sinusoidal period. Multiple echoes may cause these wave packets to overlap, producing more complex waveforms than those illustrated. Horizontal deflection is provided by the ramp voltage on wire 225 entering oscilloscope assembly 263 at "H". This voltage on wire 225 also goes to interconnect circle 264, labeled "R", for Ramp. A blanking signal is provided by sequencer 202 on wire 265. This signal passes via a positive-gain input into SUMming amplifier 266, labeled "SUM", then from the amplifier output via wire 267 to Intensity input "I" of oscilloscope module 263. When the signal on 265 is low (see trace, FIG. 8), the oscilloscope trace is blanked, either for retrace during the drive pulse period, or for the transverse echo period, since the transverse echo trace is not displayed. The tracked portions of traces 13 and 14, namely segments 15, 16, 17 and 18 on the display, are highlighted, respectively, in response to pulses appearing at interconnect circles 268, 270, 272 and 274, corresponding respectively to labels "I1", "I2", "I3" and "I4". In the same order, interconnect wires 269, 271, 273 and 275 go to summing inputs of amplifier 266. Traces for these signals are shown in FIG. 8. The summed output on wire 267, as shown in FIG. 8, causes blanking at the lowest level, a normal trace at the intermediate level, and highlighting at the upper level.

The sequencer generates Select signals which travel from the sequencer via respective wire 276, 278 and 280 to respective interconnect circles 277, 279 and 281, labeled "S1", "S2" and "S3". As seen on the traces in FIG. 8, these signals are high during the echo reception periods for the three ultrasound paths. The "blank when low" signal on sequencer output wire 265 is seen to match the Boolean logic expression "S1 OR S2", i.e. high when either or both of S1 and S2 are high. Each of S1, S2 and S3 is used to gate two separate phase-lock circuits like the one illustrated below the dashed line in FIG. 7, giving a total of six such circuits. For one group of three circuits associated with S1, S2 and S3, the signals U0, U90, U180 and U270 are connected to multiplexer 290 as shown in FIG. 7. For the other group of three, the "U" signals are interchanged in polarity, which amounts to a cyclic permutation of two steps around the group of four phase signals. Thus, U0 becomes U180, U90 becomes U270, U180 becomes U0, and U270 becomes U90. The six interconnection patterns just described are summarized in the labeling just below the dashed line on the right in FIG. 7, stating "REPEAT BELOW SIX TIMES FOR (+U or −U) and (S1 or S2 or S3)", i.e. for any combination of normal +U, or polarity-interchanged −U, signals, with any one of S1 or S2 or S3. The resultant tracked time-window signals I1 through I6 are numbered, respectively, I1, I3 and I5 for S1, S2 and S3 with +U, and I2, I4 and I6 for S1, S2 and S3 with −U. Of these six, only I1 through I4 are used for oscilloscope trace intensification. Numberings for delay-time signals N1 through N6, and for magnitude signals M1 through M6, match the numbering just described for I1 through I6.

Following the particular circuit repetition shown below the dashed line in FIG. 7, the four ultrasound signals labeled "U0", "U90", "U180" and "U270", from respective interconnects 240, 246, 243 and 249, pass via respective wires 291, 292, 293 and 294 into MultipleXer 290, labeled "MUX". Multiwire computer bus 295, via interconnect circle 296 from the ComPUter and labeled "CPU", couples into multiplexer 290. Under computer control, the multiplexer selects two of the four inputs for connection to output wires 297 and 298, respectively labeled "U'0" and "U'90". (The apostrophe designates "primed"). In a nominal setting, U0 connects to U'0, and U90 to U'90. The computer can move the phase-lock point along the ultrasound waveform in 90° jumps by cyclic permutation of the U0, U90, U180 and U270 connections to U'0 and U'90. Thus, connecting "U90" to "U'0", and "U180" to "U'90", will move the phase-lock point 90° earlier in the waveform.

The selected ultrasound signals U'0 and U'90 are used in conjunction with the following circuitry. Ramp interconnect circle 264, labeled R, is coupled to wire 310, leading to the inverting "−" input of comparator 311 and to the non-inverting "+" input of comparator 312. The respective comparator outputs, on wires 313 and 314, are coupled to inputs of AND-gate 316. The output of this AND gate can go high only when both comparator outputs are high simultaneously. As a further restriction, the select signal S1, coupled via interconnect circle 277 and wire 315 to an input of AND gate 316, must also be high to enable the AND output. For S1 high, the AND condition is satisfied whenever voltage R on 310 is below the voltage on 320 and above the voltage on 321, i.e. in a "window" defined by these latter two voltages. The voltage on 320 couples to the non-inverting "+" input of comparator 311, and when it exceeds the voltage on 310, the output of 311 on 313 goes high. The voltage on 321 couples to the inverting "−" input of comparator 312, and when it falls below the voltage on 310, the output of 312 on 314 goes high. The voltage window below voltage 320 and above voltage 321 is centered about a voltage that is a fixed fraction of the voltage on feedback wire 317 (which is seen looping over the top of the entire circuit below the dashed line). This feedback voltage, labeled "N1" at interconnect circle 338 (lower right corner of diagram), is the ultrasound depth signal. The fixed large fraction (typically exceeding 0.95) of voltage N1 that defines the window center voltage is given by the resistor ratio R322/(R322+R318), where the resistor R-numbers correspond to the diagram numbers. The circuit design calls for R323=R322, and R319=R318. Bias voltages +V and −V, being fixed positive and negative voltages of equal magnitude, define the width of the voltage window, after scaling by the four resistors just mentioned. Specifically, the voltage width is 2·V·R318/(R322+R318). This voltage width, in combination with the slope of ramp signal R from module 226, defines a window time width. The time width is typically chosen to correspond to a 90° phase change at the ultrasound center frequency. The ultrasound propagation delay time depends on the fixed large fraction of voltage N1 mentioned above, and on the slope of the ramp signal, R.

Specifically, the voltage window is defined by the series connection from +V interconnect circle 326 to wire 324 to resistor 322 to wire 320 to resistor 318 to wire 317 to resistor 319 to wire 321 to resistor 323 to wire 325 to −V interconnect circle 327. The center voltage on this string is driven by voltage 317 from amplifier 336 (on the right). The connections to comparator inputs from wires 320 and 321 complete the window implementation. When voltage R passes through the window, a pulse may be generated, centered at the time delay that is required for the ramp signal to cross the window voltage. The pulse is only generated when select signal S1 is high.

The time window caused by the passage of the ramp voltage through the voltage window is the duration of the positive logic pulse illustrated in FIG. 8, on the trace numbered 268, 269 and 330 for the three appearances of this voltage in FIG. 7. This pulse highlights segment 15 of the oscilloscope display. When select signal S1 is high, the output pulse of AND-gate 316 is coupled via wire 330 to transistor switches 331 and 332 at the inputs labeled "S". For each switch, terminals A1 and B are connected during the window duration. In switch 332, the effect of this connection is to couple signal U'0 from wire 297 briefly to wire 333, the input wire to an inverting integration circuit. The integrator is built around operational amplifier 336, with input resistors 334 and 342, and feedback capacitor 337. The non-inverting "+" input of amplifier 336 is grounded at 340 via wire 339, so that 336 acts like a very high gain inverting amplifier. The output of 336, on feedback wire 317, is depth signal voltage N1. This output wire connects via feedback capacitor 337 to input-junction wire 335, going to the inverting "−" input of 336. Ends of input resistors 334 and 342 join to wire 335, while the opposite ends of the resistors are respective input signal wires 333 and 341.

When no current is allowed to flow through integrator input wire 341, the integrator responds only to the U'0 input signals connected from 297 to 333 during time windows determined by AND-gate 316. If the windowed, highlighted segment 15 of the ultrasound waveform (see oscilloscope display 4) is symmetric about 0 volts, the net increment in integral N1 over the duration of a select window pulse on I1 will be zero. If the average value over the window duration is non-zero, a net increment in integral N1 is generated, negative if the average value is positive (since the integration is inverting in polarity). Moving the window to the right in trace 13 results in a positive average over the window segment. The resulting accumulating negative increments in integral voltage N1 move the voltage window to a lower point on ramp R, resulting in an earlier appearance of the window on subsequent pulses. Thus a self-correcting loop is established that tracks the positive-going zero crossing. The same loop will avoid negative-going zero crossings. Interchanging multiplexer 290 inputs U0 with U180, and U90 with U270, will cause the circuit to track negative-going zero crossings. The integration time constant determined by input resistor 334 and feedback capacitor 337 is made short enough to assure tracking of vibrational and pulsatile arterial motions with minimal time lag, but not so short as to compromise loop stability. Note that the speed of the tracking loop varies with the slope of the tracked zero-crossing. The loop must therefore operate over a range of signal strengths.

Cyclic permutations of the input-output connections in multiplexer 290 shift the phase-lock point by 90° jumps. Permuting the U-inputs "forward" by +90° replaces a tracked positive-sloping zero crossing of U'0 by a positive peak of U'0 in the select time window. Sampling and integration of this positive peak causes a negative change in inverting integral voltage N1. This moves the select window earlier, to a positive-sloping zero crossing of U'0. The effect is to reposition window 15 on trace 13, which still displays signal U0, not reselected signal U'0. The highlighted segment 15 will now lie on a negative peak of U0. Backward permutations of multiplexer interconnections will move the tracking point to a later time in the U0 waveform.

In a flat region of the ultrasound echo trace, the computer becomes unable to move the select time window in the phase-jumping manner described, since there is no signal slope to generate a feedback signal. Therefore, the computer causes the window to drift positively or negatively, corresponding to greater or lesser delay into a pulse cycle, by applying a negative or positive voltage via interconnect 296 and wire 341 to integrator input resistor 342. When no drift is desired, the connection to wire 341 from within the computer is interrupted by transistor switching.

The magnitude signal M1, at interconnect 360, is derived by gating of the U'90 signal in switch 331, and by filter circuitry. When U'0 tracks a positive-going zero crossing, U'90 has a positive peak in the same window interval. This peak region on wire 298 is sampled by switch 331, which connects the voltage from A1 to B, and from wire 298 to 350. Resistor 351 represents the input to a unity-gain, two-pole lowpass filter.

In calculating the filter transfer function, the value of resistor 351 must be divided by the on-state duty cycle of switch 331. On the opposite end of resistor 351 from wire 350 is wire 352, which is connected in turn to resistor 353. The opposite end of resistor 353 leads via wire 354 to the non-inverting "+" input of operational amplifier 355, and to one side of capacitor 356. The opposite side of capacitor 356 is grounded via wire 357 to ground 358. The output of amplifier 355 feeds back via wire 359 to the inverting input, creating a unity-gain voltage follower, so that the potential of 359 tracks the potential of 354. It will be seen that grounded capacitor 356 in conjunction with resistors 351 and 353 creates a single-pole lowpass filter, whose output is buffered by the op amp. The output voltage on wire 359 is coupled via capacitor 361 to wire 352, which joins resistors 351 and 353. This capacitor feedback path introduces a second pole into the filter function, plus mild positive feedback around the loop. This feedback can be used, through proper component selection, to implement a two-pole Bitterworth filter characteristic. This well-known filter function combines moderately sharp frequency cutoff with good phase linearity and fast settling. Because of the high ultrasound repetition rate and the low output bandwidth required, a higher-order filter is unnecessary for removing pulse-rate "jitter" from the filtered output. The implementation of the Butterworth filter function with this topology is familiar to electrical engineers. The filtered output appears on interconnect circle 360, labeled "M1".

By circuit repetitions described, voltages N1 to N6 represent propagation delay times for selected portions of repetitive ultrasound echo traces. Voltages M1 to M6 represent the ultrasound signal strengths in the vicinity of the selected trace portions. The computer can adjust circuit phase-lock to almost any portion of an echo trace that has a zero crossing in one of the signal phases generated by filtering. Trace portions that may fail to track are regions of very low signal amplitude or poor signal-to-noise ratio, or regions where time-varying interfering echoes create signal slope reversals. To minimize artifacts of multiple-reflection interferences, and simultaneously to assure phase lock to opposing artery walls in the vicinity of maximum vibrational response, the computer seeks a strong signal region to track, with high differential vibration amplitude. Specifically, it tries all possible pairs of tracking points that fall within a physiologically-possible range of depth and spacing, and it selects for tracking the pair that maximizes the product of signal strength and differential vibration amplitude. Since the polarities of echoes from near and far arterial walls are reversed if the walls are symmetric (because transitions to greater acoustic impedance on the near side correspond to transitions to lower acoustic impedance on the far side, and vice versa), the tracked slopes of near and far walls are normally opposite, and may be as shown for segments 15, 16, 17 and 18, or the reverse, with negative tracked slopes on the left and positive tracked slopes on the right, depending on arterial wall structure and polarities of the ultrasound system itself. Assymmetries in the artery may cause the system to track same-slopes rather than opposite-slopes, or to track different slope signs for different echo paths. Although the system is designed so that tracked optimum waveform points are normally displayed as zero-crossings, the system may track zero-crossings in a 90° or 270° phase signal, meaning that the displayed highlighted segment may be a maximum or minimum peak. This choice could arise from variations in the overlap of echo contributions from closely-spaced ultrasound reflectors. These variations in phase tracking choices do not necessarily imply unsuccessful functioning of the overall system. The operator must be alert to assymmetries in the display, however, since these may imply arterial wall irregularities that could cause errors in analyses based on some degree of radial symmetry, at least of the artery wall and immediate surroundings. The system may be programmed to note assymmetries as it scans to select tracking echo depths, and to alert the operator to assymmetries exceeding threshold limits. The operator can respond to observed trace irregularities or to system prompting by repositioning transducer assembly 1 over a healthier, more uniform artery segment.

Referring now to FIG. 9, we see how these ultrasound signals are interfaced to the computer. The signals are used directly (except for lowpass filtering) for signal strength and depth data, and indirectly, as demodulated vibration signals. Driver force and acceleration signals are also processed for digital force and velocity input.

The acceleration signal arrives via cable 2 as a balanced signal from a strain gauge bridge in assembly 1. It arrives at interconnect circle 420, labelled "AC" for ACceleration. Wires 421 and 422 carry the differential signal from circle 420 to the inverting "−" and non-inverting "+" differential inputs of amplifier 423, labeled "INS" for INStrumentation amplifier, an amplifier designed for precise feedback-controlled gain with very high common-mode signal rejection. This is useful for rejecting hum and interference signals that usually appear as a common-mode voltage on a symmetric twisted pair of wires.

The single-ended voltage output of amplifier 423 on wire 424 provides input for module 425, labeled "BPF/s". The letters "BPF" designate the BandPass Filter function that is repeated for every vibration input, in order to standardize frequency-dependencies of amplitude and phase and cause these dependencies to cancel upon complex-number division by the reference velocity signal. The phase-correction aspect of the complex division takes place in the demodulators using the velocity reference phase, while the magnitude-correction aspect takes place digitally, in the computer. The "/s" aspect of the "BPF/s" filter label represents integration with respect to time, which is needed to transform the acceleration signal to a velocity signal. In the Laplace transform domain, integration becomes division by the transform variable "s". Hence, the "BPF/s" filter labeling is chosen to designate a transfer function combining integration with bandpass filtering, using notation familiar to electrical engineers. Since electronically-derived integrals inevitably drift over time, it is useful to combine integration with filtering that cancels drift in a single combined-function filter. In this way, the overall desired filter function is achieved without compromise. Using similar notation, filters 455 and 466, at the top of the figure, are labeled "BPF·s". In the Laplace domain, multiplication by "s" represents differentiation with respect to time. As with integration, practical considerations prevent separate circuits from performing time differentiation except over limited bandwidths. Since high-frequency gain reduction is an aspect of the BPF filter function, a single filter circuit combining bandpass filtering with differentiation is feasible. The critical feature about these filters is matching of the bandpass function. The filters just described are easily detailed by electrical engineers.

Continuing with the output of filter 425 via wire 426, the continuous signal enters the "S" (Signal) port of demodulator module 429, (not to be confused with the Switching ports of modules 210, 331 and 332 of FIG. 7.) The operation of module 429 and the other demodulators in FIG. 9 was discussed under the heading "AC Signal Demodulation", where the module labeling is explained in conjunction with FIG. 6. Wire 426 also couples the hand-limited velocity signal to module 427, labeled "CLIP". This module clips the voltage swing of the velocity signal typically from a few volts to about 700 millivolts peak, on output wire 428, which extends up through the diagram to all the zero-phase demodulator reference inputs. The clipped amplitude is accurately in-phase with the velocity signal, and is insensitive to velocity amplitude variations. Wire 428 connects to the phase reference input of demodulator module 429 at the terminal labeled "O". The demodulator output from terminal "O" travels via wire 430 to multiplexer 444, labeled "MUX", and enters at the input labeled "V" (Velocity). As was explained earlier, there is only a zero-phase velocity signal, since the 90° signal is always zero. Module 431, labeled "PLL" (Phase Lock Loop), generates a square wave on output wire 432, which travels up to all the 90°-phase demodulator reference inputs. This signal is similar to the signal on wire 428, except that it leads the wire-428 waveform in phase by 90°. Phase lock loop circuits for generating quadrature-phase signals are familiar to electrical engineers. There are commercial integrated circuits easily adapted to achieving the frequency range and tracking speed requirements of module 431.

Like the acceleration signal, the vibration driver force signal appears originally as a low-level differential voltage from a semiconductor strain gauge bridge, conducted to interconnect circle 433, labeled "F" (Force), via a twisted wire pair in cable assembly 2. The pair ends at wires 434 and 435, which enter the inverting "−" and non-inverting "+" differential inputs of instrumentation amplifier 521, labeled "INS", like amplifier 423. The amplified, single-ended signal travels via wire 436 to amplifier 520, to an input labeled "+1" to indicate unity amplification. The acceleration signal on wire 424 from amplifier 423 is applied to an inverting input on amplifier 520, labeled "−e" (−error). The purpose of this input is to subtract from the force signal the mass-times-acceleration error signal associated with the moving mass of the transducer assembly. Thus, as explained earlier, the resultant force signal appearing an output wire 437 from amplifier 520 represents only the force actually applied to patient tissue. (This correction can easily be accomplished in computer software, working with the demodulated signals, but the circuit described offers greater conceptual clarity by generating "pure" signals.) Since only vibrational variations in the force signal are of interest, the signal on wire 437 is applied to module 438, labeled "BPF" (bandpass filter). Here the filter function need not be modified by differentiation or integration. The filter output from 438 travels on wire 439 to the signal inputs, "S", of demodulator assemblies 440 and 442. The phase reference input for demodulator 440 is the zero-phase reference on wire 428, while the reference for demodulator 442 is the 90°-phase reference on wire 432. The "real" component derived from the zero-phase demodulation in 440 travels via wire 441 to the input of multiplexer 444 labeled "FR" (Force, Real component). Similarly, the "imaginary" component derived from the 90°-phase demodulation in 442 travels via wire 443 to the input of multiplexer 444 labeled "FI" (Force, Imaginary component).

Processing of ultrasound depth signals is similar to processing of force signals, except that filtering includes time-differentiation to obtain velocity signals from the displacement signals. For near- and far-wall depth signals N1 and N2, arriving via interconnect circles 338 and 451, respectively, wires 450 and 452 conduct the respective signals to differencing amplifier 453, to inputs labeled "−1" and "+1" to designate inverting and non-inverting unity gain. (Recall that the N2 signal is generated by a repetition of the circuitry on the bottom of FIG. 7, but with opposite-polarity ultrasound "U" signals interchanged at the inputs of multiplexer 290). The difference signal from amplifier 453 is carried via wire 454 to filter module 455, labeled "BPF·s" to designate combined differentiation and bandpass filtering, as discussed above. Not indicated in the filter labeling is the modification in the filter function to offset the slight lag of the tracking loop circuit on the bottom of FIG. 7, generating N1, and the repeated circuitry generating N2. This compensation cannot be exact, since the tracking circuit responds with variable time lag according to signal slope, but the compensation is set for a typical ultrasound signal slope. Since the computer monitors the signal strength signals M1 through M6, which closely approximate the slopes of the tracked zero-crossings, it can compute phase and amplitude errors arising from slope values significantly different from the ones anticipated in the fixed filter compensations. The compensated signal from filter 455 travels via wire 456 to the signal inputs of demodulators 457 and 459. The phase inputs arrive, respectively, on wires 428 and 432, producing "real" and "imaginary" demodulated signal outputs on wires 458 and 460, leading to inputs of multiplexer 444 labeled "D1R" and "D1I" (Differential velocity signal number 1, Real and Imaginary components).

Common-mode depth velocity is interfaced to the computer in the same manner as differential depth velocity, except that the sum of signals N1 and N2 is processed instead of the difference. The N1 and N2 signals, on interconnect circles labeled 338 and 451, are coupled to wires 461 and 463, leading to summing inputs of amplifier 464. The "+1" labeling of both inputs indicates unity-gain summation. The sum, on output wire 465, goes to module 466, "BPF·s", whose function matches that of module 455 above, as mentioned. The filtered output on wire 467 travels to "S" inputs of demodulator modules 468 and 470, whose phase reference signals, O, arrive via wires 428 and 432. The "real" and "imaginary" demodulated outputs travel via wires 469 and 471 to inputs of multiplexer 444 labeled "C1R" and "C1I" (Common-mode velocity signal number 1, Real and Imaginary components).

The depth signals N1 and N2, and the corresponding magnitude signals M1 and M2, enter the multiplexer with less processing on the right of multiplexer 444, for non-vibratory signal processing. N1 and N2 inputs, via interconnects 338 and 451 as elsewhere, travel via wires 480 and 484 to modules 481 and 485, labeled "LPF" (LowPass Filter). These filters are typically both identical to the two-pole Butterworth filter illustrated at the bottom of FIG. 7, except for a changed input resistor, not corrected for input-switch duty cycle. The filtered outputs travel via wires 482 and 486 to inputs of multiplexer 444 labeled "N1F" and "N2F", where the "F" designates "Filtered". Magnitude inputs M1 and M2 are already filtered, and travel via wires 483 and 488 to multiplexer 444 inputs also labeled "M1" and "M2".

The N1, N2, M1 and M2 functions just described are repeated twice more, for N3, N4, M3 and M4, and finally for N5, N6, M5 and M6. As labeling in FIG. 9 indicates, this is accomplished by repeating the portion of the circuit between the dashed horizontal lines twice, in addition to the repetition shown, for a total of three repetitions.

We now examine computer control of multiplexing functions. The computer is indicated at box 500, labeled "CPU". The same label applies to multiwire bus interconnect circle 295, carrying signals to the multiplexer circuitry of FIG. 7 for control of ultrasound tracking selection. The bus in FIG. 9 is labeled 501 for its lower portion, leading to 295, to multiplexer 444, and to A to D converter 503. Information flow to the multiplexer, telling which analog input line to select, is essentially one way, as shown by the wide arrow pointing into the multiplexer. The selected multiplexer input is coupled to output wire 502, leading to the analog input of A to D converter 503. This converter module samples and digitizes the analog data for input to the computer at 500 via bus 501. The bus connection to converter 503 operates bidirectionally, since the computer sends data to 503 for timing of the sampling and conversion process, and the resulting digitized signals travel back from 503 to the computer.

Above computer block 500, wire 504 carries clock pulses to interconnect circle 200, "CK", which appears in FIG. 7, carrying timing pulses for the ultrasound event sequencer. Aside from synchronization to the computer clock, the event sequence of module 202 (FIG. 7) is typically autonomous from the computer.

Multiwire bus 505, carrying the same data and address information as bus 501, enters module 506, "DCO" (Digitally Controlled Oscillator). A frequency-controlling binary number is transmitted to 506, where it is stored on flip-flops between updates. The oscillator itself typically uses the well known "state variable" design approach of two integrators and an inverter wired in a loop, with degenerative/regenerative feedback regulation to achieve a desired AC output amplitude with very low distortion. Integrator time constants are modified by placing a complementary-MOS multiplying D to A converter in the input path of each integrator. The digital input value held on the flip flops then modifies the integration speed of both integrators, causing oscillation frequency to vary directly with the frequency-control number. The detailing of this module is easily accomplished by a skilled electronics engineer. The oscillator output is split into a balanced differential signal for transmission via wires 508 and 509 to interconnect circle 507, "VB", to the ViBraton driver in assembly 1. Transmission is via a twisted pair of wires in cable assembly 2 (wiring not shown). The differential drive is chosen to keep drive currents out of signal ground wires and to minimize electrostatic couplings, thus simplifying shielding and isolation of drive and data signals.

Calibration Cuff Function

Sphygmomanometer cuff 11 (FIG. 1) is used optionally to reduce the pressure differential across the wall of the artery segment-under-test (e.g. part of carotid artery 40) by a known, time varying amount, normally below diastolic pressure so that the artery does not collapse. Cuff pressure change should be slow enough to permit axial blood flow to and from the cuff region, with resulting artery diameter change and pressure-differential equilibration. Cuff pressure is varied in a pattern, e.g. sinusoidal, designed to minimize the correlation between cuff and blood pressure changes. Cuff pressure change and vibration-determined blood pressure change can be correlated over unequal numbers of complete cuff and cardiac cycles (e.g. 10 full cuff cycles and a simultaneous 15 full cardiac cycles). The unequal rhythms minimize unwanted correlations of the cuff rhythm with all harmonics of the cardiac rhythm. Departure of the correlation slope from unity indicates an error in vibration-determined pressure change, leading to a calibration correction.

DESCRIPTION OF A WHOLE-ORGAN EMBODIMENT

Figure 10A:
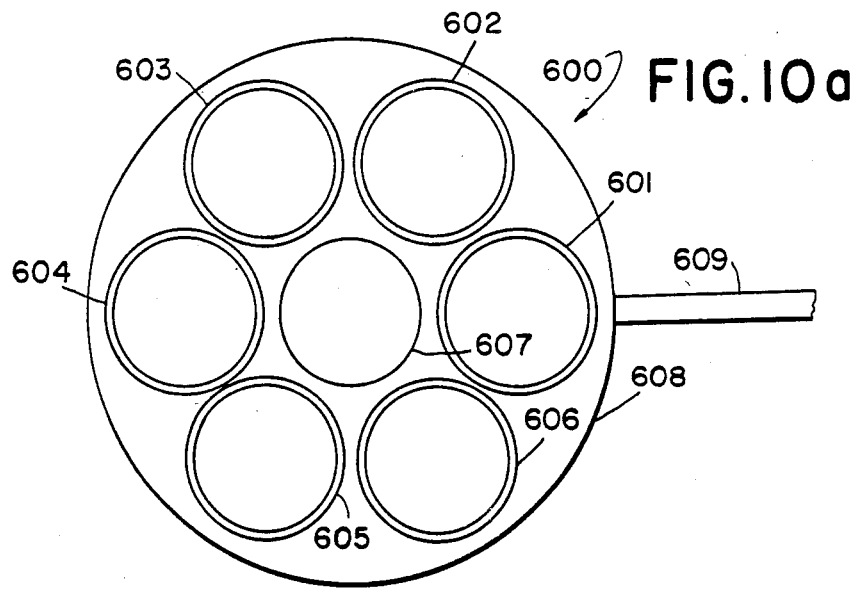
Figure 10B:
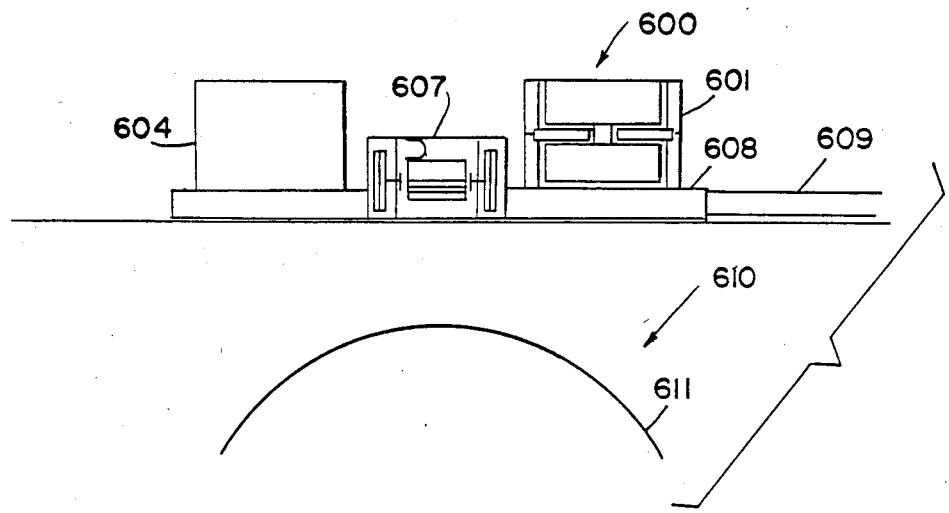
FIG. 10b is a side section view.

A variation of the invention is adapted e.g. for measuring mechanical properties of whole organs and internal pressures in fluid-filled organs, e.g. urinary bladder, or edematous organs. FIGS. 10a and 10b show that driver/sensor assembly 600 is a round disc with six driver assemblies, 601 through 606, arrayed hexagonally around the perimeter, and with single ultrasound assembly 607 in the middle. The six matched driver assemblies are each like the assembly of housing 60 and central moving element 61 of FIGS. 2 and 4. The description accompanying FIG. 4 applies to these driver assemblies as well. All six assemblies are wired electrically in parallel and generate parallel vibrational forces against disk 608, to which they are affixed. Driver/sensor assembly 601 is shown in simplified cross-sectional view in FIG. 10b, to clarify the orientation and relationship to the cross section of FIG. 4. Ultrasound assembly 607 (shown in FIG. 10b in simplified cross-section, to clarify orientation in the larger assembly) lies in the center of disk 600. The same cross section appears in more detail in FIG. 11. Interconnection to a computer/controller is provided by cable 609 (FIGS. 10a, 10b). FIG. 10b shows assembly 600 lying on the surface of tissue 610, with contour 611 indicating the upper boundary of an underlying organ.

In operation, assembly 600 is a three-dimensional-measurements counterpart to assembly 1 of FIGS. 1, 2 and 3. Assembly 600 is capable of sensing its vibrational velocity and the total vibrational force exerted on underlying tissue. The force measurement differs from assembly 1, which measures applied force only over a central transducer segment. The single ultrasound assembly of 600, lacking an acoustic lens, generates a roughly columnar beam, with the only significant divergence with depth arising from aperture diffraction. The beam has two-axis steering, which is servo-controlled to lock onto and track an ultrasound echo source over time.

An objective of the whole-organ embodiment is to induce vibrations in an underlying organ, and then to measure, over a range of frequencies, the surface mechanical impedance and the transfer ratios from surface driver velocity to velocities of various internal organ surfaces. The spectrum of responses is analyzed using simulation algorithms, as described below. The simulation outcome is a mathematical model of the vibrating system, with its coefficient adjusted so computed responses match observed responses. The adjusted model coefficients indicate the vibrational parameters of the organ tissue, including density, viscosity and shear modulus, and possibly including the frequency-dependences of viscosity and shear modulus, as these parameters may be influenced by visco-elastic creep. These parameters can be correlated with normal or pathological tissue conditions, e.g. the changes associated with scirrosis of the liver or with cystic kidney disease.

A further use of the whole-organ embodiment of the invention is to determine internal pressure in an organ, whether that pressure be attributed to free liquid or semiliquid contents, e.g. in the urinary bladder or the eye, or to abnormal fluid retention in cells or in the interstices between cells. The elasticity associated with a fluid pressure differential, whether abrupt across a thin organ wall, or graduated from the center to the surface of an edematous organ, gives a different series of vibration-mode resonant frequencies than is associated with an elastic modulus. This difference was discussed above in a cylindrical context for distinguishing blood pressure from arterial wall stiffness in the systemic artery pressure embodiment. Analogous differences exist for other organ shapes. The measurements and analysis taught here provide means for distinguishing fluid-pressure-related and elastic-modulus-related elasticities, even in heavily over-damped situations. Note that pressure-induced restoring impedance in a roughly spherical organ varies as the product of radius times pressure, whereas restoring impedance per-unit-length in a cylindrical organ or vessel varies as pressure alone, independent of radius.

Where fluid pressure effects vary over time between vibrational measurements, even slowly over hours or days, the change can provide pressure-baseline data, opening the way to the powerful network algorithm, for determining organ mechanical impedance. The three-dimensional network algorithm differs from the two-dimensional cross-sectional network algorithm primarily in depending on total surface-driver vibrational force, as opposed to a representative force per-unit-length. This difference accounts for the dissimilarities in the force measurement methods of this whole-organ embodiment versus the systemic artery pressure embodiment.

We now examine the steerable ultrasound assembly 607, shown from above in FIG. 11a, and from the side in FIG. 11c. Two possible magnetic field patterns for the perspective of FIG. 11a are illustrated schematically, side by side, in FIG. 11b. In FIG. 11a, we see a torroidal magnetic field generator surrounding a gimbaled center assembly. The field generator consists of four curved magnetic core elements 621 through 624, each mostly covered by curved winding segments 625 through 628. Each core element is a 90° segment of a torroid, and the wound elements abut to form a complete torroidal core. Opposite windings are joined electrically as pairs. Thus, windings 626 and 628 are wired to give a magnetic field across the torroid center, sloping from upper right to lower left, as illustrated on the left in FIG. 11b. Similarly, windings 625 and 627 are wired for a field from upper left to lower right, as on the right in FIG. 11b. Current reversals change the field directions. Within saturation, power and bandwidth limits, field strength and direction across the torroidal center can be controlled continuously by controlling currents in the two winding pairs.

Upper layer 630 of the gimbaled center assembly is an axially-poled, disk-shaped permanent magnet. Magnetic fields from the torroidal wound core generate torsional moments on the magnet, tending to align the magnet axis to the cross-plane field. The gimbal consists of jewel needles 631 and 632 (FIGS. 11a and 11c), extending inward from the torroidal core on the left and right; ring 633, seen from above (FIG. 11a) and in section (FIG. 11c), with bearing cups for needles 631 and 631; needles 634 and 635 (FIG. 11a only), extending inward from ring 633 above and below; and bearing cups for needles 634 and 635 in magnet 630. The gimbal permits the magnet to tilt in response to the driving magnetic field. Five thin, u-shaped spring wires restore the magnet to axial alignment, so that the equilibrium deflection angle is a function of applied field strength, and of temperature, which affects the magnetic moment of the permanent magnet. Of these five, wire 636 is illustrated in FIG. 11c. The five wires are arrayed with the openings of the u-shapes pointing radially outward to the vertices of an imaginary regular pentagon. Each wire is affixed to top assembly cover 640 and to magnet 630. These spring wires provide four signal leads for four 90° metallization sectors of piezoelectric ultrasound disk 641, plus a common ground lead. The sector metallizations are numbered 642 through 645 as they are exposed in the central cross-sectional view of FIG. 11a. These metallizations are on the top of ultrasound transducer disk 641, where the disk is affixed to magnet 630. The common ground metallization covers the entire lower surface of disk 641, which is bonded to quartz acoustic interface layer 650. This interface is in turn bonded to acrylic plastic acoustic interface layer 651, whose lower surface contacts fluid that envelops the gimbaled assembly. The fluid is contained in an envelope whose top surface is cover 640 and whose bottom surface is cover 652. Cover 652 forms the center of the lower surface of disk 608 (FIGS. 10a and 10b), and contacts the patient. The ultrasound impedance of the cover is close to that of the ultrasound-transmitting fluid and of human tissue, to minimize ultrasound reflections.

The ultrasound assembly is aimed using digital control. Algorithms regulate magnetic-drive field currents to produce desired aiming motions, taking into account magnetic torques, restoring torques, inertia and fluid-damping forces. The aiming mechanism as described here operates open-loop, to the extent that magnet angular position is calculated but not actually measured. Absolute angular accuracy of the device is not critical. Angle-correcting feedback comes when a desired ultrasound target is computer-identified and tracked, using circuitry like that shown below the dashed line in FIG. 7.

Angular error signals for alignment to center an ultrasound echo source are generated from the phase differentials of echo arrival at the four sectors of the ultrasound disk. Sectors closer to the echo source will give phase-leading echo responses, relative to sectors farther from the echo source. The disk is aligned when the four phases of the tracked signal match.

Circuitry to detect ultrasound phase error signals is outlined as follows. The same ultrasound drive pulse voltage is applied to all four sectors of disk 641. The return echo signal is received on two separate channels, split between either left versus right sectors, or up versus down sectors, depending on solid state switch settings. The split alternates left-right and up-down on alternate pulses. The two amplified channel outputs are summed to a common-mode channel, which is processed like any of the ultrasound channels of the systemic artery pressure embodiment, to permit tracking of a zero-crossing. The left-right and up-down differential signals are processed separately and sampled during the zero-crossing time window pulse generated by the tracking circuitry, like the pulse signal "I1" at 268 in FIG. 7. During the window interval, the tracked common-mode ultrasound signal is changing rapidly. The left-right and up-down differential ultrasound signals in the same phase and time window reflect the desired phase differentials. Both of these signals are sampled and smoothed like signal "U'90" on wire 298 from multiplexer 290 of FIG. 7. The sampled and filtered phase-differential signals are analogous to the signal "M1" at 360, in terms of the generating circuitry. The error signals represent a product of a non-linear phase error term multiplied by echo signal strength. The common-mode echo signal strength signal is used to correct the strengths of the alignment error signals, resulting in parameters that reflect angular misalignment in a consistent way. These misalignment signals are data for the algorithm that determines the currents to be sent to the torroidal magnetic driver. In this way, an alignment lock can be established as soon as a zero-crossing phase lock to an ultrasound feature is established.

The ultrasound system can scan its accessible angular sector and a prescribed depth range, recording the approximate three-dimensional locations of strong echo responses. Vibration responses are also noted. The array of responses is studied, possibly by human operators as well as the computer, and echoes representing desired vibration-tracking targets are identified. Those targets are subsequently re-located and tracked while driver frequency is varied. The vibration data for each target consist of target velocity and driver force, each resolved into 0° and 90° phase components relative to driver velocity. These parameters are typically expressed as ratios to driver velocity amplitude. The data are collected over an array of frequencies.

Force and velocity measurement for the whole-organ embodiment is different from the systemic artery pressure embodiment. Since total driver force is to be measured, rather than force from a portion of the driver, it is possible to infer force from the electrical responses of the electromagnetic vibration drivers, without using separate force and acceleration transducers. Velocity can be infrerred similarly. The inference is based on the driver coil voltage developed in response to element motion. When a driver reaction-mass element moves relative to the housing and driver plate, the magnetic fluxes linking the coils are altered. A fixed, rigid reference element, similar to the six driver elements, uses a secondary coil current to cause the same flux change that is induced by the average axial motion in the six driver elements. The secondary current necessary to balance the reference-element primary voltage against the voltage across the six drivers is a measure of displacement response. This measure is used to determine velocity and force response.

Figure 12:
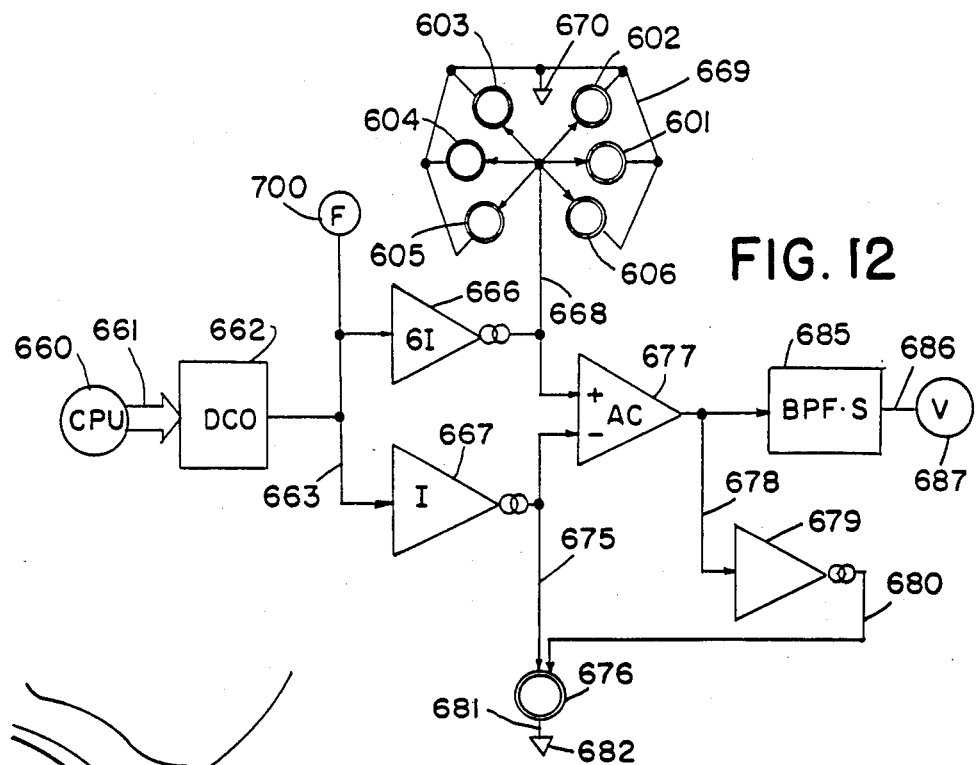
FIG. 12 is a block flow diagram of vibration-driver velocity measurement for the drivers of FIG. 10.

Implementation of this displacement-response measurement is detailed in the circuit diagram of FIG. 12. From interconnect circle 660, labeled "CPU" (computer), multiwire bus 661 carries a control signal to module 662, labeled "DCO" (digitally controlled oscillator). This oscillator is similar to module 506 of FIG. 9, previously described, except that the output is single-ended rather than differential. The frequency-controlled sinusoidal output is coupled via wire 663 to interconnect circle 700, labeled "F" (force). This signal, of known constant amplitude, provides the 0° phase reference signal for demodulation, as did the velocity signal on wire 426 of FIG. 9. A 90° phase-lock-loop uses this signal to develop a 90° phase reference signal for demodulation, as with the velocity signal in FIG. 9. Wire 663 couples to current amplifiers 666 and 667. The output of amplifier 666 is six times the current output of amplifier 667, and drives the six parallel-connected electromagnetic drivers, 601 through 606, as joined together and to amplifier 666 by wire 668. The opposite ends of the driver windings connect to wire 669, which is grounded at 670. The lower current of amplifier 667 is coupled via wire 675 to reference electromagnetic driver 676. This reference driver matches the other six except that the housing and central moving element are locked to fixed relative positions. The space occupied by o-rings in the other six drivers is occupied by a secondary winding in the reference driver. The difference between the reference-driver primary voltage and the voltage across the six parallel drivers is the voltage difference between wires 668 and 675. Wire 668 connects to the "+" input of high-gain AC differential amplifier 677, while wire 675 connects to the "−" input of the same amplifier. This amplifier includes high-pass input filtering and feedback to nullify DC input offsets while leaving operation at oscillator frequencies virtually unaffected. The greatly-amplified AC difference signal is coupled from 677 via output wire 678 to the input of current amplifier 679. The resulting current output is coupled via wire 680 to the secondary coil in reference-driver 676. Both primary and secondary windings in 676 have their opposite ends connected to ground wire 681, which is grounded at 682.

The function of the feedback loop through the secondary winding in the reference driver is to determine the average vibrational change in position of the magnet-plus-coil elements in the six parallel drivers, relative to the housings and center-washers. Position changes divert magnetic flux, inducing primary winding voltages proportional to rates-of-change of flux. The feedback loop through the reference secondary winding provides a secondary curremnt such that the AC magnetic flux imbalance in the reference driver almost exactly matches the average of the motion-induced flux imbalances in the six matched drivers. The secondary current needed to accomplish the primary voltage balance is an accurate measure of average relative position changes of the six moving driver elements. The close flux matching achieved between the reference driver and the average of the six moving drivers causes matched magnetic non-linearities and matched parasitic eddy currents, so that these artifacts are minimized in the feedback signal developed on wire 678.

The voltage on wire 678, representing vibrational position change, is coupled to the input of filter 685, labeled "BPF·s" (bandpass filtering combined with time differentiation, the latter indicated by the operator "·s"). This filter function was discussed in relation to the systemic artery pressure embodiment of FIG. 9. The output signal from filter 685 on wire 686 is coupled to interconnect circle 687, labeled "V" (velocity). This signal represents a relative average velocity of the driver housings and center elements. This signal is demodulated with respect to 0° and 90° phase reference signals, like the force signal on wire 439 of FIG. 9. The actual vibrational velocity of plate 608, and the force applied by plate 608 in underlying patient tissue, are deduced from the demodulated components of this "V" signal. The velocity- and force-determining formula of the computer takes into account the known reaction masses of the six drivers and the restoring characteristics of the support o-rings in the drivers. There is also a temperature correction factor, based on the temperature-sensitivities of the permanent magnets in the six driver elements. Temperature of the reference element is relatively unimportant. A temperature sensor on plate 608 provides a signal that is digitized and fed into the computer. The coefficients in the algorithm to determine velocity and force are adjusted by a calibration procedure in which the driver plate is placed against loads of known mechanical impedance and electrical responses measured at various frequencies.

DESCRIPTION OF AN OPTHALMIC PRESSURE EMBODIMENT

Another variation of the invention measures intraopthalmic pressure by inducing, measuring and analyzing vibration responses, and by measuring eyeball diameter. The system includes visual feedback from the patient to measure opthalmic vibrational motions. The computation system uses a simulation algorithm to interpret data. A network algorithm can also be applied under certain circumstances for refining and checking simulation results. Subsets of the data suffice to determine pressure with fair accuracy, but the combination of all the measurements taught here determine a more precise pressure.

Figure 13:
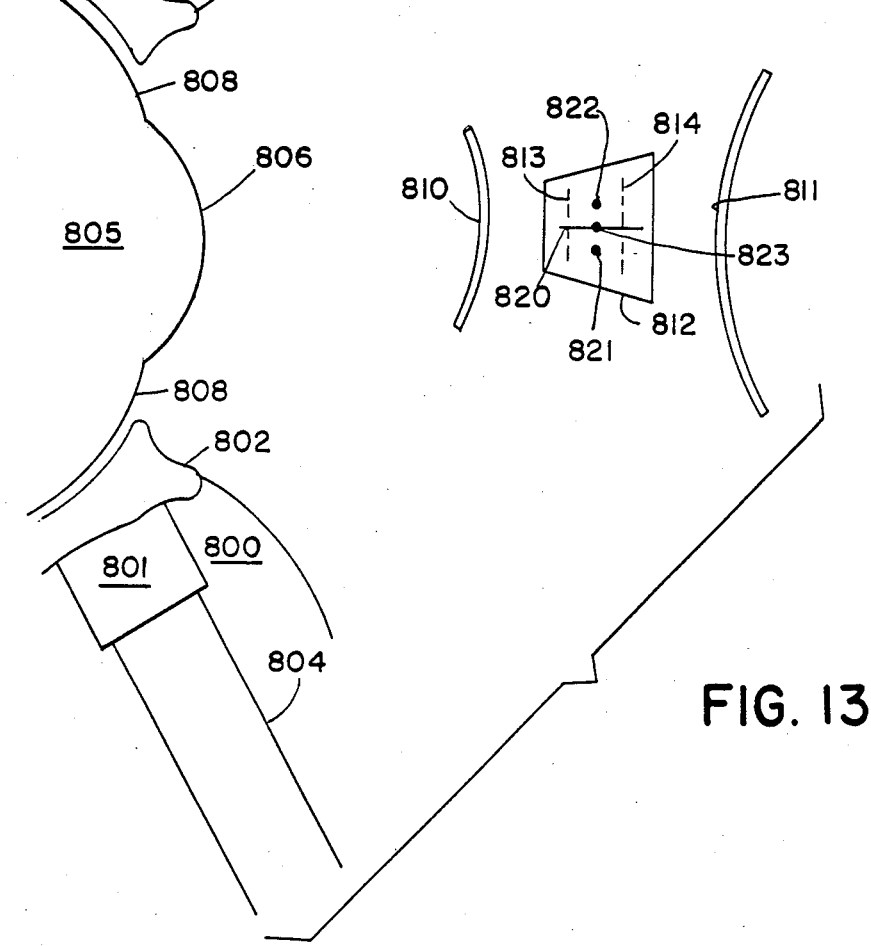
FIG. 13 is a diagrammatic representation of an intraocular pressure-measuring aspect of the invention.

Vibrational excitation plus surface-velocity and force sensing functions are combined in a single driver element. Vibration signal decoding electronics are very similar to the whole organ embodiment, as described with reference to FIG. 12. A single magnetic driver, 800 in FIG. 13, replaces the function of the six parallel-wired drivers 601 through 606 (FIG. 12). The reference driver is electrically matched to the moving driver, but locked against vibrational motion, as with the reference driver of the whole organ embodiment. The drivers are typically smaller than those used in the systemic artery pressure and whole organ embodiments, but are otherwise similar in design. Drive currents to the actual driver and reference driver are matched. Moving housing 801 of driver 800 makes direct contact with lower eyelid 802, including vibrations through the lid into the eye, shown generally at 805. The relatively heavy central winding and magnet structure is coupled to rigid supporting post 804. The post is achored in an adjustable support structure for resting the chin and ocular orbits in a stable position. When the head is steadied, post 804 is extended manually to bring housing 801 into gentle contact with the lower eyelid of the open eye. Post 804 is then locked in place for measurements. Velocity and force responses in the eye are deduced from electrical responses of the coil in driver 800, using a circuit similar to the FIG. 12 circuit. A difference is that the amplitude of the digitally-controlled oscillator drive signal is computer-controlled, as well as the frequency.

A first estimate of intra-opthalmic pressure can be derived using the mechanical driver response alone. At vibration frequencies well below the lowest resonant frequency (typically 30 Hz) of the eyeball, measured mechanical impedance reflects primarily the effective moving mass of the eyeball, moving substantially as a rigid sphere partly surrounded by a soft semisolid characterized by an additional moving mass, a velocity damping coefficient and a restoring constant. The coupling is through the lower eyelid, which behaves primarily like a spring at low frequencies. To better characterize the effective eyelid spring constant, vibration measurements are taken at higher frequencies between opthalmic resonances, chosen such that the eyeball behaves as a comparatively rigid body. These measurements complete, the driver explores vibrational impedance responses in the vicinities of low-frequency opthalmic resonances. Interpretation of the data depends on eyeball diameter, on the effect of partly-surrounding tissue mass (which varies with eyeball protrusion from the head) and on an average tissue density that varies little and can be guessed. The measurements well below resonance assist in estimating the effective vibrating mass of the tissue that partly surrounds the eyeball.

Interpretation of the mechanical vibration data is improved by a measurement of opthalmic diameter. The curvature of sclera 808 (the white of the eye) is measured by observing the reflections of two lights on the sclera. Lights 810 and 811 appear as narrow, curved line-sources of illumination, oriented roughly vertically to either side of a display screen. (The lights must typically be spaced further than 45° from the eyeball-to-display center axis to make the sclera reflections visible to the patient.) The curvature of the lights is chosen to make the reflections on the sclera to the left and right of cornea 806 appear approximately as straight vertical lines. Tests are conducted in a dark-walled booth, to minimize other reflections from the sclera. Clear display screen 812, between the two lights, is temporarily backed by a mirror. Vertical cursors 813 and 814 are generated just in front of the reflective mirror surface, e.g. using light-emitting diodes and fiber optics. Switching of light-emitting diodes on different fiber optic elements moves the visible cursor positions by small increments. The positions are adjusted by the patient controlling adjustment knobs, until the patient, looking in the mirror, sees the light reflections on the sclera aligned to the two cursors. The aligned cursor positions indicate the size of the eyeball. This size measurement refines the interpretation of the vibrational-impedance measurement, yielding an improved pressure estimate.

To obtain further vibration response data, the mirror surface on the back of screen 812 is replaced by a black surface. Lights 810 and 811 are switched off, as are the diodes illuminating cursor lines 813 and 814. The display now consists of strobed horizontal line 820, synchronously-strobed dots 821 and 822 above and below the center of line 820, and independently-strobed dot 823 in the middle of line 820. Peak strobe intensity must be fairly high, so that flash tubes are typically used for this function instead of light-emitting diodes. Line 820 is strobed in two alternating colors, e.g. red and blue-green. The strobe flashes are synchronous with the vibration drive signal, with (e.g.) the red and blue-green strobe times separated by a 180° relative phase angle. As the eyeball vibrates, the cornea tilts and causes the image of the strobe display to move up and down on the retina. When the patient observes the red-strobed line converged with the blue-green-strobed line to form an apparent white line, this indicates that the moving line image on the retina is crossing the same position, moving in opposite directions, at the times of the strobe flashes. The phase of the red flash (and consequently of the opposite-phase blue-green flash) is computer-set to a specific timing angle relative to the force computed to be effectively driving the opthalmic vibration mode of interest. The patient adjusts a knob that controls driver frequency (via the computer), in order to converge the red and blue-green strobe lines. Convergence indicates that the zero-crossings of the vibrational displacement of the cornea and lens are in-phase with the computer-controlled strobe-timing phase. By repeatedly resetting the strobe phase angle relative to computed vibrational force and allowing the patient to adjust frequency to reconverge the lines, the computer determines values for the opthalmic vibrational phase response angle as a function of frequency.

Dot 821 flashes blue-green with the blue-green flash of line 820, while dot 822 flashes red with the red flash of line 820. The apparent visual positions of dots 821 and 822 are not perturbed by vibrational motion when the colors of line 820 are converged. To measure angular response amplitude of the cornea and lens, dot 823 is strobed alternately red and blue-green 90° out-of-phase with the respective blue-green and red flashes of line 120 and single-color dots 821 and 822. When the phase adjustment has converged the center line, the two color images of dot 823 appear to have a maximum vibration-induced angular separation. The user adjusts the vibration driver amplitude, thereby adjusting the perceived dot separation to converge the red flash of dot 823 with the blue-green flash of dot 821, and the blue-green flash of dot 823 with the red flash of dot 822, to form two white dots. To the extent that angular image response of the eye depends on angular deflection of corneal surface 806 and on the well-known refractive index of the cornea (or of the type of contact lens resting on the cornea, which must be provided as computer input), this amplitude adjustment step tells the computer the excitation required to achieve a reference angular tilt response amplitude of the cornea. The amplitude response scaling equation is adjusted for the typical effect of lens vibrational movement on the observed angular response. Given the opthalmic radius-curvature, these angular response sensitivity measurements may be converted to displacement amplitude responses elsewhere on the eye. The resulting data tell the computer substantially the same thing that ultrasound data tell the computer in the whole organ embodiment, namely, the amplitude and phases of organ vibration velocities associated with surface-measured forces and velocities at a number of frequencies. (As mentioned, a miniature variant of the whole-organ embodiment can determine intraopthalmic pressure using ultrasound instead of visual measurements.)

A final refinement permits application of the network algorithm to intraophthalmic pressure determination. Applicability of this refinement depends on a combination of pulsatile pressure-change amplitude in the eye, patient visual acuity, and the maximum opthalmic vibration amplitude determined to be safe. Since the intraopthalmic pressure pulsates somewhat with blood pressure, convergence of line 820 will not be steady. The patient is asked to adjust frequency until line convergence is achieved at one peak of the opthalmic pressure waveform, with the red line moving above the blue-green line at other times. The patient is then asked to adjust frequency for convergence at the opposite extreme of the pressure waveform, with the red line moving below the blue-green line at other times. This frequency-separation at constant phase is easily translated into phase-separation at constant frequency, given the results of other measurements. Finally, the patient is asked to adjust the angular separation of dots 821 and 822 (e.g. by mechanical adjustment of the strobe optics) to match the peak separation observed from pressure-induced variation in convergence of line 820. This adjused spacing, measured and digitally-interfaced, tells the computer the amplitude of the pulsatile response-variation measurement. This completes the data collection needed for applying the network algorithm, thus further refining the pressure determination.

The vibration amplitudes and energy levels allowable in this embodiment mut be restricted for safety reasons, particularly to avoid risk of retinal detachment. For this reason, the visual display screen subtends a small visual angle and illumination is made quite bright, to maximize visual acuity for small-vibration observations. The vibration driver system can sense approximate response amplitudes and precise applied vibrational power levels without the benefit of visual observations. The system is designed both to monitor and restrict maximum excitation levels, and to be electrically incapable of delivering dangerous vibrational energy levels.

There are time-varying display alternatives to the stroboscopic display described above, e.g. an oscilloscope with horizontal sinusoidal beam deflection at the driver frequency. Vibrational response of the eyeball to the driver acting above or below the cornea will cause a vertical deflection of the prescribed spot, resulting in a perceived lissajous ellipse or circle if the spot deflection frequency matches opthalmic excitation frequency. The appearance of a circle or ellipse with vertical and horizontal symmetry axes then indicates a $+$ or $-90°$ phase angle between spot deflection and opthalmic vibration response, while the appearance of a sloping line segment indicates a 0° or 180° phase angle. Many designs for variable displays synchronized to vibration driver excitations can produce perceived colors and geometric patterns indicative of opthalmic vibration responses.

DESCRIPTION OF THE PULMONARY ARTERY PRESSURE EMBODIMENT

Figure 14:
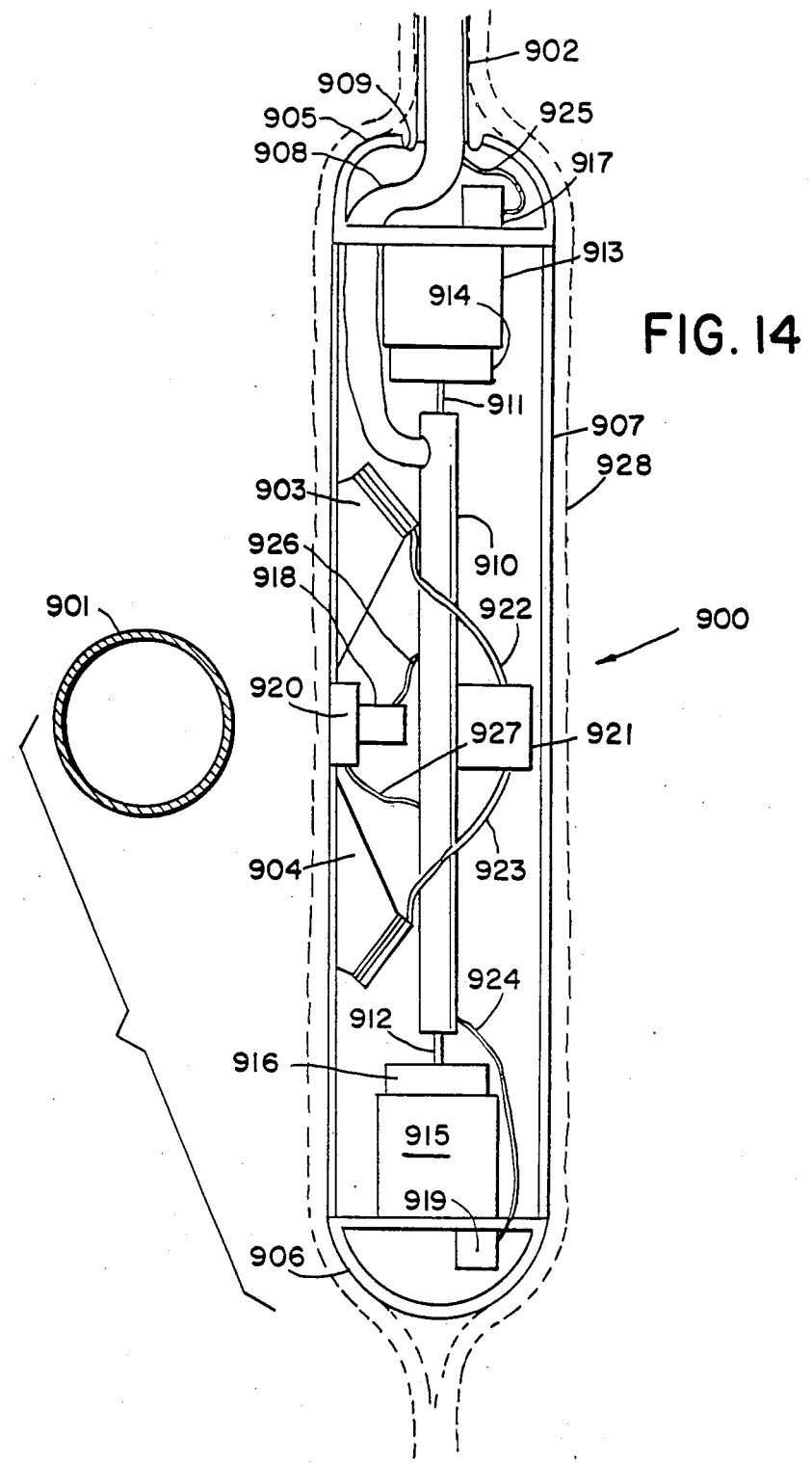
FIG. 14 is a diagrammatic cutaway view of the vibration driver and sensors in a pulmonary arterial pressure-measuring aspect of the invention.

Another variation of the invention is adapted for measuring blood pressure in the right pulmonary artery, in the vicinity where the artery crosses roughly horizontally at right angles to the esophagus. Vibration driver/sensor assembly 900 of FIG. 14 is swallowed and positioned partway down the esophagus, opposite pulmonary artery segment 901, shown in section. The esophageal wall is indicated by dashed line 928. The assembly is rotated and adjusted vertically via flexible cable 902.

The assembly, shown cut open, contains a pair of defocused ultrasound transducer assemblies, 903 and 904, which are very similar in construction, relative positioning and function to assemblies 62 and 65 of FIGS. 2 and 3, described in conjunction with the systemic artery pressure embodiment. By manual axial positioning of assembly 900, the operator matches the depths of two artery-wall echo traces on an oscilloscope, as with traces 13 and 14 of FIGS. 1 and 7. Rotational alignment achieves maximum echo signal strength from the artery-wall target. This is accomplished in much the same way that the operator adjusts assembly 1 of the systemic artery pressure embodiment to align with the underlying artery, using a digital signal-strength readout.

Vibrational excitation is generated through length-change of assembly 900, as curved end caps 905 and 906 vibrate axially. Cylindrical housing 907 stretches to allow the relative motion of the end caps. This housing is a composite structure of compliant polymer (e.g. silicone rubber) with circumferential filaments (e.g.

fiberglass) that minimize diameter changes but affect bending and length change minimally. Cable 902 emerges into curving segment 908 passing through cap 905 and into housing 907, providing vibration decoupling between external cable 902 and cap 905. Flexible membrane 909, bridging the circular gap between cable 902 and cap 905, is curved into 905 to roll with axial cap motion for vibration decoupling. Thrust between the end caps is supported by rigid tube 910, which terminates in end plugs from which emerge thin, short flexible rod segments 911 and 912, whose proportions give high bending compliance with low axial compliance and no buckling under working axial loads. Axial drive is provided by two magnetic driver assemblies consisting of housings 913 and 915, which move axially relative to their central magnet/winding assemblies terminating in pedestals 914 and 916. Rod segments 911 and 912 terminate in pedestals 914 and 196, transferring thrust from the pedestals to tube 922 while allowing limited bending of the housing and end caps. The driver housing and pedestal are analogous to housing 801 and pedestal 804 of FIG. 13, as described in relation to the opthalmic pressure embodiment. Detection of relative vibrational motion of the end caps is by analysis of driver electrical responses, using circuitry similar to that used in the whole organ and opthalmic pressure embodiments.

End-segment motion compresses and decompresses the gas (e.g. air) in housing 907 without significantly perturbing the housing diameter, so that vibrational excitation is analogous to an acoustic suspension loudspeaker with twin drivers at the ends of a closed cabinet of rigid diameter. A net volume-change vibration drive is desired, since this motion induces a vibration field that attenuates more gradually and smoothly over space than constant-volume vibration modes. The hoop stiffness of housing 907 prevents radius-change from offsetting volume changes caused by end-motion, while the high bending flexibility (within angular limits) prevents housing rigidity from interacting significantly with tissue vibrations that bend the housing.

As the relatively rigid and heavy spinal column lies immediately dorsal to assembly 900, on the right in FIG. 14, the tissue displacements off moving end caps 905 and 906 normally interact to produce significant lateral translational vibrations and bending vibrations in the assembly. Acceleration sensors 917, 918 and 919 detect left-right lateral vibrations near the top, center and bottom regions, respectively, of assembly 900, thus quantifying translational and bending motions in a plane substantially perpendicular to the axis of artery 901. The ultrasound-detected arterial motions are minimally affected by un-measured vibration components.

To provide still more data, fluid pressure sensor 920 is placed adjacent to acceleration sensor 918, on the assembly surface closest to artery 901. This sensor detects pressure exerted on the sensor assembly surface adjacent to the artery, responding from DC up through the vibration-frequency band of the drivers. Hence, the sensor can feel the low-frequency push as artery 901 expands with each heartbeat, and it can feel the effects of changing tissue stresses related to the diameter-change of the artery. In this way, the low-frequency pulsations of the artery itself are examined as a vibrational excitation that indicates properties of the artery and its near surroundings.

Cable 908 enters tube 910. The ultrasound coaxial cable travels via tube 910 to assembly 921, which contains high frequency transformers and transistor switches like those in assembly 56 of FIGS. 2 and 3. The switches couple ultrasound signals either via wire pair 922 between 921 and ultrasound assembly 903, or via wire pair 923 between 921 and ultrasound assembly 904, depending on a selection control voltage, as discussed in the analogous situation for the systemic artery pressure embodiment. Flexible wire braid 924, originating from cable 908 (which extends from cable 902), emerges from tube 910 to couple power and signals to and from acceleration transducer 919. Likewise braid 926, also originating from cable 908, emerges from tube 910 to couple power and signals to and from assembly 918, and similarly for braid 927 and assembly 920. Similar braid 925 emerges directly from cable 908 to couple to acceleration transducer 917.

The system gathers substantial data about the artery, including both frequency-baseline and pressure-baseline variations. Because of lag between pressure and diameter responses observed in the pulmonary artery (apparently caused by visco-elastic creep response in the artery wall), vibrations are sometimes measurable at equal radii and with sufficient pressure separation to permit solution of the network algorithm to useful accuracy. Preliminary to network solution, simulation algorithm techniques are applied to translate the three-dimensional vibration field problem into an equivalent two-dimensional problem, amenable to network techniques taught in conjunction with the systemic artery pressure embodiment.

Application of the simulation algorithm involves representing the system as interacting simple vibrating shapes. At a distance, the vibration fields from end caps 905 and 906 appear very similar to the fields of two spheres vibrating in the simplest volume-change mode. The spinal column to the right of assembly 900 in the diagram acts like a partial vibration mirror, creating the effect of a second image-pair of vibrating spheres. The field strength, phase and apparent distance (presumed directly to the right) of these image spheres from assembly 900 are inferred from the translational motions of acceleration sensors 918, 919 and 920. The resulting effective four-source field induces smoothly-tapering Mode 1 and Mode 2 excitations in the pulmonary artery, with minimal excitation of Mode 3 and above. Designing for the correct spacing between end caps 905 and 906 relative to their expected distance to the right of artery 901 helps to minimize average Mode 3 excitation. As there are pressure and stress variations axially along the artery, there is axial vibrational flow, resulting in net cross-section area change in the ultrasound plane. This appears as Mode 0 vibrational excitation in the ultrasound plane. The Mode 1 and Mode 2 vibrations vary slowly enough with respect to axial distance along the artery that axial motion associated with axial rate-of-change of these modes can be ignored. Hence, Mode 1 and Mode 2 excitations are treated as simple two-dimensional modes locally, anywhere along the artery length. The three-axis ultrasound system provides enough data to resolve Mode 0 from Mode 2 unambiguously in the ultrasound plane without symmetry assumptions (not the case with Mode 1 and Mode 3 excitation), since Mode 0 motion is described entirely by a single amplitude and a single phase (unlike Modes 1, 2 and 3, each of which can exhibit two amplitudes and two phases because of the possible differing-axis excitations).

The excitatory field of the four vibrating spheres can be resolved computationally, at any point along the artery length, into an axial translation, a transverse translation (observed as Mode 1), a transverse two-dimensional shear in the cross-sectional plane (observed as Mode 2), and a shear component associated with Mode 0 motion in the cross-sectional plane, accompanied by an axial velocity gradient. Of these vibration components, the transverse shear component associated with Mode 2 excitation accounts for most of the vibrational energy flow that is pressure-sensitive. Focusing on this component, a network algorithm solution is obtained, using pressure-baseline data at constant diameter. From the four-source vibration field model, the axial variation in Mode 2 excitation is estimated and an effective excited length calculated as follows. The Mode 2 excitation amplitude as a function of axial position is divided by the amplitude computed for the ultrasound-plane. This amplitude ratio is squared (giving an energy ratio) and integrated with respect to distance over the length of the pulmonary artery. The resulting integral is the effective excited length. For network algorithm solution, driver force and velocity may be interpreted as axial force and relative axial velocity of the end caps. Two-dimensional force associated with the ultrasound-measured vibrations is axial force divided by the effective excited length just described. The network algorithm is then solved by the methods shown in the context of the systemic artery pressure embodiment. (If the image-pair vibration is significantly phase-shifted from the primary pair, a more complicated network algorithm may be needed, taking into account differing effective excited arterial lengths for two different vibration phases.) Network solution data feed into the analytic function fit algorithm, yielding values for absolute pressure.

Further computational refinements provide a consistency check for the network solution, as well as an estimate for tissue elasticity around the pulmonary artery, which can mimic blood pressure significantly for the low pressure range of concern (typically below 30 mm Hg). The heart-rate pulsations sensed by surface-pressure sensor 910 help give an estimate of tissue elastic modulus near the artery. The measured pressure response is sensitive to tissue shear stresses acting normal to the sensor surface. Correlating these stresses with pulsating ultrasound-measured artery diameter and distance gives an indication of tissue elasticity.

The network solution gives an estimate of changing blood pressure that can be correlated with pulsatile diameter changes to estimate artery diameter elasticity. The four-source vibration simulation predicts Mode 0 excitation along the artery length. Combining this prediction with ultrasound-measured Mode 0 response and with an elastic tube vibration model (based on Fourier analysis and the elastic tube theory that has been used to study pulse wave propagation in arteries), an independent estimate of diameter elasticity is obtained. Comparing these two elasticity estimates gives a consistency check.

Since the network solution just described relies on data showing pressure differences at equal diameters, and since the lag between pressure and diameter changes can be small, the accuracy of the data for this simplest kind of network solution may be compromised. Better results then require diameter-correction procedures analogous to those described for the systemic artery pressure embodiment. Since Mode 0 vibrations are sensitive to diameter pulsations, Mode 0 energetics may need to be simulated and incorporated into a network algorithm with diameter-change correction. This simulation is approached using methods indicated above and under "Simulation Algorithms". Note that methods taught for applying a two-dimensional network algorithm to a three-dimensional flow situation are applicable e.g. in the systemic artery pressure embodiment, for correcting computations where flow does not accurately approximate a two-dimensional field.

OTHER EMBODIMENTS

Systems Simplified by Low Damping

If vibrations are not strongly damped by tissue viscosity, phase varies little through most of the vibration field, and effective vibrating mass is hardly affected by viscous shear forces. Then pressure is related simply to geometry, average density and a resonant frequency where organ excitation force is in phase with response velocity. This is useful e.g. in a simplified intraopthalmic pressure embodiment taking advantage of low damping and the fact that driver force is altered minimally by transmission through the eyelid. The user adjusts frequency to converge a line strobed at force maxima, thus matching the phases of driver force and opthalmic velocity response. A simple formula relates adjusted frequency, opthalmic radius and estimated effective average density to pressure. The system achieves useful accuracy without a determination of driver velocity.

Expanded Digital Processing

The signal processing so far described uses analog circuits up to the outputs of the demodulator modules. From there, digital algorithms take over to solve the mathematical equations described in the text. The analog-digital interface boundary can be moved. For example, the simultaneous network equations can be solved by analog computation. For economy and flexibility, however, there are advantages to expanding digital processing in the invention, eliminating analog circuitry and moving the A to D interface toward the sensors. For example, the audio-band signals entering the circuitry of FIG. 9 can be sampled and digitized directly and the demodulation functions moved into the digital domain. Even direct sampling and digitization of ultrasound signals is possible, though not necessarily a good approach. Digital demodulation involves digital multiplication of signal quantities and formation of averages using fixed weighting factors. By careful sequencing of sampling and computation in relation to analog signal phases, multiplications by arbitrary quantities can be reduced. Microprocessor computation time is typically minimized by algorithms that use sorting, summing, differencing, halving and doubling of quantities to minimize multiplications by multi-bit quantities. Pre-scaling of variables to permit fixed-point arithmetic rather than floating-point also saves time. Mathematically inexact approximations of processes described here often yield adequate results while conserving computer power. Thus, the economy and feasibility or real-time digital processing is influenced profoundly by good software design.

Multiple Simultaneous Frequency Processing

The circuitry described so far induces, measures and analyzes responses at only one frequency at a time. With additional circuitry or added computation function, it is possible to excite responses and analyze data at several frequencies simultaneously. This approach has the advantage that a full spectrum of response data containing both pressure and frequency baseline information can be gathered at once, e.g. during a single heartbeat, reducing or eliminating reliance on analyzing matched pressure cycles. Multi-frequency digital signal processing often need not keep pace with real-time events, since frequency baseline data is typically needed only for calibration of the sensor-patient coupling. Real-time blood pressure monitoring (either systemic or pulmonary) typically requires processing only at a single frequency. Hence, the computer can store multi-frequency signal data rapidly during a calibration heartbeat and process the data over a longer period of time.

Multi-frequency processing is described as a modification and extension of the analog processing and data acquisition of FIG. 7 and accompanying text. The demodulation and signal-generation processes described can be implemented digitally as well as by analog modules. In one approach, several sinusoid oscillators operate simultaneously at different frequencies. The outputs are summed and amplified to energize the vibration driver. The response data then contains multiple frequencies. To analyze data at one of the oscillator frequencies, that oscillator output is used separately as a demodulator phase reference signal. A quadrature sinusoid at the same frequency is also derived. The audio-band response signals are demodulated with respect to the two reference-frequency phases. (Depending on bandwidths, it may be necessary to use demodulation multipliers that are linear in both quadrants, to avoid unwanted distortion products.) With proper filtering and sufficient frequency spacing, the demodulator outputs represent responses only at the frequency of the phase-reference sinusoid. Hence, a second set of demodulators using a second sinusoidal frequency reference yields independent response data at that frequency, and so on. Note that a response signal, e.g. velocity or force, is no longer appropriate to use as a demodulator phase reference, since such a signal contains several frequencies. After all signal quantities are demodulated at a given frequency for both reference phases, one signal quantity, generally complex-valued, may be chosen as a reference and complex-divided into the other signal quantities, as an optional scaling procedure.

Multi-Sensor, Multi-Driver Systems

The amount and accuracy of information yielded by a system to excite, measure and analyze vibrations depends on the number and quality of measurements taken. A system capable of inducing vibrations from many points and detecting many independent response parameters can ultimately resolve more physiological data than a simple system. Computation methods described under "Simulation Algorithms" are applicable in such complex environments.

One possible multi-sensor, multi-driver system can be described in terms of a multiplicity of modules like the one of FIGS. 10 and 11, as described for whole-organ measurements. Each driver/sensor module should include means for sensing its location and orientation is space as it contacts the patient. Location sensing is accomplished e.g. using three spring-retracted cables extending straight to each module, with the cable payout lengths measured. Orientation sensing can be gyroscopic. The ultrasound transducers of the modules operate in a sequence that avoids unwanted interference while organ dimensions and vibration parameters are evaluated along multiple paths. The vibration drivers are activated e.g. one at a time to perform frequency sweeps. The activated driver measures its own force and velocity output, while inactive drivers sense force and velocity passively at their surfaces. As the drivers perform their frequency sweeps, the system gathers sufficient vibration data to constrain the unknown parameters of a detailed simulation model. Ultrasound dimension data aids in constraining the model. Once the simulation parameters are adjusted to provide good agreement between modeled and measured responses, those parameters give a detailed picture of the mechanical properties of the tissues and organs under study.

Simulation Algorithms

This section discusses mathematical simulations of vibrational flow in visco-elastic, incompressible tissues. At each point in the tissue, flow is a vector velocity, and each vector direction component is represented by a complex number, characterizing vibrational amplitude and phase. The vibration field equations, involving pressure gradients and shear stresses, are separable into component equations involving pressure without shear effects, and shear stresses without pressure effects. Shear forces are associated with viscosity and elasticity, but the two properties are easily combined into a single, frequency-dependent complex coefficient. Shear-induced velocities tend to be confined to boundary layers whose influence drops off rapidly with distance, so that shear velocity fields can often be ignored at a distance from a vibrating object. The deeper-penetrating pressure fields are simpler to compute than shear fields. In many instances, only the pressure field need be computed in detail.

Both the pressure and shear equations have relatively simple solutions for parallel planar layers and two-dimensional flow, or for concentric cylinders or concentric spheres. To compute interactions among spheres, cylinders and flat-surfaced vibrators requires translation of vibration fields between the coordinates of different symmetries. In this translation, orthogonality between vibration modes breaks down, so that a single mode in one symmetry influences a number of modes in another symmetry. A combination of Fourier analysis and solutions of simultaneous linear equations frequently suffices to solve boundary constraint problems for interacting geometries.

Iterative functional minimization procedures finally determine best-fit parameters of a simulated vibrating system, in order to match actual body vibration measurements with their simulated counterparts. The best-fit parameters reveal fluid pressures and the tissue properties of organs and blood vessels.

Mathematical Simplifications

Two related topics of classical mechanics overlap in simulation analysis for this invention: the theory of viscous fluid flow, and the theory of elastic solids. For the vibrations of interest with this invention, compressibility is negligible, so that all shape deformations of tissue may be described as shear deformations—an important simplification. Because the analysis is concerned only with low-amplitude, low-velocity vibrations, fluid and elastic behaviors are non-turbulent and linear, a further simplification. Because vibrations are small, the shapes of vibrating objects change only negligibly within the limits of a cycle, permitting the simplifying approximation that in certain aspects of analysis, boundary shapes are considered constant despite vibrations.

Dimensional Analysis

The Reynolds number is a familiar non-dimensional parameter of fluid dynamics, expressing a ratio of inertial to viscous forces. If two flow situations involve similar boundary shapes and matched Reynolds numbers, then the flow velocity fields will be geometrically similar (other effects being equal). In the small-vibration context, fluid flow Reynolds numbers are essentially zero, implying that inertia is dominated by viscosity. Vibrational flow analysis differs greatly from steady flow analysis, however, since inertia must be overcome with each reversal of flow direction. Hence, vibration frequency multiplies the effect of inertia. A different non-dimensional scale parameter is useful for expressing the vibrational ratio of inertial to viscous forces. The Reynolds number is expressed as a flow velocity multiplied by a size-defining length (e.g. a water pipe radius), all divided by the kinematic viscosity of the fluid. For a vibrational counterpart to the Reynolds number, substitute frequency multiplied by length where velocity was used. Hence, a constant product of frequency times length-squared, divided by kinematic viscosity, implies vibrational flow similarity.

The square-root of this Reynolds number analog is especially useful for analysis. We designate this number "R", suggesting Radius, since the parameter expresses radius in units of a characteristic length over which inertia and viscous forces are comparable. This characteristic length is the denominator square-root expression of Eq. 36, and divides dimensional radius "r", the numerator. The terms under the square root are angular frequency "f" and kinematic viscosity "nu".

$$R = r/\mathrm{SQRT}(nu/f) \quad [36]$$

(In the specialized context of pulsating axial fluid flow in tubes, this number is called the "Womersley Frequency paramter"—see Womersley, J. R., "An Elastic Tube Theory of Pulse Transmission and Oscillatory Flow in Mammalian Arteries", *WADC Tech. Rep.*, 56-614, 1957.)

The parameter "R" arises in correcting the vibration analysis for changing arterial diameter. When radius "r" varies, a constant equivalent frequency and radius is maintained if the product "f·r$^2$" is held constant. We see that this maintains "R" constant. In the simplified case of an artery with a zero-thickness wall in uniform surroundings, this adjustment maintains a similar flow geometry and an identical impedance from inertia and viscosity. Thus, maintaining a constant f·r$^2$ product can be useful for isolating the effect of pressure change on an impedance measurement when pressure and radius change interdependently.

Now consider an arterial wall of significant thickness. Assume that "f" is adjusted with changing "r" of the midpoint in the wall thickness, in order to maintain the midpoint "R" constant. Since wall cross-section is constant, wall thickness varies as 1/r. Hence, non-dimensional wall thickness, proportioned to constant "R", varies as 1/r$^2$. To correct vibration measurements for this change in proportions calls for simulation methods to be shown.

Separability of Basic Flow Equations

The analysis begins with familiar fluid flow equations expressing two constraints:

(1) Continuity of an incompressible medium demands that for any fixed volume in the medium, the net flow influx through the surface of the volume must be zero at all times;

(2) Newton's Law, Force=(Mass×Acceleration), must be satisfied for any fluid element in each coordinate direction. The Newton's Law equations are frequently referred to as the momentum equations.

To satisfy Newton's Law, there are two important sources of force to consider: pressure, and shear stresses. The latter are caused by the viscosity and elasticity of the medium. There is a very important theorem for dealing with pressure and shear stresses. (The theorem, discovered independently in developing this invention, may be previously known, but if so, it is not widely known and is not reported in advanced texts on fluid mechanics.) The theorem states that inside a region of uniform density, viscosity and shear modulus, a flow geometry determined by both pressure and shear stresses can be separated into two component flow geometries. The first component geometry is determined entirely by pressure gradients and density, independent of shear effects. To solve for this geometry, the powerful theory of potential flow is applicable. The second component geometry is determined entirely by shear forces and density, independent of pressure effects. The shear field equations are simplified by the absence of pressure gradients. Each component flow solution must obey the equation of continuity. The correct overall flow velocity field is the specific combination of the potential flow and shear flow solutions that matches the motions of the boundary of the uniform region.

The independence of the potential flow equations from viscosity and elasticity is counter-intuitive. Viscosity and elasticity induce non-zero shear stresses in a potential flow field, but surprisingly, these stresses balance to give no net force on any volume entirely within the uniform medium. Shear stresses become unbalanced, creating a net force, only at boundaries of discontinuity in fluid and elastic properties, or where non-vibrational tension in a tissue layer (e.g. as caused by fluid pressure containment) causes a restoration force toward an equilibrium shape.

The velocity potential function of non-viscous steady flow analysis is an abstraction, having no obvious physical counterpart. In vibrational flow, the velocity potential corresponds to vibrational pressure. The vibrational pressure gradient results directly in fluid acceleration. Fluid velocity lags acceleration by 90°.

Given this separation of the Newton's Law equations for flow in a visco-elastic medium, we may discuss separate potential and shear flow solutions for geometries of interest. Wherever tissues with differing properties come in contact, the vibrational flow solutions for regions on either side of the interface must give matching velocities at the boundary, and the net effect of pressures and shear stresses must balance both parallel and normal to the interface. It is possible for vibrational pressure to be discontinuous across a boundary, provided that the discontinuity is offset by an opposite discontinuity in vibrational stress acting normal to the boundary surface. This vibrational stress discontinuity can arise from vibrational shear forces or from non-vibrational tension (e.g. from pressure containment) interacting with vibrationally-changing curvature. There must be no cross-boundary discontinuity in shear stresses paralleling a boundary surface.

The vibrational flow simulation task is largely to determine the combinations of potential and shear flow solutions within regions that match properly at the boundaries. For symmetric geometries such as concentric spherical or cylindrical tissues, this matching task reduces to evaluating flow functions and solving simultaneous linear equations, generally no more than four complex-valued equations at a time. When non-concentric geometries interact (e.g. a flat disk vibrator perturbing an underlying spherical organ), the vibrations in the coordinates of one geometry must be translated into vibration components in the coordinates of the other geometry. Through this translation, a single vibration mode in one geometry generally excites a series of modes in the interacting geometry. Hence, orthogonality of vibration modes vanishes with loss of symmetry. Solutions come to involve systems of many simultaneous equations. The mode translations from geometry to geometry generally involve Fourier analysis or comparable function-correlation integrals. A concrete example is sketched below.

Complex Viscosity Incorporates Elasticity

In the context of arterial blood pressure determination, tissue viscosity is important, and elasticity other than pressure-induced elasticity is negligible, except possibly within a hardened arterial wall. For probing the much lower pressure range of the pulmonary artery, tissue elasticity is significant. For vibrational probing of organs, tissue elasticity is one of the most important diagnostic parameters. Consequently, organ-probing driver frequencies range low enough to bring out tissues elasticity effects, which become increasingly dominant at low frequencies.

Elasticity is a tendency of a substance to return from deformation to an original shape. Viscosity is a tendency of a substance to resist any rate-of-deformation in shape. Elasticity stores energy, while viscosity dissipates energy. In visco-elastic tissues, elasticity and viscosity are not simply additive, since there is usually elastic "creep". With creep, a tissue deformed from a shape forgets that original shape progressively over time, re-equilibrating toward the new shape. Since creep dissipates stored mechanical energy, creep causes a time-dependent viscosity, as well as a time-dependent elasticity.

The relationship of creep to elasticity and viscosity is more easily described in the frequency domain. If there is elastic creep, then the shear modulus decreases with decreasing frequency, to reflect how the tissue progressively forgets a previous shape with increasing duration of the deformation cycle. As shear modulus decreases, viscosity increases to reflect the added dissipation of stored mechanical energy.

The relationship between elastic modulus and viscosity as functions of frequency can be described in terms of the analytic properties of a complex viscosity function whose real part is ordinary viscosity and whose imaginary part relates to shear modulus. We designate ordinary absolute viscosity by "mu", and complex viscosity by "MU", whose real and imaginary parts are called "MUr" and "MUi". MUi is expressed in terms of shear modulus "Y", divided by the complex quantity "j·f", for "j"="square root of $-1$", and "f"="radian frequency". In Eq. 37, both mu and Y are functions of f, being invariant with respect to f only in the absence of creep:

$$MU = mu + Y/j \cdot f \quad [37]$$

The function "MU" of the argument "j·f" is analytic, that is, it has a unique complex derivative. The j·f argument is imaginary for a pure frequency signal but may take on any complex value for the purposes of mathematical analysis. The properties of analytic functions relate mu and Y in this context. The analytic function fit algorithm and the Hilbert Transform (both described previously) apply to analyzing the frequency interdependence of elasticity and viscosity.

Complex kinematic viscosity "NU" is defined as absolute viscosity "MU" divided by density "$\rho$":

$$NU = MU/\rho \quad [38]$$

One may write the equations for vibrational viscous flow, and by substituting a complex viscosity coefficient for ordinary viscosity, the equations apply to visco-elastic flow. This technique works even for many non-Newtonian fluids like cake batter and silicone putty, fluids that exhibit short-term memory, or decaying elastic behavior. The difficulties fall away in part because at any fixed frequency, the combined effects of elasticity and creep separate neatly into an elastic component, appearing in the imaginary part of the complex viscosity coefficient, and a viscous component, appearing in the real part. The other simplification is that many non-Newtonian fluids are difficult to deal with because of non-linear or non-isotropic behaviors manifested only with large shear deformations. These behaviors often disappear for small-amplitude vibrations.

There are minor limitations to the analytic simplification being described here, as applied to the analysis of living tissues. Certain tissues are highly non-isotropic, even in their responses to small vibrations. This is seldom a problem in the context of this invention. For example, striate muscle tissue is non-isotropic, having differing viscous and elastic properties along the fibers and across them. The properties are symmetric for the two directions within a cross section cutting perpendicular to the length of the fibers. In analyzing vibration fields in a plane of symmetry, that plane is usually the plane of isotropic behavior. Where anisotropic tissues appear in thin layers, the anisotropy between in-plane and across-plane directions is of little consequence to vibration analysis on a relatively large scale. Thus, many anisotropic sheathings of connective tissue can be treated as if they were isotropic, with negligible error.

Planar, Cylindrical and Spherical Solutions

There are three symmetries of flow geometry that yield to particularly simple analysis: concentric cylinder symmetry; concentric sphere symmetry with vibration symmetric through an axis; and planar symmetry with long waves standing or traveling along a flat surface and penetrating into the medium below. In all three cases, flow geometry may be described in two dimensions, in an appropriate cross-section. Symmetry takes care of the remaining dimension. Further, for these particular symmetries, the two-dimensional partial differential equations split neatly into separate ordinary differential equations for each coordinate. The overall solution is the product of the component solutions.

Once the separability of potential and shear functions is recognized and once the complex viscosity coefficient described above is incorporated as a tool, mathematicians can readily set up and solve the planar-wave vibration equations. Therefore, only a sketch is provided here. The potential-flow solutions are the familiar equations for sinusoidal surface waves on a non-viscous liquid. For each wavelength, one solution decays exponentially with depth and the other solution grows exponentially with depth. vibrational phase is independent of depth. These solutions are expressed elegantly in terms of the complex exponential function. The undamped shear solutions are known as Rayleigh waves. The less familiar damped shear solutions involve a sinusoidal function along the surface, multiplied by the exponential function of depth, but with a complex exponential argument. Again, there are two depth functions at a given surface wavelength, one growing with depth and the other decaying with depth. Shear vibrational phase is not constant with depth, and the vibration field is not analytic, i.e. the complex velocity function is not related directly to a function having a unique complex derivative.

Combining planar vibration solutions in a double complex Fourier series, it is possible to model a vibration field having two-dimensional symmetry in a uniform medium below a flat surface vibrator. This technique is useful in conjunction with embodiments of the invention that deal with a shallow artery whose diameter changes significantly with changing pressure. The double Fourier series consists of a potential flow series and a shear flow series, both including only solutions that decay with depth. The sum of the two series solutions must match the motion of the vibrator, and elsewhere the sum must obey the boundary constraints of a free surface. For a finite series, the solution will be approximate and periodic over surface length, representing an infinite row of vibrators spaced widely enough not to interfere seriously with each other. The technique can be extended to multiple, parallel tissue layers, in which case layers with a lower boundary must be represented by quadruple Fourier series solutions, involving potential and shear flow functions that increase and decay with depth.

The cylindrical and spherical solutions are very similar to each other in form. They consist of a function of angle multiplied by a function of radius. The angle functions are a discrete series of vibration modes, such as are illustrated in FIG. 6. The radial functions are solutions to second-order homogeneous ordinary differential equations. Associated with any mode number (corresponding to a given surface wavelength in the planar case) are exactly four radial solutions—two potential and two shear. One potential and one shear solution diverge at infinit radius. The other potential and the other shear solution diverge at zero radius. Since these solutions are difficult, their determination procedures are outlined here.

To express and solve these cylindrical and spherical equations in the most general form, we must extend our definition of non-dimensional radius "R" from Eq. 36 to the case of complex kinematic viscosity "NU", of Eq. 38, according to Eq. 39;

$$R = r \cdot SQRT(f \cdot Nux/(NUx^2 + NUy^2)) \quad [39]$$

We further characterize the ratio of elastic to viscous components of complex NU by the ratio "q" of Eq. 40:

$$q = -NUy/NUx = y/(f \cdot mu) \quad [40]$$

With these definitions, we can write the equations governing potential and shear flow for cylindrical and spherical geometries. We begin with the cylindrical case. If "u" is velocity in a radial direction and "v" is velocity in a tangential direction, associated with non-dimensional radius "R" and angle "$\theta$", then we have:

$$u = U \cdot \cos(n \cdot \theta) \cdot EXP(j \cdot f \cdot t) \quad [41]$$

$$v = V \cdot \sin(n \cdot \theta) \cdot EXP(j \cdot f \cdot t) \quad [42]$$

We have split u and v into radial complex amplitude functions, U and V, multiplied by circumferential sine and cosine functions for Mode n, and finally multiplied by the complex EXPonential function giving the dependence on frequency and time. Adding a real constant to the cosine and sine arguments rotates the mode shape in space. Vibrational phase shift and amplitude adjustment to satisfy boundary constraints is accomplished by multiplying U and V solutions by an appropriate complex scaling coefficient.

There are two types of U solutions, potential and shear solutions "Up" and "Us". These are solutions to the following equations:

$$\delta^2 Up/\delta R^2 = (-3/R)(\delta Up/\delta R) + ((n^2 - 1)/R^2) Up \quad [43]$$

$$\delta^2 Us/\delta R^2 = (-3/R)(\delta Us/\delta R) + (((n^2 - 1)/R^2) - q + j) Us \quad [44]$$

The difference between the potential and shear equations is the addition of the elasticity correction, q, and the imaginary unit, j, to the shear equation. The imaginary j-term in Eq. 44 causes the solutions to spiral in the complex plane about the R-axis. The potential flow equation contains no imaginary terms. The potential flow solution is real, exhibiting no "spiraling", i.e. no vibrational phase shifts with changing R. In fact, for any given Mode n, any potential solution can be expressed as a linear combination of exactly two potential flow functions (allowing for complex scaling coefficients), $R^{n-1}$ and $R^{-n-1}$. Similarly, for a given Mode n and elasticity correction q, all shear solutions can be expressed in terms of just two shear flow functions. These can be evaluated by numerical integration along the R-axis, using almost any integration procedure (e.g. Runge-Kutta or, as is especially efficient here, a Taylor series incrementation). Let the solution that diverges at infinity and converges at zero be called the "zero-solution". Similarly, let the solution that diverges at zero and converges at infinity be called the "infinity-solution". To obtain the zero-solution for any range of R exceeding a given minimum Rmin, start at an R below Rmin with an arbitrary initial solution (e.g. Us=1, $\delta Us/\delta R=0$) and integrate for increasing R. The first integration steps will give a combination of both solutions, but the infinity-solution will decay rapidly while the desired zero-solution will grow rapidly, to dominate the entire solution. It is always possible to pick a positive starting R that is small enough to give arbitrarily good separation of the zero-solution from the infinity-solution above a given Rmin. Evaluate complex Us and $\delta Us/\delta R$ over a range above Rmin, for Rmin>1, and store the results in two tabulated functions, Us and $\delta Us/\delta R$, of the argument R. Tabulate points for R=1. Standarize the magnitudes and phases by dividing each tabular entry by the original complex value obtained for Us at R=1. In this way, the function is standardized to Us=1 at R=1. This tabular function may be defined as the zero-solution. Similarly, the infinity-solution for any range of R below a given Rmax and for a given q and Mode n is evaluated by starting with with an arbitrary initial U and δU/δR. Beginning from R sufficiently above Rmax>1, integrate for decreasing R. The desired infinity-solution quickly dominates. As before, tabulate the function below Rmax and rescale the function and derivative results to standardize to Us=1 at R=1. This gives the infinity-solution.

For rapid computation of the two shear functions, pre-compute and store an array of function tables as described in the paragraph above, for needed Modes n (typically not past n=4), and for the needed range of q. These tables may be stored in read-only memory or loaded into random-access memory along with the microprocessor control program. Let the q-spacing be small enough to permit accurate polynomial spline interpolation along that array axis. (Interpolation of the complex logarithm of the function and derivative may prove more accurate). The R-spacing can be fairly large. To evaluate, say, the infinity-solution for given R and q, pick the next-larger tabulated R in the infinity-solution tables, interpolate along the q-axis of the array to the desired q, and then use numerical integration to move back from the tabulated R to the desired R. To evaluate a desired zero-solution, use the zero-solution tables, pick the next-lower tabulated R, interpolate to the desired q, and integrate forward to the desired R. Using this technique, it is not necessary to integrate far enough to obtain separation of the two solutions, for the tabular values of Us and δUs/δR used for starting already provide the desired separation. Tabular spacing of R is clearly a tradeoff between memory allocation and function computation time. The absolute magintudes and phases of the solutions obtained are always scaled to fit a boundary condition. One normally needs to know only the complex ratio of a U-function going from one R to another R, corresponding to inner and outer boundaries of a continuous region of tissue. The non-dimensional R parameters are always computed first, starting with actual radius r and solving for R in Eq. 39.

Because of desirable mathematical properties of the differential equations just given, the solutions are consistent with the continuity constraint, or incompressibility condition. The V-solution is obtained from any U-solution (either Up or Us) by applying the continuity constraint. This is expressed simply:

$$V = (-1/n)(U + R(\delta U/\delta R)) \quad [45]$$

The equations governing vibrational flow for spherical symmetry with the vibration axis corresponding to the spherical axis are similar, but somewhat more involved. In place of the trigonometric functions "cos (n·θ)" and "sin (n·θ)" of Eqs. 41 and 42, we substitute functions designated, respectively, "C(θ)" and "S(θ)". The functions C and S are different for each Mode number n. These functions are solutions to Eqs. 46 and 47:

$$\delta^2 C/\delta\theta^2 + \cot(\theta)\cdot\delta C/\delta\theta + N\cdot C = 0 \quad [46]$$

$$\delta S/\delta\theta + S\cdot\cot(\theta) = C(\theta) \quad [47]$$

The number "N" must be chosen to give a function periodicity of 2·pi, in order that C and S be single-valued for a given angular position. The eigenvalues of N that satisfy this closure condition correspond to Mode numbers n. Solutions for N, C and S as functions of n are given in Table 1 for n from 0 to 3.

TABLE 1

| | | Spherical Vibration Functions of Angle | |
|---|---|---|---|
| n | N | C | S |
| 0 | 0 | 1 | 0 |
| 1 | 2 | $\cos(\theta)$ | $\sin(\theta)$ |
| 2 | 6 | $\frac{1}{4} + (\frac{3}{4})\cos(2\theta)$ | $(\frac{1}{4})\sin(2\theta)$ |
| 3 | 12 | $(\frac{3}{8})\cos(\theta) + (\frac{5}{8})\cos(3\theta)$ | $(1/32)\sin(\theta)\sin(3\theta)$ |

The mode shapes are slightly distorted from the single-component sinusoids of the cylindrical solutions, although the mode shape graphs appear very similar to the drawings of FIG. 6. Given these angle functions, we now move on to the spherical radial functions U and V, keeping the same notation as for the analogous cylindrical equations above:

$$\delta^2 Up/\delta R^2 = (-4/R)(\delta Up/\delta R) + ((N-2)/R^2)Up \quad [48]$$

$$\delta^2 Us/\delta R^2 = (-4/R)(\delta Us/\delta R) + (((N-2)/R^2) - q + j)Us \quad [49]$$

As before, the shear equations differ from the potential equations only in the addition of the q-term and the imaginary unit, j. The functional behavior is quite similar to the cylindrical cases. For a given n and corresponding eigenvalue N, the two potential solutions are power-law functions of R, as is easily shown by substitution. The two shear solutions converge at zero and infinity, and they spiral about the R-axis in the complex plane.

As before, V comes from any U solution using the continuity equation. The solution shown is independent of Mode number n or the eigenvalue N, since these parameters are incorporated into the definition of the functions C and S. Hence, we have simply:

$$V = -R(\delta U/\delta R) - 2U \quad [50]$$

Regions Dominated by Potential Flow

We can see some important generalized function properties embodied in the examples of these vibration field solutions for cylindrical and spherical symmetry. Observe that the shear flow solutions are much more localized in their influence than the potential solutions. Consider the flow field exterior to a cylinder driven to vibrate by an interior energy source. If the medium surrounding the cylinder is approximated as uniform to infinity, then only the infinity-solution to the differential equations gives appropriate convergence. This shear solution goes to zero roughly exponentially with increasing R, while the corresponding potential solution converges to zero only as a negative power of R (determined by Mode number n). Hence, far from a surface, the potential field dominates. This comparison holds for spheres and for other shapes as well. The comparison fails for periodic surface waves, but when these waves are combined using Fourier techniques to represent the field of a long vibrator plate, the properties discussed here emerge. Hence, the generalization about local shear fields and relatively penetrating potential fields applies where a flat circular vibration driver is placed above a roughly spherical organ, as in the embodiment of the invention for probing whole organs. Let us see how this is useful.

If an organ below a circular vibrator plate is relatively deep, then the shear-flow field of the vibration driver will affect the organ much less than the potential field. Unless large tissue discontinuities generate local shear flow fields in the organ's vicinity, the field coupled to the organ can be approximated by a pure potential field. The potential flow solution for a flat disk was solved decades ago as an exercise in acoustics, and is easy to compute on a microprocessor. The task at hand is to compute an "effective vibrator" whose size and vibration amplitude and phase are corrected, relative to the actual driver plate, to account for the effects of the boundary shear field on the potential field propagated to greater depths. The shear flow solution is computable, given a big enough computer and some time, but a compact synthesis of the result needs to be expressed for rapid microprocessor computation.

Large-computer shear flow solutions can be classified according to the vibration damping factor encountered at the driver, and according to the log-log slope of imaginary driver impedance plotted against frequency. These two non-dimensional parameters, combined with plate diameter and impedance magnitude as scaling factors, define the effective average density, viscosity and shear modulus of tissue below the driver. For any combination of the two non-dimensional parameters just given, the vibration field outside the vibrator shear-flow region can be approximated by an equivalent effective vibrator of adjusted diameter, vibrating at an adjusted amplitude and phase angle relative to the actual vibrator. In this way, the effect of the local shear boundary layer on the deep-penetrating vibration field is expressed compactly as three empirical non-dimensional functions (diameter ratio, amplitude ratio and phase angle increment) of two non-dimensional arguments (driver damping factor and the log-log slope just mentioned). These three functions are derived in advance, using large-computer simulations, and the values are stored in three two-dimensional arrays. The microprocessor evaluates the vibrator correction factors rapidly using polynomial spline interpolation in two dimensions, from the tables. The potential flow field for the adjusted effective vibrating plate is given by a simple mathematical expression.

Interacting Vibration Fields

The principle of linear superposition of function solutions, combined with mode shape analysis resembling Fourier analysis, provides a means for combining the cylindrical, spherical and planar vibration field techniques and quantifying interactions that cross from one symmetry to another. To indicate how, let us continue the simplified example of a circulator vibration driver plate interacting with a roughly spherical organ of unifom tissue in substantially uniform surroundings. We now sketch very briefly a complete system simulation.

To begin the solution, computationally "remove" the organ and fill that volume with tissue like the tissue that surrounds the organ. Now compute the potential field sent by the driver into the underlying uniform tissue, using the "effective vibrator" method. At the boundary of the "missing" organ, compute the potential vibration field velocity components in terms of the spherical organ coordinates, R (fixed at the organ surface radius) and $\theta$ (=0 when pointing toward the driver plate). Resolve these velocities into radial and tangential directions. Similarly determine the first and second derivatives of radial and tangential velocities with respect to coordinates R and $\theta$.

The next task is to compute forces, resolved into the radial and tangential Mode shapes described by the functions C and S, as defined above. Start by computing pressure and shear stresses over the spherical surface. Getting from velocity derivatives to shear stresses resolved across the organ boundary surface requires tensor stress analysis, a well-known area of applied mathematics. To integrate pressures and stresses over the organ surface, in order to define mode-forces, requires careful application of the mode-force definition discussed in relation to the systemic artery pressure embodiment and Eq. 1. Given the various normal and tangential mode-forces, we now determine transfer impedances, Zt, from the vibrator plate to the organ. For each Mode, there are two such impedances to compute, Ztn and Ztt, for normal and tangential Zt. Double the mode-force values described just above. (If the motion at the organ surface is stopped by making the organ rigid, this has the effect of doubling the surface forces, relative to those computed for the organ volume filled with tissue like the surrounding tissue. Stopping the organ motion sets V2 of the network algorithm equations to zero.) For each Mode, set the doubled normal and tangential forces equal to V1·Ztn and V1·Ztt, using actual (not "effective") driver plate velocity V1. Finally, divide through these two equations by V1, yielding Ztn and Ztt, for the given Mode.

Now we can put the organ back in place, computationally. For the symmetry of the organ in its surroundings, the spherical vibration functions and tensor stress analysis are used to compute network terminal-2 normal and tangential self-impedances, Z2n and Z2t, for each Mode number. To get a pure normal-velocity vibration to compute Z2n requires a particular linear combination of potential and shear flow functions. A different linear combination of the same functions gives the pure tangential-velocity vibration to compute Z2t. Only zero-solutions may be used inside the organ, and only infinity-solutions outside the organ. The final step is to solve for actual normal and tangential vibration velocity responses, based on V1, on the transfer impedances, and on the self-impedances, for each mode and at any frequency. These results are all predicated on assumed densities, viscosities and shear moduli for the organ and its surroundings, and on the geometry. Using transfer impedances, the force experienced by the vibration driver plate is corrected for the presence of the organ.

Matching Empirical Data

The measurement system tells the computer the driver impedances and induced motions it actually observes at a number of frequencies. The task now is to adjust the parameters of the simulation model so that computed and observed parameters match as closely as possible. There are a number of well-known generalized algorithms available for minimizing function-fit errors. It is clear that rapid simulation methods are essential if a generalized simulation of any complexity is to be matched to real-world data in a reasonable time. If a good fit between simulated and empirical measurements can be obtained over a range of frequencies, this lends confidence that the simulation parameters represent actual properties of the organ and surrounding tissues.

I claim:

1. An non-invasive system for inducing vibrations in a selected element of the human body and detecting the nature of responses for determining mechanical characteristics of said element, said system comprising:
a drive means for inducing multiple-frequency vibrations, including below 20 KHz, in a selected element of the body,
means for determining parameters of the vibration exerted on the body by the driver means,
means for sensing variations of a dimension of said element of the body over time, including in response to said driver means,
means for correlating said variations with frequency components of operation of said driver means below 20 KHz, in order to determine corresponding frequency components of said variations.
means for resolving said frequency components into components of vibration mode shape, and
computer means for interpreting said parameters of vibration exerted by the driver means and said components of vibration mode shape in a manner to determine said mechanical characteristics.

2. The system of claim 1 wherein said parameters of vibration exerted by the driver means include force.

3. The system of claim 1 wherein said parameters of vibration exerted by the driver means include velocity.

4. The system of claim 1 wherein one said mechanical characteristic determined is pressure.

5. The system of claim 1 wherein said system further comprises means for detecting change in said components of vibration mode shape due to pressure change of said element, said change being included by said computer indetermination of said mechanical characteristics of said element.

6. The system of claim 1 wherein said driver means is adapted to induce a vibration frequency that changes over time.

7. The system of claim 1 wherein said driver means is adapted to induce multiple vibration frequencies simultaneously.

8. The system of claim 1, 4 or 5 wherein said body element includes a wall, and further comprising:
means for resolving said components of vibration mode shape for at least two modes, and
means for comparing said determined mechanical characteristics of said elements respectively determined on the basis of said components of vibration mode shape for at least two modes in a manner to provide an indication of element wall stiffness.

9. The system of claim 1, 4 or 5 wherein said means for sensing variations of a dimension of said element of the body comprises means for emitting and receiving ultrasound signals.

10. The system of claim 4 or 5 wherein a said mechanical characteristic determined is systemic arterial blood pressure and said body element is a segment of the arterial system.

11. The system of claim 1 or 5 wherein a said mechanical characteristic determined is the mechanical impedance of a body element and said body element is an entire organ.

12. The system of claim 4 or 5 wherein a said mechanical characteristic determined is intraocular pressure and said body element is an eyeball.

13. The system of claim 12 wherein said means for sensing variations of a dimension of said eyeball comprises a time-varying display adjustable for creating visual impressions representative of the response of the eyeball to the vibrational forces exerted by the driver means.

14. The system of claim 4 or 5 wherein a said mechanical characteristic determined is pulmonary blood pressure and said body element is a segment of the pulmonary arterial system.

15. The system of claim 1 comprising a further means for sensing a dimension of said element, said sensed dimension being included by said computer means in determination of said mechanical characteristics of said element.

16. The system of claim 15 wherein said means for sensing a dimension of said element comprises optical measuring equipment.

17. The system of claim 4 or 5 further comprising means for applying a known pressure to said element in a manner to permit calibration of the system.

18. The system of claim 17 wherein the pressure application means is a pressure cuff.

19. The system of claim 1 wherein said means for sensing variations of a dimension is further adapted for sensing a dimension of said element, said sensed dimension being included by said computer means in determination of said mechanical characteristics of said element.

20. The system of claim 19 wherein said means for sensing a dimension of said element comprises equipment for emitting and receiving ultrasound signals.

21. A method for inducing vibrations in a selected element of the human body and detecting the nature of responses for determining mechanical characteristics of said element non-invasively, said method comprising the steps of:
inducing multiple-frequency vibrations, including below 20 KHz, in a selected element of the body by use of a driver means,
determining parameters of the vibration exerted on the body by the driver means,
sensing variations of a dimension of said element of the body over time, including in response to said driver means,
correlating said variations with frequency components of operation of said driver means below 20 KHz to determine corresponding frequency components of said variations,
resolving said frequency components into components of vibration mode shape, and
interpreting said parameters of vibration exerted by the driver means and said components of vibration mode shape in a manner to determine said mechanical characteristics of said element.

22. The method of claim 21 wherein said determination of parameters of vibration exerted by the driver means includes determining force.

23. The method of claim 21 wherein said determination of parameters of vibration exerted by the driver means includes determining velocity.

24. The method of claim 21 wherein a mechanical characteristic determined is pressure.

25. The method of claim 21 further comprising the step of detecting change in components of vibration mode shape due to pressure change of said element, said change being included in determination of said mechanical characteristics of said element.

26. The method of claim 21 wherein said multiple-frequency vibrations are generated by changing the operation frequency of the driver means over time.

27. The method of claim 21 wherein said multiple-frequency vibrations are generated by operation of the driver means at multiple frequencies simultaneously.

28. The method of claim 21, 24 or 25 wherein said body element includes a wall, and further comprising the steps of:
resolving said components of vibration mode shape for at least two modes, and
comparing said determined mechanical characteristics of said elements respectively determined on the basis of said components of vibration mode shape for at least two modes in a manner to provide an indication of element wall stiffness.

29. The method of claim 21, 24 or 25 comprising sensing said variations of a dimension of said element of the body by means of ultrasound echo signals.

30. The method of claim 24 or 25 wherein a said mechanical characteristic determined is systemic arterial blood pressure and said body element is a segment of the arterial system.

31. The method of claim 21 or 25 wherein a said mechanical characteristic determined is the mechanical impedance of a body element and said body element is an entire organ.

32. The method of claim 24 or 25 wherein a said mechanical characteristic determined is intraocular pressure and said body element is an eyeball.

33. The method of claim 32 wherein said step of sensing variations of dimension comprises sensing variations of a dimension of said eyeball, and said method further comprises incorporating user feedback in response to visual impressions of a time-varying display, said visual impressions being representative of the response of the eyeball induced by the driver means.

34. The method of claim 24 or 25 wherein a said mechanical characteristic determined is pulmonary blood pressure and said body element is a segment of the pulmonary arterial system.

35. The method of claim 21, in addition to the step of sensing variations of a dimension of said element, said method further comprises sensing a dimension of said element, said sensed dimension being included in determination of said mechanical characteristics of said element.

36. The method of claim 35 wherein said dimension of said element is sensed by interpreting ultrasound echo signals.

37. The method of claim 35 wherein said dimension of said element is sensed optically.

38. The method of claim 24 or 25 further comprising applying a known pressure to said element in a manner to permit calibration.

39. The method of claim 38 further comprising applying said known pressure by means of a pressure cuff.

* * * * *